US007122017B2

(12) United States Patent
Moutafis et al.

(10) Patent No.: US 7,122,017 B2
(45) Date of Patent: *Oct. 17, 2006

(54) FLUID JET SURGICAL INSTRUMENTS

(75) Inventors: Timothy E. Moutafis, Gloucester, MA (US); Kevin Staid, Lowell, MA (US); Donald C. Freeman, Jr., Burlington, MA (US)

(73) Assignee: Hydrocision, Inc., Billerica, MA (US)

( * ) Notice: Subject to any disclaimer, the term of this patent is extended or adjusted under 35 U.S.C. 154(b) by 395 days.

This patent is subject to a terminal disclaimer.

(21) Appl. No.: 10/100,499

(22) Filed: Mar. 18, 2002

(65) Prior Publication Data

US 2002/0177802 A1     Nov. 28, 2002

Related U.S. Application Data

(63) Continuation of application No. 09/313,679, filed on May 18, 1999, now Pat. No. 6,375,635.

(51) Int. Cl.
| A61B 17/20 | (2006.01) |
| A61B 17/32 | (2006.01) |
| A61M 1/00 | (2006.01) |
| A61M 3/00 | (2006.01) |

(52) U.S. Cl. .......................... 604/22; 604/35; 604/43; 606/159; 606/167

(58) Field of Classification Search ............... 604/22, 604/19, 27–28, 35, 39, 40, 42–43, 93.01, 604/149–150; 606/167, 159, 170
See application file for complete search history.

(56) References Cited

U.S. PATENT DOCUMENTS 1,889,425 A     11/1932  Sorensen (Continued)

FOREIGN PATENT DOCUMENTS

DE           40 18 736 A1     1/1992

(Continued)

OTHER PUBLICATIONS

Communication Pursuant to Article 96(2) EPC dated Nov. 3, 2003 for corresponding European Patent Application Serial No.: 00 932 590.3.

(Continued)

*Primary Examiner*—Nicholas D. Lucchesi
*Assistant Examiner*—Catherine S. Williams
(74) *Attorney, Agent, or Firm*—Wolf, Greenfield & Sacks, P.C.

(57) ABSTRACT

The invention provides a variety of surgical instruments for forming a liquid jet, which are useful for performing a wide variety of surgical procedures. In some embodiments, the invention provides surgical liquid jet instruments having a pressure lumen and an evacuation lumen, where the pressure lumen includes at least one nozzle for forming a liquid jet and where the evacuation lumen includes a jet-receiving opening for receiving the liquid jet when the instrument is in operation. In some embodiments, the pressure lumen and the evacuation lumen of the surgical liquid jet instruments are constructed and positionable relative to each other so that the liquid comprising the liquid jet, and any tissue or material entrained by the liquid jet can be evacuated through the evacuation lumen without the need for an external source of suction. The invention also provides a variety of surgical liquid jet instruments that are constructed and configured specifically for use in a surrounding liquid environment or a surrounding gaseous environment. The invention also provides a variety of surgical liquid jet instruments that are rotatably deployable from an undeployed position, for insertion into the body of a patient, to a deployed position, in which there is a separation distance between the liquid jet nozzle and the jet-receiving opening that defines a liquid jet path length. The invention also provides surgical methods utilizing the inventive surgical liquid jet instruments, and methods for forming components of the surgical liquid jet instruments.

51 Claims, 20 Drawing Sheets

U.S. PATENT DOCUMENTS

| | | | |
|---|---|---|---|
| 1,902,418 A | 3/1933 | Pilgrim | |
| 3,565,062 A | 2/1971 | Kuris | |
| 3,590,813 A | 7/1971 | Roszyk | |
| 3,818,913 A | 6/1974 | Wallach | |
| 3,930,505 A | 1/1976 | Wallach | |
| 4,024,866 A | 5/1977 | Wallach | |
| 4,111,490 A | 9/1978 | Liesveld | |
| 4,137,804 A | 2/1979 | Gerber et al. | |
| 4,245,624 A | 1/1981 | Komiya | |
| 4,282,867 A | 8/1981 | Du Toit | |
| 4,294,251 A | 10/1981 | Greenwald et al. | |
| 4,368,734 A | 1/1983 | Banko | |
| 4,435,902 A | 3/1984 | Mercer et al. | |
| 4,560,373 A | 12/1985 | Sugino et al. | |
| 4,583,531 A | 4/1986 | Mattchen | |
| 4,637,551 A | 1/1987 | Seeger, Jr. et al. | |
| 4,690,672 A | 9/1987 | Veltrup | |
| 4,694,828 A | 9/1987 | Eichenbaum | |
| 4,715,848 A | 12/1987 | Beroza | |
| 4,735,620 A | 4/1988 | Ruiz | |
| 4,798,339 A | 1/1989 | Sugino et al. | |
| 4,827,679 A | 5/1989 | Earle, III | |
| 4,839,492 A | 6/1989 | Bouchier et al. | |
| 4,898,574 A | 2/1990 | Uchiyama et al. | |
| 4,913,698 A | 4/1990 | Ito et al. | |
| 4,935,006 A | 6/1990 | Hasson | |
| 4,937,985 A | 7/1990 | Boers et al. | |
| 5,002,546 A | 3/1991 | Romano | |
| 5,018,670 A | 5/1991 | Chalmers | |
| 5,027,792 A | 7/1991 | Meyer | |
| 5,037,431 A | 8/1991 | Summers et al. | |
| 5,052,624 A | 10/1991 | Boers et al. | |
| 5,057,098 A | 10/1991 | Zelman | |
| 5,074,862 A | 12/1991 | Rausis | |
| 5,111,652 A | 5/1992 | Andre | |
| 5,125,582 A | 6/1992 | Surjaatmadja et al. | |
| 5,135,482 A | 8/1992 | Neracher | |
| 5,135,484 A | 8/1992 | Wright | |
| 5,162,016 A | 11/1992 | Malloy | |
| 5,186,714 A | 2/1993 | Boudreault et al. | |
| 5,195,958 A | 3/1993 | Phillips | |
| 5,205,779 A | 4/1993 | O'Brien et al. | |
| 5,217,465 A | 6/1993 | Steppe | |
| 5,230,704 A | 7/1993 | Moberg et al. | |
| 5,242,449 A | 9/1993 | Zaleski | |
| 5,250,065 A | 10/1993 | Clement et al. | |
| 5,259,842 A | 11/1993 | Plechinger et al. | |
| 5,300,022 A | 4/1994 | Klapper et al. | |
| 5,314,375 A | 5/1994 | O'Brien et al. | |
| 5,318,518 A | 6/1994 | Plechinger et al. | |
| 5,320,599 A | 6/1994 | Griep et al. | |
| 5,322,504 A | 6/1994 | Doherty et al. | |
| 5,370,609 A | 12/1994 | Drasler et al. | |
| 5,395,315 A | 3/1995 | Griep | |
| 5,441,482 A | 8/1995 | Clague et al. | |
| 5,449,369 A | 9/1995 | Imran | |
| 5,453,088 A * | 9/1995 | Boudewijn et al. | 604/43 |
| 5,454,827 A | 10/1995 | Aust et al. | |
| 5,468,028 A | 11/1995 | Olson | |
| 5,476,450 A | 12/1995 | Ruggio | |
| 5,496,267 A | 3/1996 | Drasler et al. | |
| 5,505,729 A | 4/1996 | Rau | |
| 5,524,821 A | 6/1996 | Yie et al. | |
| 5,527,330 A * | 6/1996 | Tovey | 606/167 |
| 5,551,448 A | 9/1996 | Matula et al. | |
| 5,556,406 A | 9/1996 | Gordon et al. | |
| 5,562,640 A | 10/1996 | McCabe et al. | |
| 5,562,692 A | 10/1996 | Bair | |
| 5,591,184 A | 1/1997 | McDonnell et al. | |
| 5,607,391 A | 3/1997 | Klinger et al. | |
| 5,620,414 A | 4/1997 | Campbell, Jr. | |
| 5,643,299 A | 7/1997 | Bair | |
| 5,674,226 A | 10/1997 | Doherty et al. | |
| 5,697,281 A | 12/1997 | Eggers et al. | |
| 5,709,697 A | 1/1998 | Ratcliff et al. | |
| 5,713,849 A | 2/1998 | Bosma et al. | |
| 5,713,851 A | 2/1998 | Boudewijn et al. | |
| 5,713,878 A | 2/1998 | Moutafis et al. | |
| 5,735,815 A | 4/1998 | Bair | |
| 5,782,795 A | 7/1998 | Bays | |
| 5,785,675 A | 7/1998 | Drasler et al. | |
| 5,788,667 A | 8/1998 | Stoller | |
| 5,792,167 A | 8/1998 | Kablik et al. | |
| 5,853,384 A | 12/1998 | Bair | |
| 5,871,462 A | 2/1999 | Yoder et al. | |
| 5,944,686 A | 8/1999 | Patterson et al. | |
| 5,947,988 A | 9/1999 | Smith | |
| 6,045,564 A | 4/2000 | Walen | |
| 6,066,150 A | 5/2000 | Gonon | |
| 6,083,189 A | 7/2000 | Gonon et al. | |
| 6,096,001 A * | 8/2000 | Drasler et al. | 604/22 |
| 6,099,514 A | 8/2000 | Sharkey et al. | |
| 6,135,977 A | 10/2000 | Drasler et al. | |
| 6,149,622 A * | 11/2000 | Marie | 604/43 |
| 6,216,573 B1 | 4/2001 | Moutafis et al. | |
| 6,280,302 B1 | 8/2001 | Hashish et al. | |
| 6,322,533 B1 | 11/2001 | Gonon | |
| 6,375,635 B1 | 4/2002 | Moutafis et al. | |
| 6,402,715 B1 | 6/2002 | Manhes | |
| 6,419,654 B1 | 7/2002 | Kadan | |
| 6,423,028 B1 | 7/2002 | Gonon | |
| 6,451,017 B1 | 9/2002 | Moutafis et al. | |
| 6,464,567 B1 | 10/2002 | Hashish et al. | |
| 6,491,660 B1 | 12/2002 | Guo et al. | |
| 6,508,823 B1 | 1/2003 | Gonon | |
| 6,511,493 B1 | 1/2003 | Moutafis et al. | |
| 6,544,220 B1 | 4/2003 | Shuman et al. | |
| 6,669,710 B1 | 12/2003 | Moutafis et al. | |
| 2001/0002562 A1 | 6/2001 | Moutafis et al. | |
| 2002/0111579 A1 | 8/2002 | Moutafis et al. | |
| 2002/0176788 A1 | 11/2002 | Moutafis et al. | |
| 2003/0009166 A1 | 1/2003 | Moutafis et al. | |
| 2003/0040763 A1 | 2/2003 | Moutafis et al. | |
| 2003/0055404 A1 | 3/2003 | Moutafis | |
| 2003/0083681 A1 | 5/2003 | Moutafis et al. | |
| 2003/0088259 A1 | 5/2003 | Staid et al. | |
| 2003/0125660 A1 | 7/2003 | Moutafis et al. | |
| 2004/0228736 A1 | 11/2004 | Moutafis et al. | |
| 2004/0230211 A1 | 11/2004 | Moutafis et al. | |
| 2004/0234380 A1 | 11/2004 | Moutafis et al. | |
| 2004/0243157 A1 | 12/2004 | Connor et al. | |

FOREIGN PATENT DOCUMENTS

| | | |
|---|---|---|
| EP | 0 175 096 B1 | 3/1986 |
| EP | 0 253 478 B1 | 1/1988 |
| EP | 0 258 901 A2 | 3/1988 |
| EP | 0 280 972 A1 | 9/1988 |
| EP | 0 367 855 A1 | 5/1990 |
| EP | 0 411 170 A1 | 2/1991 |
| EP | 0 442 579 A1 | 8/1991 |
| EP | 0 470 781 A1 | 2/1992 |
| EP | 0 485 133 A1 | 5/1992 |
| EP | 0 489 496 A1 | 6/1992 |
| EP | 0 551 920 B1 | 7/1993 |
| EP | 0 555 549 A1 | 8/1993 |
| EP | 0 620 016 A1 | 10/1994 |
| EP | 0 636 345 A1 | 2/1995 |
| EP | 0 637 453 A1 | 2/1995 |
| EP | 0 693 295 A1 | 1/1996 |
| EP | 0 737 450 A1 | 10/1996 |
| EP | 0 806 213 A1 | 11/1997 |
| FR | 2 779 934 | 12/1999 |
| FR | 2 779 935 | 12/1999 |

| WO | WO 90/05493 | 5/1990 |
| WO | WO 94/10917 | 5/1994 |
| WO | WO 94/28807 | 12/1994 |
| WO | WO 96/24299 | 8/1996 |
| WO | WO 96/39954 | 12/1996 |
| WO | WO 96/40476 | 12/1996 |
| WO | WO 97/03713 | 2/1997 |
| WO | WO 97/49441 | 12/1997 |
| WO | WO 99/33510 | 7/1999 |
| WO | WO 99/65407 | 12/1999 |
| WO | WO 99/65408 | 12/1999 |
| WO | WO 99/66848 | 12/1999 |
| WO | WO 00/69348 | 11/2000 |
| WO | WO 01/50965 | 7/2001 |
| WO | WO 01/50966 | 7/2001 |

OTHER PUBLICATIONS

Communication Pursuant to Article 96(2) EPC dated Sep. 15, 2004 for corresponding European Patent Application Serial No.: 00 932 590.3.

The International Search Report dated Sep. 27, 2000 for corresponding International Patent Application No. PCT/US00/13732.

Written Opinion dated Mar. 9, 2001 for corresponding International Patent Application No. PCT/US00/13732.

Written Opinion dated Jun. 25, 2001 for corresponding International Patent Application No. PCT/US00/13732.

The International Preliminary Examination Report dated Aug. 13, 2001 for corresponding International Patent Application No. PCT/US00/13732.

Water Jet Dissector, Hepatotom® Supersonic Microjet Dissector brochure, Medical Exports AG.

D.N. Papachristou and B. Barters., "Bisection of the liver with a water jet," Br. J. Surg., vol. 69, pp. 93-94 (1982).

K. Jessen et al., "Endoscopic Jet-Cutting A New Method for Stone Destruction in the Common Bile Duct," 6th Internal Symposium on Jet Cutting Technology, Paper B1, pp. 39-52, Apr. 6-8, 1982.

K. Jessen et al., "Endoscopic Jet Cutting of Human Gallstones," 7th Internal Symposium on Jet Cutting Technology, Paper D4, pp. 211-220, Jun. 26-28, 1984.

B. Aeikens, "Cracking of Ureter Calculi by High Speed Water Jet Pulses," 8th International Symposium on Jet Cutting Technology, Paper 15, pp. 157-166, Sep. 9-11, 1986.

D.A. Summers and J. Viebrock, "The Impact of Waterjets on Human Flesh," 9th International Symposium on Jet Cutting Technology, Paper H4, pp. 423-433, Oct. 4-6, 1988.

J. Uchino et al., "Surgical Cutting of the Liver by Water Jet," 9th International Symposium on Jet Cutting Technology, Poster 1, pp. 629-639, Oct. 4-6, 1988.

B.G. Persson et al., "Transection of the Liver with a Water Jet," Surgery, Gynecology & Obstetrics, vol. 168, pp. 267-268, Mar. 1989.

M.M. Vijay, "A Critical Examination of the Use of Water Jets for Medical Applications," 5th American Water Jet Conference, Paper/Communication 42, pp. 425-448, Aug. 29-31, 1989.

W.J. Drasler et al., "A Rheolytic System for Percutaneous Coronary and Peripheral Plaque Removal," Angiology—The Journal of Vascular Diseases, vol. 42, No. 2, pp. 90-98, Feb. 1991.

H.U. Baer and L.H. Blumgart, "Jet-Cutting—an Alternative to the Ultrasonic Aspirator?" Chirurg, 61:735, 1990 and Reply to commentary.

H.U. Baer et al., "New water-jet dissector: initial experience in hepatic surgery," Br. J. Surg., vol. 78, pp. 502-503, Apr. 1991.

H.U. Baer et al., "Hepatic Surgery Facilitated by a New Jet Dissector," HPB Surgery, vol. 4, pp. 137-146, 1991.

J.E. Field, "The physics of liquid impact, shock wave interactions with cavities, and the implications to shock wave lithotripsy," Phys. Med. Biol., vol. 36, No. 11, pp. 1475-1484, 1991.

J.Y. Giraud et al., "Bone cutting," Clin. Phys. Physiol. Meas., vol. 12, No. 1, pp. 1-19, 1991.

P. Truchot et al., "Development of a Cryogenic Waterjet Technique for Biomaterial Processing Applications," 6th American Water Jet Conference, Paper 35, pp. 473-480. Aug. 24-27, 1991.

H.U. Baer et al., "Subtotal hepatectomy: a new procedure based on the inferior right hepatic vein," Br. J. Surg., vol. 78, pp. 1221-1222, Oct. 1991.

W.J. Drasler et al., "Rheolytic Catheter for Percutaneous Removal of Thrombus," Radiology, vol. 182, pp. 263-267, Jan. 1992.

H.U. Baer et al., "Water-jet dissection in hepatic surgery," Minimally Invasive Therapy, vol. 1 pp. 169-172, 1992.

J.A. Reekers et al., "Catheter for Percutaneous Thrombectomy: First Clinical Experience," Radiology, vol. 188, No. 3, pp. 871-874, 1993.

A.J.A. Terzis et al., "A New System for Cutting Brain Tissue Preserving Vessels: water jet cutting," British Journal of Neurosurgery, vol. 3, pp. 361-366, 1989.

P. Zhong et al., "Propagation of shock waves in elastic solids caused by cavitation microjet impact. II: Application in extracorporeal shock wave lithotripsy," J. Acoust. Soc. Am., vol. 94, No. 1, pp. 29-36, Jul. 1993.

R. Izumi et al., "Hepatic Resection Using a Water Jet Dissector," Surgery Today Jpn. J. Surg., vol. 23, pp. 31-35, 1993.

M. Kobayashi et al., "Experimental Study of Water Jet Angioplasty," Vascular Surgery—International Conference, Oct. 1993, vol. 2, pp. 626-631.

O.M. Schob et al., "The Multimodal Water Jet Dissector—a Technology for Laparoscopic Liver Surgery," End. Surg., vol. 2, pp. 311-314, 1994.

P.C. Douek et al., "Functional Properties of a Prototype Rheolytic Catheter for Percutaneous Thrombectomy In Vitro Investigations," Investigative Radiology, vol. 29, No. 5, pp. 547-552, 1994.

Y. Hata et al., "Liver Resection in Children, Using a Water-Jet," Journal of Pediatric Surgery, vol. 29, No. 5, pp. 648-650, May 1994.

J. Beard, "Water jet puts surgeons at the cutting edge," New Scientist, Jul. 23, 1994.

O.M. Schob et al., "Experimental laparoscopic liver resection with a multimodal water jet dissector," British Journal of Surgery, vol. 82, pp. 392-393, 1995.

S.M. Shimi, "Dissection techniques in laparoscopic surgery: a review," J.R. Coll. Surg. Edinb., vol. 40, pp. 249-259, Aug. 1995.

E.H. Overbosch et al., "Occluded Hemodialysis Shunts: Dutch Multicenter Experience with the Hydrolyser Catheter," Radiology, vol. 201, No. 2, pp. 485-488, 1996.

S. Müller-Hüllsbeck et al., "Rheolytic Thrombectomy of an Acutely Thrombosed Transjugular Intrahepatic Portosystemic Stent Shunt," Cardio Vasc. Intervent. Radiol., vol. 19, pp. 294-297, 1996.

A. Bücker et al., "Comparative in Vitro Study of Two Percutaneous Hydrodynamic Thrombectomy Systems," Journal of Vascular and Interventional Radiology, vol. 7, No. 3, pp. 445-449, May-Jun. 1996.

V.G. van Ommen et al., "Removal of Thrombus from Aortocoronary Bypass Grafts and Coronary Arteries Using the 6Fr Hydrolyser," The American Journal of Cardiology, vol. 79, pp. 1012-1016, Apr. 1997.

R.K. Spence, "Emerging Trends in Surgical Blood Transfusion," Seminars in Hematology, vol. 34, No. 3, Suppl 2, pp. 48-53, Jul. 1997.

* cited by examiner

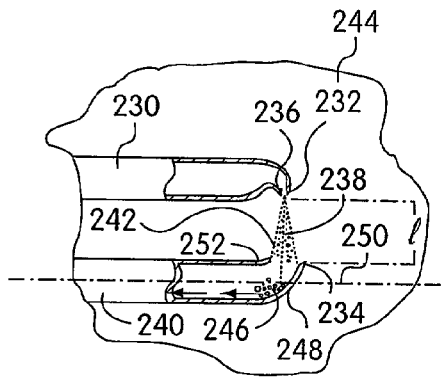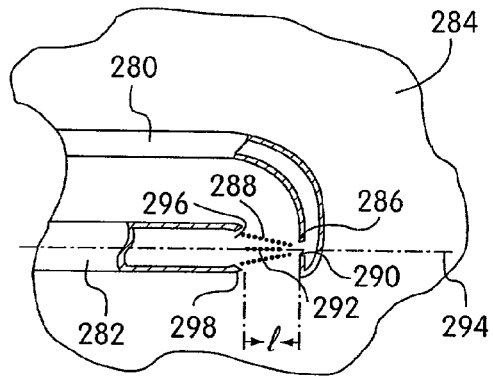
Fig. 5a          Fig. 6a
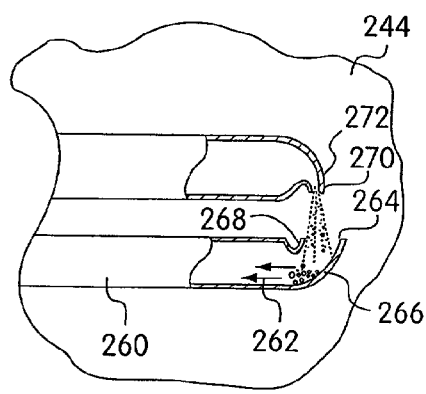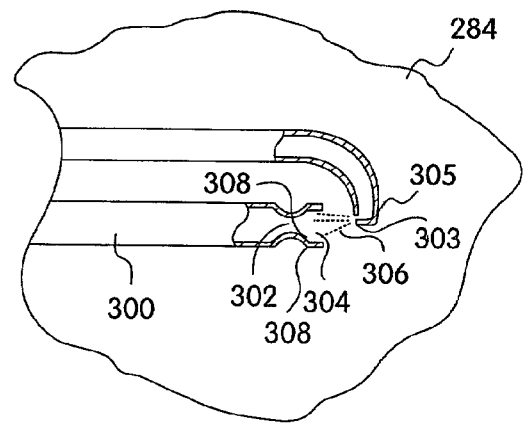
Fig. 5b          Fig. 6b
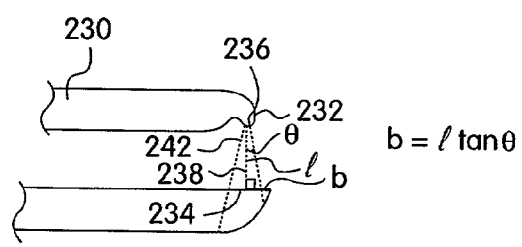
$b = \ell \tan\theta$
Fig. 5c

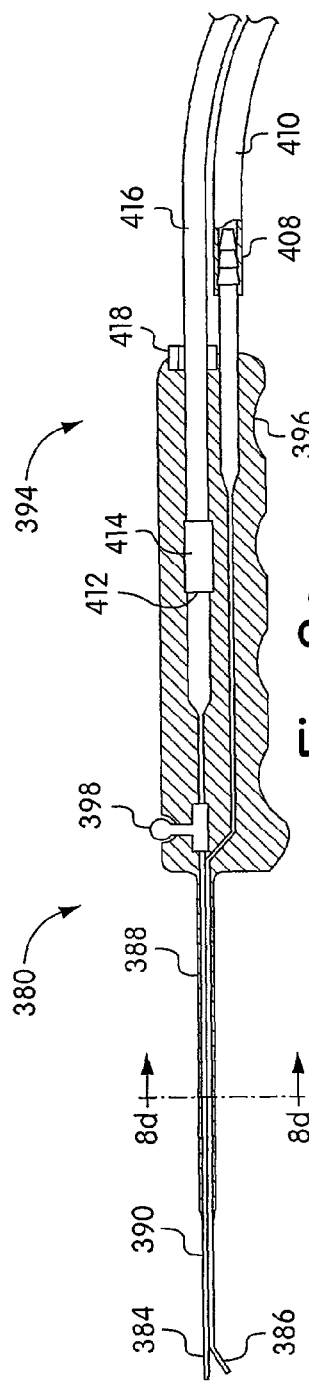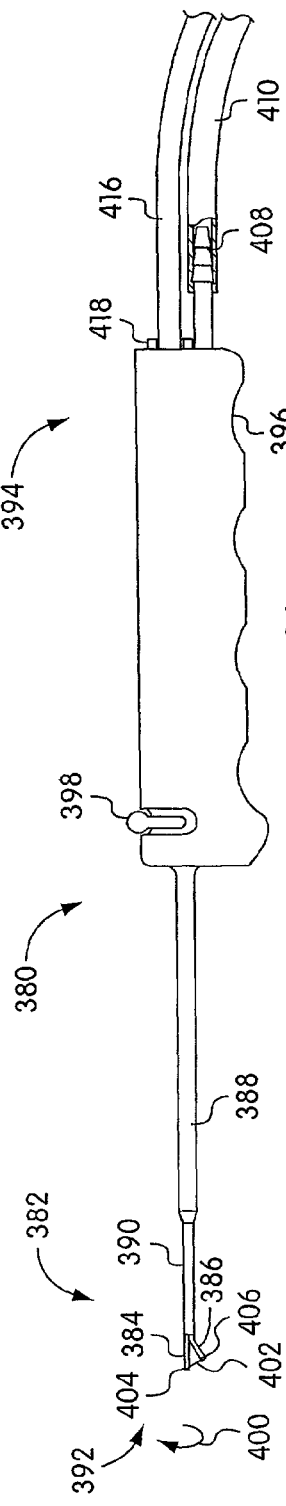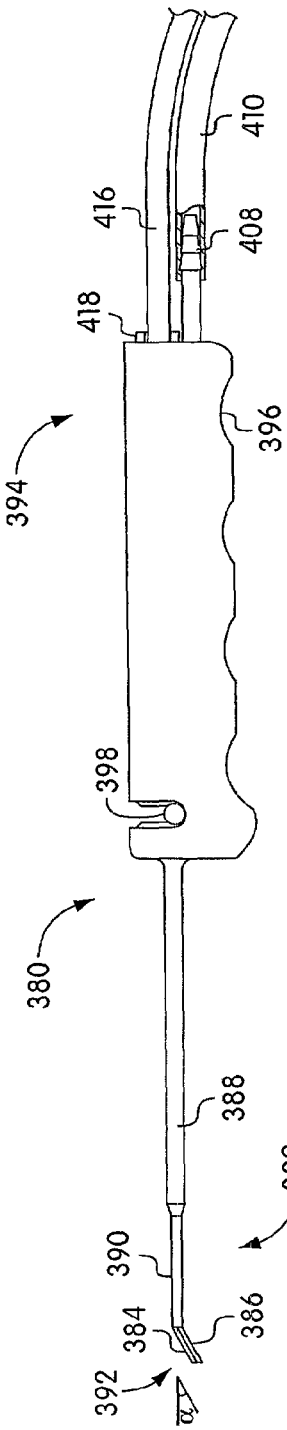

FLUID JET SURGICAL INSTRUMENTS

RELATED APPLICATIONS

This application is a continuation of U.S. patent application Ser. No. 09/313,679, filed May 18, 1999, entitled FLUID JET SURGICAL INSTRUMENTS, and now U.S. Pat. No. 6,375,635, issued on Apr. 23, 2002.

FIELD OF THE INVENTION

The invention relates to surgical instruments for creating a liquid jet and methods for using the instruments in surgical procedures.

BACKGROUND OF THE INVENTION

Traditionally, many surgical procedures have been performed on patients using open surgical methods that utilize relatively large incisions to expose a surgical field. Many traditional methods have also typically utilized surgical tools such as scalpels, scrapers, blunt dissectors, lasers, electrosurgical devices, etc., which have poor tissue differentiating capability and which can easily cause inadvertent damage to tissue surrounding a surgical treatment site unless carefully utilized. Open surgery with such prior art surgical instruments often involves extensive trauma to the patient, with associated problems of long recovery periods and potential complications.

There has been a trend in recent years to perform many surgical procedures using less invasive techniques by accessing surgical sites via small holes through the skin or through body orifices. These techniques are known as "minimally invasive surgery." Minimally invasive surgical techniques commonly employed include endoscopic, laparoscopic, and arthroscopic surgical procedures. Minimally invasive surgical procedures are commonly preferred to open surgical procedures for many applications because the minimally invasive procedures induce less trauma to the patient during surgery and involve, in many cases, fewer potential complications and reduced recovery time.

A variety of instruments have been developed and utilized for minimally invasive surgical procedures. Frequently used instruments include blades and scalpel-type instruments, motorized rotary blade instruments, laser instruments, and electrosurgical or electrocautery instruments. Typically, these prior art instruments suffer from a variety of disadvantages. For example, the instruments can be slow and laborious to use, typically they lack the ability to selectively differentiate tissue to be excised from non-target tissue, they tend to have sizes and/or shapes which make access of many surgical sites difficult, and they tend to cause unintended damage to tissue surrounding the intended target tissue. Most prior art instruments also require the operator to manually remove excised tissue, for example with forceps, or require an external source of vacuum to be applied to the surgical site, for example via an aspiration tube that is separate from the surgical instrument, in order to remove excised tissue. For applications such as arthroscopy, where visualization of the surgical site is typically effected using an imaging system having a probe such as a fiber optic probe inserted into the surgical site, the above mentioned prior art surgical instruments also typically make it difficult to clearly visualize the site of tissue excision within the surgical field by not effectively evacuating tissue and debris from the surgical site.

Instruments that employ liquid jets have also been utilized in surgical procedures for cutting and ablating tissue. Such instruments have many advantages over the above mentioned surgical instruments for performing both open and minimally invasive surgical procedures. For example, the cutting or ablating power of the liquid jet may be adjusted or controlled by an operator of the instrument, for example by varying the pressure of the liquid supplied to form the jet, to allow for improved tissue differentiation and to reduce inadvertent damage to surrounding tissues when cutting or ablating the target tissue. Liquid jet instruments also can avoid the thermal damage to surrounding tissues that is often caused by instruments such as lasers and electrosurgical devices. In recent years, liquid jet instruments have been utilized for a variety of surgical procedures including open surgical procedures such as liver resection, endoscopic procedures such as kidney stone disruption and removal, and arthrectomy procedures for removal of thrombotic tissue from the vascular system.

U.S. Pat. No. 4,898,574 to Uchiyama et al. describes a variety of lithotomic devices for insertion into a body cavity, which create a fluid jet that is utilized to break up and crush calculi, for example kidney stones, in the body of a patient. The instruments disclosed typically include one or more suction channels for removing fluid and debris. The instruments require that the suction channel be coupled to an external source of vacuum, such as a vacuum pump. The instruments disclosed also typically lack a target or deflector upon which the fluid jet impinges, and, therefore, have the disadvantage of potentially causing unintended damage to healthy tissue by misdirection of the fluid jet.

U.S. Pat. No. 4,913,698 to Ito et al. describes a liquid jet surgical handpiece designed for crushing and removing brain tumors in cerebral surgery. The disclosed instrument includes a liquid jet forming nozzle and a suction tube, which is required to be coupled to an external source of vacuum for removal of the tissue and debris excised by the liquid cutting jet. The liquid jet nozzle is oriented in such a manner that the liquid jet from the nozzle is directed towards a confronting inside wall of the tip of the suction tube when the instrument is in operation in order to prevent the liquid jet from inadvertently damaging a non-target tissue.

U.S. Pat. No. 5,135,482 to Neracher discloses a liquid jet instrument for removing a deposit obstructing a vessel in a human body. The device is configured as a multi-lumen catheter, which includes a pressure resistant duct having a nozzle orifice that creates a supersonic cavitating liquid jet. The liquid jet is directed distally from the instrument to ablate a deposit within a vessel. Some embodiments of the catheter device also include a suction lumen which can be coupled to an external source of vacuum for removing liquid and debris from the vessel. The catheter instruments disclosed do not include a deflector or target element to prevent the liquid jet from potentially impinging upon and causing unintended damage to the vessel or tissue surrounding the deposit to be ablated.

U.S. Pat. No. 5,318,518 to Plechinger et al. disclose a fluid jet instrument configured as a catheter for ablation and removal of a material or deposit from a body vessel or hollow organ. The distal end of the catheter includes a fluid jet nozzle that directs a fluid jet into the mouth of a discharging lumen when the instrument is in operation. The discharging lumen includes a mixing tube and diffuser element. The fluid jet directed into the discharging lumen creates an aspiration force, due to eductor pump action, which serves to transport fluid and ablated material through the discharging lumen without the need for an external source of suction. The mixing tube and diffuser element included in the discharging lumen serve to enhance the aspiration force created by the eductor pump action. The fluid jet can shred or shatter tissue or deposits that lie between the nozzle outlet and the inlet of the discharging lumen, and can drive the shattered particles into the inlet of the discharging lumen for evacuation from the surgical site.

U.S. Pat. No. 5,370,609 to Drasler et al. discloses a fluid jet thrombectomy catheter for removing a thrombus deposit from the cardiovascular system of a patient. The catheter includes a pressure lumen for transporting a high pressure liquid to at least one jet nozzle, and a relatively large bore evacuation lumen for removing liquid and ablated tissue and debris. In operation, the catheter is configured to direct at least one liquid jet into the opening of the large-bore evacuation lumen in a direction that is proximal and coaxial with the evacuation lumen. By directing the jet towards the orifice of the large-bore evacuation lumen of the catheter, a stagnation pressure is induced which can propel fluid and debris proximally for removal.

U.S. Pat. No. 5,527,330 to Tovey discloses a fluid jet cutting and suctioning instrument configured, in some embodiments, for laparoscopic insertion into a patient through a trocar. The instrument includes a body having a handle, an irrigation tube that includes a fluid jet nozzle at its distal end, and an evacuation tube, or in some embodiments a backstop member, positioned to receive the fluid jet. Several of the disclosed embodiments involve an instrument for creating a fluid jet that is directed transversely to a longitudinal axis of the body of the instrument. In one embodiment, the instrument includes a sliding sheath element that is able to move the irrigation tube and suction tube laterally with respect to each other to adjust the gap between the fluid jet forming nozzle and the inlet of the suction tube so as to change the length of the fluid cutting jet, when the instrument is in operation. The instruments described by Tovey have several disadvantages for use in many minimally invasive surgical procedures. For example, the shape and design of the irrigation and suction tubes requires the instrument to be relatively bulky and have a cross-sectional dimension and shape that is ill suited for inserting the instrument into confined regions of the body for performing many minimally invasive surgical procedures. In addition, the instruments disclosed are designed so that an external source of suction must be coupled to the suction tube in order to evacuate fluid and ablated tissue from the surgical site.

While the above mentioned surgical liquid jet instruments represent, in some instances, significant improvements over many prior art surgical instruments for performing open and minimally invasive surgical procedures, there remains a need in the art to provide simple, inexpensive, liquid jet surgical instruments which have improved cutting, ablation, and tissue evacuation capabilities, and which have the ability to be utilized in a wide variety of open and minimally invasive surgical procedures. The present invention provides, in many embodiments, such improved surgical liquid jet instruments, and further provides methods for their use in a variety of surgical procedures.

SUMMARY OF THE INVENTION

The present invention provides a series of devices related to surgical procedures utilizing liquid jets for cutting, ablating, sculpting, trimming, etc., tissues and/or materials from the body of a patient. The invention includes, in one aspect, a series of devices comprising surgical liquid jet instruments for forming a liquid jet, in another aspect, methods for using the surgical liquid jet instruments, and, in yet another aspect, methods for forming certain components of the surgical liquid jet instruments.

In one aspect, the invention provides a series of surgical liquid jet devices. One device comprises a surgical instrument for use in a gaseous or liquid environment having a distal end that is adapted to perform a surgical procedure on a patient and a proximal end that is adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen that includes a jet-receiving opening that has a cross-sectional area. The jet-receiving opening of the evacuation lumen is locatable opposite the jet opening at a predetermined distance therefrom to receive a liquid jet when the instrument is in operation. The nozzle is shaped to form a liquid jet as a liquid at high pressure flows therethrough. The liquid jet creates an entrainment region of moving liquid such that essentially all of the moving liquid in the entrainment region is directed into the jet-receiving opening when the instrument is in operation. In addition, the cross-sectional area of the jet-receiving opening and the predetermined distance between the jet opening and the jet-receiving opening are selected so that the entrainment region occupies between 50% and 100% of the cross-sectional area of the jet-receiving opening when the instrument is in operation.

Another device comprises a surgical instrument that has a distal end adapted to perform a surgical procedure on a patient and a proximal end including a body. The body includes a grasping region that is shaped and positionable to be held by the hand of an operator. The instrument includes a pressure lumen that has sufficient burst strength to conduct a high pressure liquid towards the distal end of the instrument and includes at least one nozzle providing a jet opening. The instrument further includes an evacuation lumen, supported by the body, that includes a jet-receiving opening locatable opposite the jet opening at a predetermined distance therefrom to receive a liquid jet when the instrument is in operation. The distal end of the surgical instrument has a predetermined contour and size that is selected to facilitate insertion of the distal end of the surgical instrument into a confined region of a body defining a surgical operating space for a specific surgical procedure.

Yet another device comprises a surgical instrument that has a distal end adapted to perform a surgical procedure on a patient and a proximal end including a body. The instrument includes a pressure lumen that has a sufficient burst strength to conduct a high pressure liquid towards the distal end of the instrument, and that includes at least one nozzle providing a jet opening. The surgical instrument is constructed and arranged to be entirely disposable after a single use.

Another device comprises a surgical instrument that has a distal end adapted to perform a surgical procedure on a patient and a proximal end including a body. The body has a grasping region that is shaped and positionable to be held by the hand of an operator. The instrument includes a pressure lumen having a sufficient burst strength to conduct a high pressure liquid towards the distal end of the instrument. The pressure lumen includes at least one nozzle providing a jet opening. The instrument further includes an evacuation lumen having a jet-receiving opening locatable opposite the jet opening at a predetermined distance therefrom to receive a liquid jet when the instrument is in operation. At least one nozzle included in the instrument comprises a hole in the side wall of a lumen.

Yet another device comprises a surgical instrument having a distal end that is adapted to perform a surgical procedure on a patient and a proximal end that is adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen including a jet-receiving opening locatable opposite the jet opening at a predetermined distance therefrom to receive a liquid jet when the instrument is in operation. The nozzle is shaped to form a liquid jet as a liquid at high pressure flows therethrough, and the liquid jet is directed into the jet-receiving opening when the instrument is in operation. The evacuation lumen includes a region that is within and/or downstream of the jet-receiving opening. The evacuation lumen is shaped and positionable so that a liquid within the region is able to macerate at least a portion of a tissue entrained in the liquid into a plurality of particles when the instrument is in operation.

Another device comprises a surgical instrument that has a distal end that is adapted to perform a surgical procedure on a patient and a proximal end that includes a body. The body has a grasping region that is shaped and positionable to be held by the hand of an operator. The instrument includes a pressure lumen that has a sufficient burst strength to conduct a high pressure liquid towards the distal end of the instrument, and that includes at least one nozzle providing a jet opening. The instrument further includes an evacuation lumen that is supported by the body and that includes a jet-receiving opening locatable opposite the jet opening to receive a liquid jet when the instrument is in operation. At least a portion of the pressure lumen and/or evacuation lumen is rotatably moveable relative to the other for adjusting the separation distance between the jet opening and the jet-receiving opening.

Yet another device comprises a surgical instrument that has a distal end adapted to perform a surgical procedure on a patient and a proximal end that includes a body. The body has a grasping region that is shaped and positionable to be held by the hand of an operator. The instrument includes a pressure lumen that has a sufficient burst strength to conduct a high pressure liquid towards the distal end of the instrument, and that has a distal end including at least one nozzle providing a jet opening. The instrument further includes an evacuation lumen supported by the body that includes a jet-receiving opening, which is locatable opposite the jet opening to receive a liquid jet when the instrument is in operation. The distal end of the pressure lumen is shaped to enable the jet opening to be positionable adjacent to a surface to be ablated or debrided such that a liquid jet emanating from the jet opening is separated from the surface by a distance essentially equal to a wall thickness, at the jet opening, of tubing comprising the pressure lumen.

Another device comprises a surgical instrument that has a distal end adapted to perform a surgical procedure on a patient and a proximal end that includes a body. The body includes a grasping region that is shaped and positionable to be held by the hand of an operator. The instrument includes a pressure lumen that has a sufficient burst strength to conduct a high pressure liquid towards the distal end of the instrument, and that includes at least one nozzle providing a jet opening. The instrument further includes an evacuation lumen that has a proximal end and a distal end. The distal end of the evacuation lumen includes a jet-receiving opening that is locatable opposite the jet opening at a predetermined distance therefrom to receive the liquid jet when the instrument is in operation. The evacuation lumen is shaped and positionable to enable evacuation of essentially all of the liquid comprising the liquid jet from the jet-receiving opening to the proximal end of the evacuation lumen without the need of an external source of suction.

Yet another device comprises a surgical instrument that has a distal end that is adapted to perform a surgical procedure on a patient and a proximal end that includes a body. The body includes grasping region that is shaped and positionable to be held by the hand of an operator. The body includes at least two actuating elements, where each of the at least two actuating elements is adapted to be actuatable by a single hand of an operator holding the grasping region. Each actuating element causes an essentially identical predetermined change in a function, shape, position, or orientation of at least a portion of the distal end of the instrument upon actuation of the element.

Yet another device comprises a surgical instrument that has a distal end that is adapted to perform a surgical procedure in a patient and a proximal end that includes a body. The body includes a grasping region that is shaped and positionable to be held by the hand of an operator. The body includes at least one actuating element that is adapted to be actuatable by a single hand of an operator holding the grasping region. The actuating element is shaped and positionable on the body to enable the operator to hold the body in one of at least two hand/grasping region orientations with a single hand and to effect an essentially identical predetermined change in a function, shape, position, or orientation of at least a portion of the distal end of the instrument, upon actuation of the element, when holding the body in either of the at least two hand/grasping region orientations.

Yet another device comprises a surgical instrument that has a distal end to perform a surgical procedure on a patient and a proximal end adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen that has a proximal end and a distal end and a jet-receiving opening near its distal end that is locatable opposite the jet opening to receive a liquid jet when the instrument is in operation. The evacuation lumen has an internal cross-sectional area which increases essentially continuously from a minimum value at the jet-receiving opening to a maximum value at a predetermined position proximal of the jet-receiving opening. This maximum value is essentially constant at positions proximal to the predetermined position.

Another device comprises a surgical instrument that has a distal end that is adapted to perform a surgical procedure on a patient and a proximal end that is adapted to be controllable by an operator. The instrument includes a pressure lumen comprising a tubular conduit having a distal end and a proximal end. The pressure lumen has a sufficient burst strength to conduct a high pressure liquid towards the distal end of the instrument. The distal end of the tubular conduit has a necked region with a reduced cross-sectional dimension that is less than a cross-sectional dimension of the tubular conduit outside of and proximal to the necked region. The necked region comprises a nozzle that includes a jet opening and is shaped to enable the jet opening to form a liquid jet when a high pressure liquid flows therethrough. The nozzle is oriented so that at least a central region of the liquid jet is directed essentially perpendicular to a longitudinal axis of the conduit outside the necked region. The nozzle is also shaped so that essentially no portion of the jet opening projects radially beyond a perimeter defined by an outer surface of the tubular conduit in a region adjacent to the nozzle but outside the necked region.

In other embodiments, the invention provides devices specifically for use in a gaseous environment. In one such embodiment, the invention provides a device for use in a gaseous environment comprising a surgical instrument that has a distal end adapted to perform a surgical procedure on a patient and a proximal end that is adapted to be controllable by an operator. The instrument includes a pressure lumen having a sufficient burst strength to conduct a high pressure liquid towards the distal end of the instrument, and that includes at least one nozzle providing a jet opening. The instrument further includes an evacuation lumen that has a jet-receiving opening that is locatable opposite the jet opening at a predetermined distance therefrom to receive a liquid jet when the instrument is in operation. The nozzle is shaped to form a liquid jet as a high pressure liquid flows therethrough. The liquid jet comprises a diverging region of liquid droplets moving through the gaseous environment, with the diverging region having an apex located at the jet opening, such that essentially all of the moving liquid droplets in the diverging region are directed into the jet-receiving opening when the instrument is in operation.

Another device for use in a gaseous environment comprises a surgical instrument that has a distal end that is adapted to perform a surgical procedure on a patient and a proximal end that is adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen that has a proximal end and a distal end. The distal end of the evacuation lumen includes a jet-receiving opening that is locatable opposite the jet opening at a predetermined distance therefrom to receive the liquid jet when the instrument is in operation. The evacuation lumen is shaped and positionable to enable evacuation of essentially all of the liquid comprising the liquid jet from the jet-receiving opening to the proximal end of the evacuation lumen without the need for an external source of suction.

Yet another device for use in a gaseous environment comprises a surgical instrument that has a distal end that is adapted to perform a surgical procedure on a patient and a proximal end adapted to be controllable by an operator. The instrument includes a pressure lumen that has a sufficient burst strength to conduct a high pressure liquid towards the distal end of the instrument, and that has a distal end including at least two nozzles, where each nozzle provides a jet opening. Each nozzle is shaped to form a liquid jet as a liquid at high pressure flows therethrough. The instrument further includes an evacuation lumen that has a distal end including a jet-receiving opening that is locatable opposite at least one of the jet openings at a predetermined distance therefrom. The predetermined distance between the at least one jet opening and the jet-receiving opening defines a gas-filled gap between the jet opening and the jet-receiving opening. The jet-receiving opening is shaped and positionable to receive at least one liquid jet when the instrument is in operation.

Yet another device for use in a gaseous environment comprises a surgical instrument that has a distal end that is adapted to perform a surgical procedure on a patient and a proximal end that is adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen that has a jet-receiving opening locatable opposite the jet opening at a predetermined distance therefrom to receive a liquid jet when the instrument is in operation. The nozzle is shaped to form a liquid jet as a liquid at high pressure flows therethrough, and the liquid jet is directed across a gas-filled gap and into the jet-receiving opening when the instrument is in operation. The nozzle and the jet-receiving opening are shaped and positionable relative to each other so that back-flow of a liquid mist or spray from the jet-receiving opening into the gas-filled gap is essentially eliminated when the instrument is in operation.

Another device for use in a gaseous environment comprises a surgical instrument that has a distal end that is adapted to perform a surgical procedure on a patient and a proximal end that is adapted to be controllable by an operator. The instrument includes a pressure lumen that has a sufficient burst strength to conduct a high pressure liquid towards the distal end of the instrument, and that includes at least one nozzle providing a jet opening. The instrument further includes an evacuation lumen including a jet-receiving opening that is locatable opposite the jet opening at a predetermined distance therefrom to receive a liquid jet when the instrument is in operation. The nozzle is shaped to form a liquid jet as a high pressure liquid flows therethrough. The liquid jet is directed across a gas-filled gap and into the jet-receiving opening when the instrument is in operation. The nozzle and the jet-receiving opening are shaped and positionable relative to each other so that a cross-sectional shape and area of the liquid jet at a given location within the evacuation lumen is essentially the same as an internal cross-sectional shape and area of the evacuation lumen at the same given location. The given location comprises the jet-receiving opening and/or a location proximal to the jet-receiving opening.

In yet another aspect, the invention provides methods for utilizing a surgical liquid-jet instrument. In one embodiment, the invention provides a method comprising inserting a surgical liquid-jet instrument into a joint capsule of a patient, creating a liquid jet with the surgical liquid-jet instrument, directing the liquid jet towards a jet-receiving opening in an evacuation lumen of the surgical liquid-jet instrument, and cutting or ablating a selected tissue within the joint capsule with the liquid jet.

In another embodiment, the invention provides a method comprising positioning a surgical liquid-jet instrument in close proximity to a surface of a body of patient, creating a liquid jet in a surrounding gaseous environment with the liquid-jet instrument, directing the liquid jet essentially tangential to the surface and towards a jet-receiving opening in an evacuation lumen, debriding a material from the surface with the liquid jet, and evacuating a liquid comprising the liquid jet and the debrided material from the jet-receiving opening to a proximal end of the evacuation lumen without the need for an external source of suction.

In yet another aspect, the invention provides a method for forming a jet nozzle region in a tube. The method comprises necking down an end of a tube providing a lumen to form a jet nozzle region in the tube that has a reduced cross-sectional dimension. The method further comprises offsetting the jet nozzle region from being essentially co-linear with an axial center line of the tube outside the jet nozzle region to a position where an axial center line of the jet nozzle region is displaced from the axial center line of the tube outside the jet nozzle region by a distance of about d=R−r, where R is the internal radius of the tube outside the jet nozzle region and r is the internal radius of the jet nozzle region.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 5a is a partially-cutaway schematic illustration of a portion of the distal end of a surgical liquid jet instrument for use in a surrounding liquid environment;

FIG. 5b is a partially-cutaway schematic illustration of a portion of the distal end of surgical liquid jet instrument for use in a surrounding liquid environment, where the evacuation lumen includes a constriction;

FIG. 5c is a schematic illustration of a portion of the distal end of a surgical liquid jet instrument, illustrating various geometric relationships;

FIG. 6a is a partially-cutaway schematic illustration of a portion of the distal end of a surgical liquid jet instrument for use in a surrounding gaseous environment;

FIG. 6b is a partially-cutaway schematic illustration of a portion of the distal end of a surgical liquid jet instrument for use in a surrounding gaseous environment, where the evacuation lumen includes a constriction;

FIG. 8a is a schematic illustration of a rotatably deployable surgical liquid jet instrument, where the instrument is in the undeployed configuration;

FIG. 8b is a schematic illustration of the surgical liquid jet instrument as in FIG. 8a, shown in the deployed configuration;

FIG. 8c is a cross-sectional illustration of the surgical liquid jet instrument as in FIG. 8b;

FIG. 11d is a partially-cutaway schematic illustration of a portion of the surgical liquid jet instrument as in FIG. 11a;

FIG. 11e is a partially-cutaway schematic illustration of a portion of the surgical liquid jet instrument as in FIG. 11a;

FIG. 11f is a schematic illustration of the actuating element of the surgical liquid jet instrument as in FIG. 11a;

FIG. 12b is a cross-sectional illustration of the surgical liquid jet instrument as in FIG. 12a;

FIG. 12c is a cross-sectional illustration of the surgical liquid jet instrument as in FIG. 12a;

FIG. 12d is a cross-sectional illustration of the surgical liquid jet instrument as in FIG. 12a;

FIG. 12e is a cross-sectional illustration of the surgical liquid jet instrument as in FIG. 12a;

FIG. 14b is a partially-cutaway schematic illustration of the surgical liquid jet instrument as in FIG. 14a.

DETAILED DESCRIPTION

Figure 1:
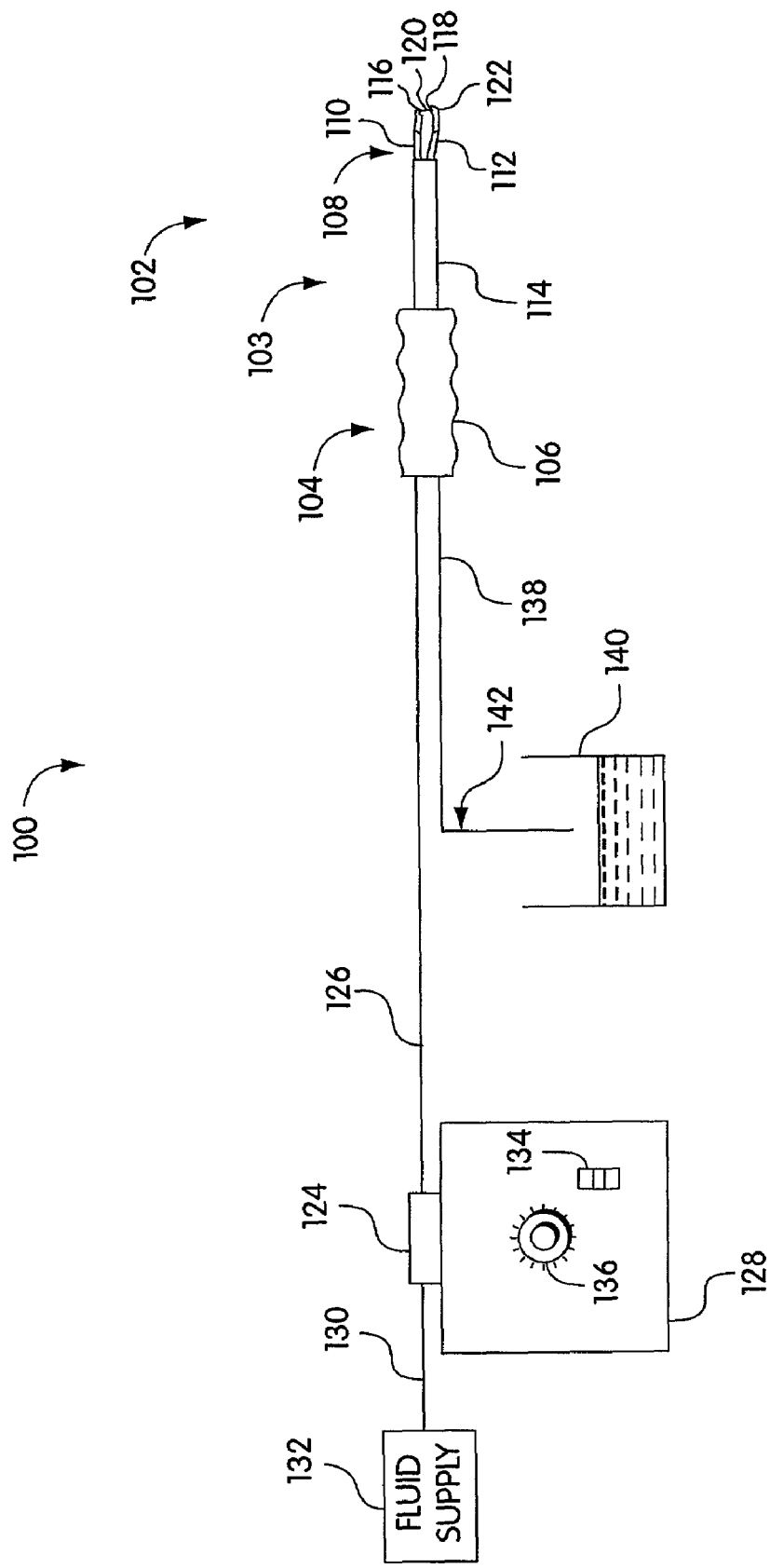
FIG. 1 is a schematic illustration of a surgical liquid jet system.

The present invention provides a variety of liquid jet instruments useful in a variety of applications, many of which are especially well suited for a variety of surgical procedures. The liquid jet instruments provided by the invention can be configured in a variety of different ways for use in various surgical operating fields. Preferred surgical instruments, according to the invention, are configured as surgical handpieces having a proximal end with a grasping region, or handle, shaped and configured to be comfortably held in the hand of an operator. The instruments also have a distal end that includes at least one nozzle for forming a liquid jet. The distal end of the inventive surgical instruments is utilized to perform a surgical procedure on a patient. Although the liquid jet instruments described herein are shown as having a handpiece configuration, it should be understood that the invention is not strictly limited to surgical handpieces, and that the invention may also be practiced utilizing liquid jet instruments having a variety of configurations and purposes. For example, instead of being configured as a surgical handpiece, the inventive liquid jet instrument could alternatively be configured as an elongated catheter for use in the vasculature of a patient, for example in thrombectomy procedures. In other embodiments, the inventive liquid jet instruments could be configured for manipulation by machine control, such as an X/Y/Z positioning machine. Also, the liquid jet instruments provided by the invention can be used in a wide variety of surgical applications to utilize a high pressure liquid stream to cut, drill, bore, perforate, strip, delaminate, liquefy, ablate, shape, or form various tissues, organs, etc. of the body of a patient.

The liquid jet surgical instruments provided by the invention include a pressure lumen, having a distal end terminating in at least one nozzle providing a liquid jet opening, and having a proximal end that is connectable to a source of liquid under high pressure, supplied, for example, by a high pressure pump or liquid dispenser. The liquid jet nozzle is shaped to form a liquid jet as a liquid under high pressure flows through the nozzle, as described below. The liquid jet, in preferred embodiments, can be used to cut, ablate, sculpt, trim, form, debride, etc., various tissues of a patient in surgical procedures. In preferred embodiments, the liquid pressure supplied to the instrument by the pump or dispenser is variably controllable by an operator of the instrument so that the cutting or ablating power of the liquid jet is adjustable by the operator. This adjustability of the pressure can allow an operator to create a liquid jet with the instrument that can differentiate between different types of tissue within a surgical operating field. For example, a lower pressure can be utilized for cutting or ablating a soft tissue such as fat from a surface of a harder tissue, such as muscle or bone, where the liquid jet has sufficient strength to cut or ablate the soft tissue without damaging the underlying harder tissue. A higher pressure can then be selected that is sufficient to form a liquid jet capable of cutting or ablating hard tissue, such as muscle or bone. In this way, a liquid jet surgical instrument provided by the invention can provide highly selective and controllable tissue cutting in various surgical procedures.

Preferred embodiments of the inventive surgical instruments also include a liquid jet target or deflector, which is locatable opposite the orifice in the nozzle from which the liquid jet is emitted (hereinafter referred to as the "liquid jet opening" or "jet opening") at a predetermined distance from the liquid jet opening in order to receive and/or deflect a liquid jet when the instrument is in operation. Embodiments including a target or deflector are preferred because the target/deflector prevents the liquid jet from being misdirected during use and potentially causing damage to unintended tissue sites in the surgical operating field. The target/deflector enables the instrument to provide a predetermined liquid jet length, defined by the predetermined distance between the liquid jet opening in the nozzle and the surface of the target/deflector upon which the liquid jet impinges. With such embodiments, the liquid jet can be utilized for performing surgical cutting or ablating of tissue without the danger of causing untended collateral damage to tissue lying beyond the target/deflector in the surgical operating field.

In some embodiments, the target/deflector can be simply a solid surface capable of deflecting and transforming the liquid jet into a harmless spray. In preferred embodiments, however, the target is defined by a jet-receiving opening included in an evacuation lumen that forms part of the surgical instrument. In the preferred embodiments including an evacuation lumen having a jet-receiving opening, in addition to providing a defined liquid jet length (defined by the predetermined distance between the liquid jet opening and the jet-receiving opening) and preventing unintended damage to surrounding tissue as discussed above, the evacuation lumen can also be utilized for removing liquid, ablated tissue, and debris from the surgical field with the instrument.

In some embodiments, an external source of suction, for example a vacuum pump or aspirator, can be provided in fluid communication with a proximal end of the evacuation lumen in order to provide the suction driving force required for evacuating material from the surgical field via the jet-receiving opening. In preferred embodiments, however, the invention provides surgical instruments having an evacuation lumen that is shaped and positionable relative to the jet nozzle (as will become apparent to those of ordinary skill in the art from the detailed description below) to enable evacuation of essentially all of the liquid comprising the liquid jet as well as ablated tissue and debris from the surgical site without requiring an external source of suction. In preferred embodiments, the evacuating force created by the liquid jet being directed into the evacuation lumen is sufficient to evacuate material from the operating site to a drainage reservoir located at the proximal end of the evacuation lumen or an evacuation conduit connected to the proximal end of the evacuation lumen. In such embodiments, the liquid jet and the evacuation lumen together act as an eductor pump, which utilizes the momentum and kinetic energy of the moving fluid of the liquid jet to create an evacuating force capable of driving the liquid, ablated material, and debris through the evacuation lumen and away from the surgical site.

As discussed in detail below, the invention teaches that effective evacuation of material through the evacuation lumen without the use of an external source of suction (i.e., via eductor pump action) requires the design of the inventive instruments to provide certain geometrical relationships between components relating, for example, the size of the jet-receiving opening in the evacuation lumen to the predetermined distance between the jet-receiving opening and the jet opening in the nozzle. Also, as taught by the invention, interrelated with the above-mentioned geometrical relationships in providing effective eductor-pump action is the design of the liquid jet nozzle, shape of the jet-receiving opening and distal end of the evacuation lumen, the angular orientation of the liquid jet with respect to the evacuation lumen, as well as the surrounding medium in which the surgical instrument is utilized. The present invention provides, in some embodiments, surgical instruments designed to account for some or all of the above-mentioned parameters to provide efficient evacuation, without the need for an external source of suction, for instruments having a wide variety of configurations and intended uses.

In one set of embodiments, the invention provides surgical liquid jet instruments constructed and arranged for use in a liquid surgical environment, where the liquid jet opening and the jet-receiving opening are both submerged in a liquid when the instrument is in operation. The meaning of "constructed and arranged for use in a liquid environment" as used herein refers to an inventive combination of structural features and geometric relationships between such features, which are specifically selected to provide improved performance of the instruments in a liquid environment, as will become readily apparent to those of ordinary skill in the art upon reading the detailed description below. Such devices can be configured as surgical handpieces for use, for example, in endoscopic, arthroscopic, or open surgery. As previously mentioned, such devices could also be configured as catheters for use in the vasculature of a patient.

Another class of surgical instruments provided by the invention are constructed and arranged for operation in a gaseous environment, such as in air, where the distal end of the instrument, including the fluid jet nozzle and jet-receiving opening, are essentially completely surrounded by gas when the instruments are in operation. The meaning of "constructed and arranged for operation in a gaseous environment" as used herein refers to an inventive combination of structural features and geometric relationships between such features, which are specifically selected to provide improved performance of the instruments in a gaseous environment, as will become readily apparent to those of ordinary skill in the art upon reading the detailed description below. Typical surgical procedures contemplated for using surgical instruments provided by the invention in gaseous environments involve procedures performed in a surrounding air environment, including, for example, surgical procedures on an external surface of a patient or certain open and minimally invasive surgical procedures. However, the surgical instruments designed for use in a gaseous environment provided by the invention are not limited for use in air but could be used when surrounded by any other gas, for example nitrogen, oxygen, carbon dioxide, mixtures thereof, etc.

The surgical liquid jet instruments designed for use in a gaseous environment that are provided by the invention can be advantageously utilized for a number of surgical procedures including certain open surgeries, laparoscopic surgeries, oral surgeries, and others. One preferred application of the inventive surgical liquid jet instruments for use in an air environment involves the use of such instruments on an external surface of the body of a patient for debriding wounds, burns, sites of infection, and other breaches of the human skin. The term "debriding" when used in this context refers to removal of a material from a surface via the liquid jet instrument. The material removed from the surface can, for example, comprise living tissue, dead tissue, foreign matter or debris embedded in the surface, infective material, etc. As will be discussed in greater detail below, preferred geometric relationships and design parameters, for providing efficient operation, for different components of the inventive surgical instruments differ for surgical instruments designed for use when submerged in a liquid and surgical instruments designed for use in a surrounding gaseous environment.

The inventive surgical liquid jet instruments, in preferred embodiments, can be configured to effectively remove material from a surgical site and transport the material through the evacuation lumen without the need for an external source of suction, for a wide variety of angular orientations between the central region of the liquid jet and the longitudinal axis of the evacuation lumen. The term "central region of the liquid jet" as used herein refers to a region defining the geometric center of the liquid jet. This region is typically an essentially cylindrical region of the liquid jet confined within a cylinder whose outer surface has a shape and perimeter defined by the inner circumference of the liquid jet opening, which circumference is projected from the liquid jet opening to the jet-receiving opening along an axis that is co-linear with the longitudinal axis of the jet nozzle. The "longitudinal axis" of the jet nozzle, as will be described in more detail below, is defined by the axial center line of the nozzle region of the pressure lumen. The "longitudinal axis" of the evacuation lumen refers to an axis defining the geometric center of the evacuation lumen in a region that is proximal to the jet-receiving opening. In typical embodiments, this region of the evacuation lumen will have a longitudinal axis that is essentially parallel to the longitudinal axis of the elongated body of the instrument, which is held and controlled by the hand of the operator (or, for embodiments involving configurations not including a body, such as a catheter configuration, the proximal end of the surgical instrument, not inserted into the patient, which is controllable by the operator). As used herein in the context of describing geometric relationships between longitudinal axes of various components, the term "co-linear" refers to components whose longitudinal axes are superimposed on essentially the same line in space. The term "parallel" when used in the same context herein refers to longitudinal axes that are not co-linear, but that are oriented in an essentially identical direction in space. Accordingly, the surgical instruments provided by the invention enable effective evacuation of material and debris from the surgical site, without the need for an external source of vacuum, for a wide variety of liquid jet angular configurations, including instruments providing liquid jets that are directed axially, transversely, or at any angle between 0 and 180° with respect to a longitudinal axis defining the proximal end, or body, of the surgical instrument. Such flexibility allows the inventive surgical instruments to be designed having a distal end that has a variety of predetermined contours, shapes, and sizes specifically selected for particular surgical procedures. Such customization of the instruments allows the liquid jet instruments to be designed and configured to facilitate and reduce the difficulty of insertion of the distal end of the device into confined regions of the body defining a surgical operating space. For example, as will be discussed in greater detail below, the invention provides surgical liquid jet instruments and a surgical method for performing arthroscopic surgical procedures, or other surgical procedures, in joint capsules of a patient, for example in the knee.

To further facilitate insertion of the inventive surgical liquid jet instruments into confined surgical operating spaces, in a number of preferred embodiments, especially involving instruments designed for operation when submerged in a liquid environment, the invention provides surgical instruments having deployable distal ends. The term "deployable" as used herein refers to a surgical liquid jet instrument having a distal end where either the pressure lumen, the evacuation lumen, or both are moveable relative to each other in order to vary the predetermined distance between the liquid jet opening in the nozzle and the jet-receiving opening in the evacuation lumen. Typically, such instruments are inserted into the operating site in an undeployed configuration, where in the undeployed configuration the predetermined distance mentioned above is small or essentially zero and the distal end of the instrument has a minimum cross-sectional dimension for insertion. After insertion, the operator can, by manipulating the proximal end or body of the instrument, deploy the distal end to provide the desired predetermined distance between the jet opening and the jet-receiving opening and, thus, the desired liquid jet length. As described in more detail below, the deployment can involve, for example, a longitudinal movement of one or both of the lumen with respect to the proximal end or body of the instrument, a lateral movement of one or both of the lumen, a rotational movement of one or both of the lumen, or a combination of any of the above, so long as the movement involves a change in the predetermined distance between the liquid jet opening and the jet-receiving opening.

As will be described in more detail below, in some preferred embodiments, the proximal end of the instrument comprises a body with a grasping region for an operator. The body can include at least one actuating element that can be manipulated by an operator to cause a pre-determined change in a function, shape, position, or orientation of at least a portion of the distal end of the instrument upon actuation. For example, the actuating element(s) can be used to deploy the distal end of the instrument. For embodiments including two or more actuating elements according to the invention, the actuating elements preferably cause an essentially identical pre-determined change in a function, shape, position, or orientation of at least a portion of the distal end of the instrument upon actuation, as described in greater detail below. In some preferred embodiments, the actuating element(s) can be positioned to be easily actuated by a single hand of an operator for at least two different hand/grasping region orientations, thus permitting the operator to hold the instrument in at least two distinct positions within her hand while still being able to actuate the actuating element(s).

The inventive liquid jet surgical instruments advantageously include distal ends that are designed and configured, for some embodiments, to prevent or reduce plugging of the evacuation lumen, blow-by of the liquid jet, or back spray or misting of the liquid jet when the instrument is in operation. "Blow-by" of the liquid jet, as used herein, refers to a portion of the liquid jet, or a high velocity fluid entrained by the liquid jet (comprising the "entrainment region" as discussed below), having a cross-sectional area, at the plane of the jet-receiving opening, that is larger than the cross-sectional area of the jet-receiving opening so that at least a portion of the liquid jet or high velocity fluid misses or "blows by" the jet-receiving opening. Blow-by is generally undesirable because it can lead to unintended tissue damage and poor evacuation efficiency. "Back spray" as used herein refers to a liquid jet, or high velocity fluid entrained by the liquid jet, entering the jet-receiving opening in the evacuation lumen and subsequently reflecting or flowing back into the surgical field from the jet-receiving opening. Such back spray is undesirable in operation due to the potential of contamination of the surgical operating field and/or aerosolization of infective material, in addition, back spray typically indicates a poor efficiency level of the evacuation of material by the instrument via eductor pump action. As described in more detail below, the surgical instruments provided by the invention substantially reduce, and in preferred embodiments essentially eliminate, performance problems associated with blow-by and back spray when the instruments are in operation.

Plugging of the evacuation lumen can be prevented, for embodiments involving surgical instruments designed for operation in a liquid environment, by constructing the evacuation lumen to have a region that is within and/or downstream of the jet-receiving opening that is designed to be able to macerate at least a portion of the tissue entrained by the liquid jet into a plurality of particles when the instrument is in operation. The term "macerate" as used herein refers to a disaggregation of entrained material, for example an entrained tissue, by a liquid within the evacuation lumen undergoing intensely turbulent flow that creates a region of extremely high fluid shear and impacting forces capable of partitioning the material into particles having a size small enough to pass through the evacuation lumen without plugging the lumen. In preferred embodiments, the evacuation lumen is able to macerate a substantial fraction of the tissue entrained into a plurality of essentially microscopic particles. "Microscopic" as used herein refers to particles having a dimension too small to be visualized unaided by the human eye. Prevention of blow-by and back spray can be accomplished by providing a surgical liquid jet instrument having a distal end configured so that when in operation, the liquid jet and the high velocity fluid entrained by the liquid jet occupies a substantial fraction of the cross-sectional area of the jet-receiving opening, but does not occupy a region larger than the cross-sectional area of the jet-receiving opening. As discussed in more detail below, this "substantial fraction" refers to at least 50%, but less than 100% of the cross-sectional area of the jet-receiving opening being occupied by an entrainment region created by the liquid jet.

The inventive surgical liquid jet instruments will now be described in more complete detail in the context of several specific embodiments illustrated in the appended figures. It is to be understood that the embodiments described are for illustrative purposes only and that the novel features of the invention, as described in the appended claims, can be practiced in other ways or utilized for instruments having other configurations, as apparent to those of ordinary skill in the art.

FIG. 1 shows one embodiment of a liquid jet surgical system 100 utilizing a liquid jet surgical instrument 102, according to the invention. The surgical instrument 102 illustrated is configured as a surgical handpiece having a proximal end 103 including a body 104 having a grasping region 106 configured for placement in the hand of an operator of the instrument. The surgical instrument 102 has a distal end 108 including a pressure lumen 110 and an evacuation lumen 112. "Distal end" when used herein in the context of a region of a surgical instrument refers to the portion of the surgical instrument that is adapted to perform a surgical procedure on a patient, and which is inserted into a surgical site during operation of the instrument. The distal end of the instrument 108 can, in some embodiments, comprise only the distal ends of pressure lumen 110 and evacuation lumen 112, or in other embodiments, can include components proximal to the distal ends of the pressure lumen 110 and the evacuation lumen 112 that are also inserted into a surgical operating space of the patient during use of the instrument.

In the illustrated embodiment, surgical instrument 102 further includes a sheath 114, which at least partially surrounds pressure lumen 110 and evacuation lumen 112 and supplies support for the lumen to assists in maintaining and/or establishing a desired geometric configuration between pressure lumen 110 and evacuation lumen 112, when the instrument 102 is in operation. Pressure lumen 110 further includes at its distal end a nozzle 116, which forms a liquid jet as a high pressure liquid supplied by pressure lumen 110 streams therethrough. Evacuation lumen 1 12 includes a jet-receiving opening 118 located at its distal end and positioned, when the instrument 102 is in operation, opposite the jet nozzle 116 at a predetermined distance therefrom in order to receive the liquid jet 120.

In the particular embodiment illustrated, liquid jet 120 is directed transversely (e.g., at an angle of approximately 90°) with respect to the longitudinal axes of the evacuation lumen 112 and the body 104 of the instrument 102. As will be explained in more detail below, for such embodiments, the evacuation lumen 112 preferably includes a jet-deflecting portion 122 downstream and adjacent to the jet-receiving opening 118 that is utilized to deflect and direct the liquid entering the jet-receiving opening 118 proximally within evacuation lumen 112. Pressure lumen 110 and evacuation lumen 112 are preferably constructed from a surgical grade stainless steel, however, in alternative embodiments, either or both of the lumen may be constructed from other suitable materials, for example certain polymeric materials, as apparent to those of ordinary skill in the art. Regardless of the specific material from which the pressure lumen is constructed, pressure lumen 110 must have sufficient burst strength to enable it to conduct a high pressure liquid to nozzle 116 in order to form liquid jet 120. The burst strength of pressure lumen 110 should be selected to meet and preferably exceed the highest contemplated pressure of the liquid supplied for use in the specific surgical procedure to be performed. Typically, surgical instrument 102 will operate at liquid pressure between about 500 psig and about 50,000 psig, depending on the intended material to be cut and/or ablated. Those of ordinary skill in the art will readily be able to select appropriate materials for forming pressure lumen 110 and evacuation lumen 112 for particular surgical requirements.

In preferred embodiments, pressure lumen 110 and evacuation lumen 112 are constructed and supported so that the distal ends of the lumens are sufficiently stiff to prevent deflection of the lumens by, for example, contact with surfaces within the surgical operating space, which deflection could potentially lead to misdirection of liquid jet 120 so that it is no longer incident upon jet-receiving opening 118, thus potentially causing unintended tissue damage to the patient. Pressure lumen 10 is in fluid communication with high pressure pump 124 via high pressure liquid supply conduit 126. High pressure liquid supply conduit 126 must also have a burst strength capable of withstanding the highest liquid pressures contemplated for using the instrument 102 for a particular surgical application. In some embodiments, high pressure liquid supply conduit 126 comprises a burst-resistant stainless steel hypotube constructed to withstand at least 50,000 psig. In some embodiments, the hypotube may be helically coiled to improve the flexibility and maneuverability of the surgical instrument 102. In preferred embodiments, high pressure liquid supply conduit 126 comprises a Kevlar reinforced nylon tube that is connectable to the pressure lumen 110.

In fluid communication with high pressure liquid supply conduit 126 is a high pressure pump 124, which can be any suitable pump capable of supplying the liquid pressures required for performing the desired surgical procedure. Those of ordinary skill in the art will readily appreciate that many types of high pressure pumps may be utilized for the present purpose, including, but not limited to, piston pumps and diaphragm pumps. In preferred embodiments, high pressure pump 124 comprises a disposable piston or diaphragm pump, which is coupled to a reusable pump drive console 128. High pressure pump 124 has an inlet that is in fluid communication with a low pressure liquid supply line 130, which receives liquid from liquid supply reservoir 132. Pump drive console 128 preferably includes an electric motor that can be utilized to provide a driving force to high pressure pump 124 for supplying a high pressure liquid in liquid supply conduit 126.

While a variety of known pump consoles may be utilized in the context of the present invention, the preferred pump drive console includes a constant speed electric motor that can be turned on and off by means of an operator-controlled switch 134. In preferred embodiments, operator-controlled switch 134 comprises a foot pedal or a button or trigger located on grasping region 106 of the surgical instrument 102 that may be easily accessed by the operator of the instrument. In some embodiments, pump drive console 128 can have a delivery pressure/flow rate that is factory preset and not adjustable in use. In other embodiments, the pressure/flow rate may be controlled by the operator via an adjustable pressure/flow rate control component 136, that can control the motor speed of the pump drive console and/or the displacement of the high pressure pump. While in FIG. 1, pressure/flow rate control component 136 is illustrated as a knob on pump drive console 128, in preferred embodiments, such component would preferably comprise a foot pedal, or trigger/button located on grasping region 106, as previously discussed for on/off control of the pump drive console 128. In yet other embodiments, pump drive console 128 and high pressure pump 124 may be replaced by a high pressure liquid dispenser or other means to deliver a high pressure liquid, as apparent to those of ordinary skill in the art.

The liquid utilized for forming the liquid cutting jet can be any fluid that can be maintained in a liquid state at the pressures and temperatures contemplated for performing the surgical procedures. For applications in which the instruments are used to perform surgical procedures in a live patient, the liquid utilized should also be physiologically compatible. In typical embodiments, the liquid supplied will be a sterile surgical saline solution, or sterile water and liquid supply reservoir 132 can comprise a sterile container, such as an intravenous (IV) bag containing such fluid. In some embodiments, in order to improve the cutting or ablating character of the liquid jet, the liquid may contain solid abrasives, or the liquid may comprise a liquefied gas, for example carbon dioxide, which forms solid particulate material upon being admitted from nozzle 116 to for the liquid jet 120. In other embodiments, the liquid supplied to surgical instrument 102 may include medicaments, such as antiseptics, antibiotics, antiviral components, anesthetics, drugs, chemotherapy agents, etc., that are useful in the context of a specific surgical procedure. In other embodiments, the fluid may include a dye to improve visualization of the liquid jet when the instrument is in operation.

Evacuation lumen 112 is connectable at its proximal end to an evacuation conduit 138, which can be used to transport evacuated material and debris to a drainage reservoir 140. The liquid contained in evacuation conduit 138 is under relatively low pressure and, accordingly, evacuation conduit 138 may be constructed, in preferred embodiments, of a low cost flexible material, for example, polymeric tubing, such as polyvinyl chloride (PVC), silicone, polyethylene, rubber, etc. tubing. In preferred embodiments, evacuation conduit 138 should have a minimum internal cross-sectional area that equals or exceeds the maximum internal cross-sectional area of evacuation lumen 112. In the illustrated embodiment, surgical instrument 102 is constructed such that evacuation lumen 112 is capable of evacuating liquid jet 120 and ablated material and debris from the jet-receiving opening 118 to the proximal end of evacuation lumen 112 and through evacuation conduit 138 into drainage reservoir 140, without the need for an external source of suction. In such embodiments, it is preferred that evacuation conduit 138 include a vacuum breaker 142 or a proximal end that is not couplable to an external source of suction, so that it is not possible for an operator to inadvertently couple evacuation conduit 138 to an external source of suction when the instrument is in operation.

In preferred embodiments, the fluid supply path of liquid jet surgical system 100 is disposable, and sterilizable, for example by chemical methods such as exposure to ethylene oxide, or by gamma or beta irradiation, as apparent to those of ordinary skill in the art. In especially preferred embodiments, the fluid path is supplied pre-sterilized to the user for a single use only. Those of ordinary skill in the art understand what is meant by "disposable" and "for a single use only." Disposability of the liquid supply path, including liquid supply reservoir 132, liquid supply line 130, high pressure pump 124, high pressure liquid supply conduit 126, and pressure lumen 110 is advantageous because such components can be difficult to effectively clean and sterilize between use without reducing the utility of the instrument, for example by the plugging of jet nozzle 116 with deposits during the sterilization process. In especially preferred embodiments, all of the components of liquid jet surgical system 100 are entirely disposable after a single use except for pump drive console 128. For embodiments where the surgical liquid jet instrument is disposable after a single use, the instrument is preferably sterilizable, and most preferably provided pre-sterilized. In other embodiments, only the pressure lumen and the distal end of the instrument for insertion into the patient are sterilizable or pre-sterilized.

Grasping region 106 may be configured in a wide variety of shapes and configurations depending on the ergodynamics of a particular surgical operating procedure and/or the preference of a particular operator. For example, as opposed to the grasping region 106 illustrated, which comprises an elongated handle, the grasping region may be formed in the shape of a pistol, or with loops, straps, rings, finger slots, etc., as apparent to those of ordinary skill in the art.

Figure 2A:
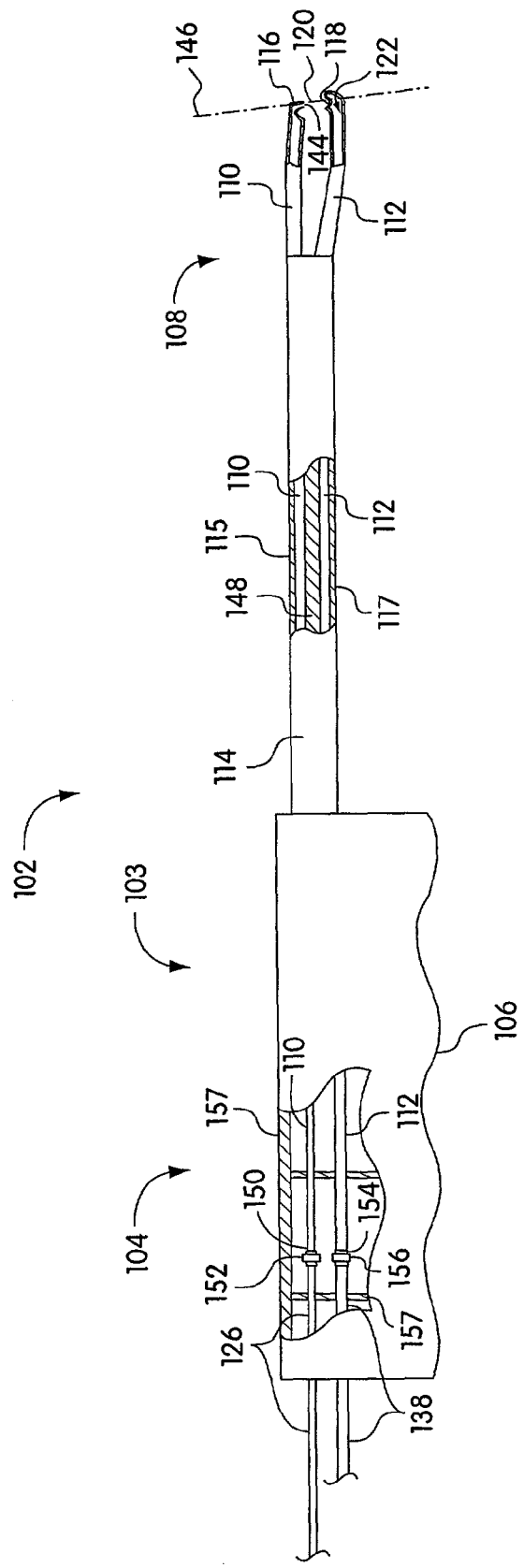
FIG. 2a is a partially-cutaway schematic illustration of a surgical liquid jet instrument.

Surgical instrument 102 is shown in greater detail in FIG. 2a. Specifically, FIG. 2a shows partially cutaway views of body 104 of surgical instrument 102, sheath 114, pressure lumen 110 and evacuation lumen 112. Now more clearly visible is jet opening 144 located at the outlet of nozzle 116, which jet opening 144 defines the apex of liquid jet 120 as it is emitted from nozzle 116. Also more clearly visible are the jet-receiving opening 118 and jet-deflecting portion 122 of evacuation lumen 112. In the illustrated embodiment, liquid jet 120 is directed into jet-receiving opening 118 such that the axis 146 defining the direction of the central region of liquid jet 120 is essentially perpendicular to the longitudinal axis of sheath 114 and the proximal end 103 of surgical instrument 102.

Sheath 114 can comprise a tube that is attached at its proximal end to the body 104 of surgical instrument 102 and which includes two channels therewithin. Through one channel 115 traverses pressure lumen 110 and through the other channel 117 traverses evacuation lumen 112. The channels 115, 117 through which the lumen 110, 112 traverse are separated by a central spacer region 148. Sheath 114 may be constructed from a variety of known materials, as apparent to those of ordinary skill in the art. In preferred embodiments, sheath 114 is constructed of a surgical grade stainless steel. In alternative embodiments to that shown, sheath 114 may comprise a simple tube without central region 148, and the pressure lumen and evacuation lumen may be disposed within the sheath, such that they are in direct contact with each other along the length of the sheath. Such an embodiment is preferred for devices where a minimal cross-sectional dimension of the distal end of the instrument is desirable.

Pressure lumen 110 and/or evacuation lumen 112 may be rigidly connected to the sheath 114 in one or more locations along the length of the sheath, for embodiments where the lumen are immobile with respect to the sheath. In alternative embodiments, to be discussed in more detail below, at least one of the lumen may be slidable and/or rotatable within the sheath. The lumen may be immobilized within sheath 114 via a variety of methods, for example, by simple friction between the walls of the lumen and the inner surface of one or more portions of sheath 114, by welding, gluing, press fitting, or other methods of affixing an outer surface of a lumen to an inner surface of the sheath, or by any other methods apparent to those of ordinary skill in the art. In alternative embodiments to that shown in FIG. 2a, sheath 114 may be eliminated entirely. In such embodiments, the pressure lumen and evacuation lumen may be directly connected to each other, for example, by welding, gluing, etc., or may be coupled to each other via straps, rings, clips, or other means apparent to those of ordinary skill in the art.

The cutaway region shown of body portion 104 of surgical instrument 102 shows the connection between pressure lumen 110 and high pressure liquid supply conduit 126, and the connection between evacuation lumen 112 and evacuation conduit 138, according to one embodiment. Proximal end 150 of pressure lumen 110 is coupled to high pressure liquid supply conduit 126 via high pressure tubing coupler 152. High pressure tubing coupler 152 can comprise a stainless steel barbed fitting including, in some embodiments, a crimped sleeve disposed over the barbed fitting to hold the ends of the pressure lumen 110 and high pressure liquid supply conduit 126 securely in place when under pressure. In alternative embodiments, the high pressure tubing coupler can be secured to the ends of the pressure lumen and the high pressure liquid supply conduit by means of an epoxy adhesive or other sealant as apparent to those of ordinary skill in the art. As opposed to the essentially permanent connections described immediately above, in alternative embodiments, the high pressure tubing coupler may comprise a high pressure detachable or uncouplable element, such as a variety of high pressure tubing fittings known to those of ordinary skill in the art. Similarly, the proximal end 154 of evacuation lumen 112 can be coupled to evacuation conduit 138 via a low pressure tubing coupler 156. Low pressure tubing coupling element 156 can comprise any of a variety of low pressure tubing fittings known in the art, including but not limited to, barbed fittings, Leur-lock fittings, etc. Preferably, low pressure coupling element 156 has a minimum internal cross-sectional area that is at least as great as the maximum internal cross-sectional area of evacuation lumen 112. The pressure lumen 110, evacuation lumen 112, high pressure liquid supply conduit 126, and evacuation conduit 138 are supported and positioned within body 104 via support elements 157, which can comprise an extension or protrusion from an internal surface of body 104 having slots, grooves, or holes therein through which the lumen/conduits pass.

Figure 2B:
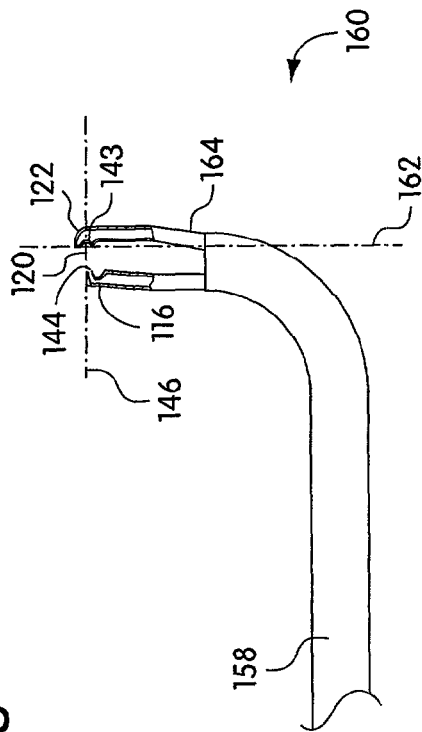
FIG. 2b is a partially-cutaway schematic illustration of a portion of a surgical liquid jet instrument, the portion including the distal end of the surgical liquid jet instrument.

FIG. 2b shows an alternative embodiment of a sheath and distal end of a surgical instrument having a sheath 158 that is not straight as above, but instead is curved at the distal end 160 of the instrument. Such a configuration may be advantageous for reducing the difficulty of insertion of the distal end 160 of the instrument in certain surgical spaces. Sheath 158 provides an orientation of nozzle 116 and jet-receiving opening 143 such that the axis 146 defining the direction of the central region of liquid jet 120 emitted from jet opening is essentially parallel to the longitudinal axis of the proximal end of sheath 158 and the proximal end of the instrument. In the illustrated embodiment the central region of liquid jet 120 is directed at an angle of about 180° with respect to a longitudinal axis of a proximal end of the instrument, to which sheath 158 is connected, and at an angle of about 90° with respect to the longitudinal axis 162 of evacuation lumen 164 in a region proximal to the curved, jet-deflecting portion 122 of evacuation lumen 164.

Figure 3A:
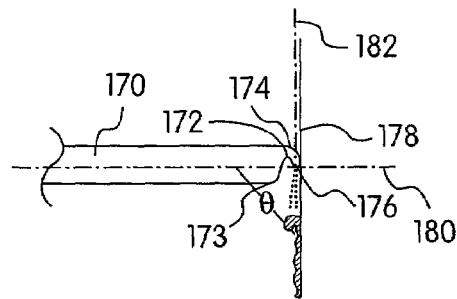
FIG. 3a is a schematic illustration of a portion of a pressure lumen of a surgical liquid jet instrument.

FIGS. 3a–3d show a variety of embodiments for the distal region of the pressure lumen providing the liquid jet nozzle and jet opening. FIG. 3a shows the distal region of one embodiment of a pressure lumen, which is preferred for use in surgical instruments that are designed to be utilized in a liquid environment. Pressure lumen 170 comprises a tubular conduit having a necked region 172 of the conduit defining nozzle 174, which necked region has an internal cross-sectional area that is less than an internal cross-sectional area of the tubular conduit outside of and proximal to necked region 172. The distal end of pressure lumen 170 is further configured to enable jet opening 176 to be positioned adjacent to a surface 178 to be ablated or debrided by the surgical instrument, such that a liquid jet emanating from jet opening 176 is separated from surface 178 by a distance that is essentially equal to a wall thickness of the tubing comprising nozzle 174 at the region of jet opening 176. Nozzle 174 can be formed in pressure lumen 170 by methods described below, and enables an operator of the surgical instrument including pressure lumen 170 to position nozzle 174 adjacent, or in close proximity to, a surface 178 to be ablated or debrided and to direct a liquid jet essentially parallel to surface 178 at a very small distance therefrom. Nozzle region 174 is bent with respect to the axial center line 180 of pressure lumen 170 outside jet nozzle region 174 so that jet opening 176 emits a liquid jet whose central region is directed along an axis 182 that forms an angle θ with respect to axis 180. Angle θ can be any angle between about 0 and about 90 degrees and, in preferred embodiments, is an angle of about 90 degrees.

The nozzle shown in FIG. 3a also advantageously provides a transversely-directed liquid jet and a relatively large nozzle length to internal diameter ratio, while simultaneously providing a small profile for pressure lumen 170 due to the fact that the nozzle 174 does not project radially beyond a parameter defined by the outer surface of the tubular conduit forming the pressure lumen 170 in the region 173 that is adjacent and proximal to necked region 172. Nozzle 174, when utilized for surgical instruments for use in a liquid environment, preferably has a region having a minimum internal diameter, where the region has a length that exceeds its minimal internal diameter by at least a factor of about four, more preferably by at least a factor of about six. In other embodiments, the region has a length that exceeds its minimal internal diameter by at least a factor of about ten. As will be discussed in more detail below, the greater the ratio of the length to minimum internal diameter of the nozzle region, the more narrowly focused and collimated is the liquid jet that is emitted from jet opening 176. For reasons described in more detail below, highly collimated liquid jets are generally preferred for embodiments involving surgical instruments for use in liquid environments; however, in general, nozzles with ratios of length to minimum internal diameter that are very high, for example greater than about ten, tend to create a very high pressure drop through the nozzle during use without significantly improving the degree of collimation of the jet and, therefore, are less preferred than nozzles having a ratio of length to minimum internal diameter of an intermediate value, for example about six.

Figure 3C:
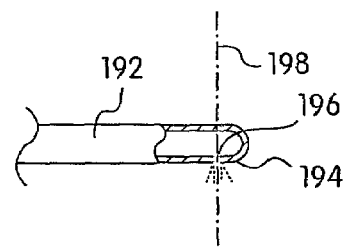
FIG. 3c is a partially-cutaway schematic illustration of a portion of a pressure lumen of a surgical jet instrument.
Figure 3B:
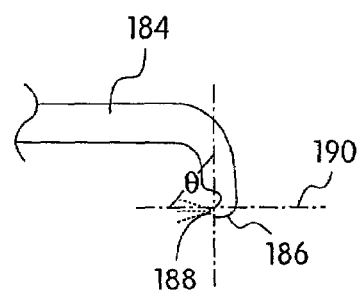
FIG. 3b is a schematic illustration of a portion of pressure lumen of a surgical liquid jet instrument.

FIG. 3b shows the distal portion of pressure lumen 184 providing a nozzle 186 that is similar in configuration to nozzle 174 shown in FIG. 3a. Pressure lumen 184, however, is curved near its distal end so that jet opening 188 emits a liquid jet having an axis 190 defining the direction of its central region, which would be essentially parallel to a longitudinal axis of the proximal end of the surgical liquid jet instrument to which pressure lumen 184 is connected. In addition to the illustrated embodiments shown in FIGS. 3a and 3b, those of ordinary skill in the art would readily appreciate that the pressure lumen and nozzle can be shaped and positioned to provide liquid jets directed in a wide variety of desired angular orientations with respect to the longitudinal axis of the proximal end or body of the surgical instrument.

FIG. 3c shows an alternative embodiment for forming a liquid jet nozzle in a pressure lumen. Nozzle region 194 in pressure lumen 192 comprises a hole that is drilled or bored into a sidewall of the tubing comprising pressure lumen 192. Nozzle 194 provides a jet opening 196 that directs a fluid jet so that the central region of the liquid jet is collinear to an axis 198 that is essentially transverse to the longitudinal axis of pressure lumen 192. The embodiment shown in FIG. 3c is well suited for use in surgical instruments where a low profile pressure lumen that provides a nozzle region having a length to minimum internal cross-sectional diameter ratio that is relatively small is desired. As will be discussed in greater detail below, nozzles having relatively low length to minimum internal diameter ratios are generally preferred for surgical instruments designed for utilization in a surrounding gaseous environment. Nozzle region 194 will have a length that comprises essentially a wall thickness of pressure lumen 192 in the region adjacent to the nozzle 194. The size of jet opening 196 can be selected with respect to the thickness of pressure lumen 192 to provide the desired length to minimum internal diameter ratio for nozzle 194. For embodiments involving surgical instruments designed for utilization in a gaseous environment, the preferred length to minimum internal diameter ratio of nozzle 194 is not greater than about four, and more preferably is not greater than about two. As opposed to nozzles having relatively large length to minimum internal diameter ratios, which typically emit a relatively focused and collimated liquid jet as a high pressure liquid streams through the nozzle, nozzles having a lower length to minimum internal diameter ratio typically emit a liquid jet that is less collimated and more diverging in character, as shown in FIG. 3e.

Figure 3D:
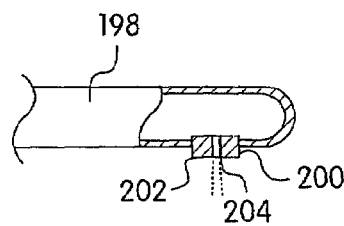
FIG. 3d is a partially-cutaway schematic illustration of a portion of a pressure lumen of a surgical liquid jet instrument.
Figure 3E:
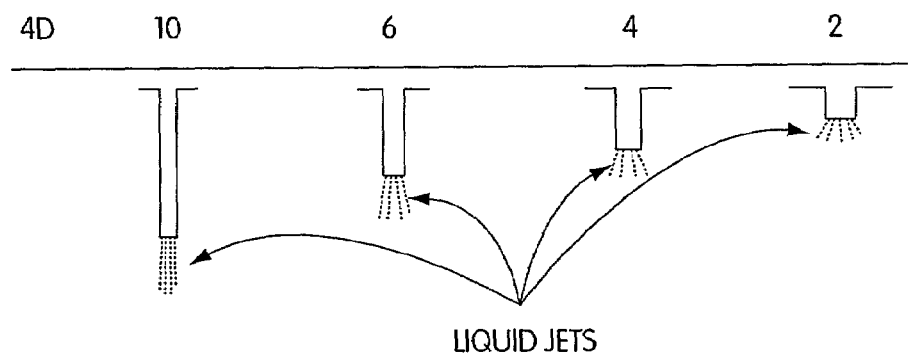
FIG. 3e is a schematic illustration of a variety of liquid jet nozzles having various length to minimum diameter ratios.

FIG. 3d shows yet another embodiment for providing a nozzle in a pressure lumen. Similar to FIG. 3c above, pressure lumen 198 in the illustrated embodiment includes a hole that is bored into a sidewall of tubing comprising the pressure lumen. Unlike the embodiment shown above is FIG. 3c, and in order to provide a nozzle 202 having an increased length to minimum internal diameter ratio, pressure lumen 198 includes a nozzle insert 200 that is sealingly inserted into the bore formed in the sidewall of the lumen. Nozzle insert 200 can include a channel 204 formed therein having a desired predetermined minimum internal diameter to provide a desired nozzle length to internal diameter ratio, which can generally exceed the nozzle length to diameter ratio possible for a nozzle formed as in FIG. 3c above.

Nozzle insert 200 may be formed from the same material as pressure lumen 198, for example stainless steel, or may be formed from a variety of other materials having a hardness level that exceeds the material utilized for forming pressure lumen 198. For example, nozzle insert 200 may be made entirely, or at least in part, from a metal such as titanium, tungsten, vanadium, or other high hardness metals, or from a crystalline non-metallic material, such as sapphire, diamond, etc., as apparent to those of ordinary skill in the art. In alternative embodiments, instead of providing a nozzle insert as shown, the evacuation lumen may be provided with a region of the sidewall having a wall thickness exceeding that of the wall thickness outside the region. The nozzle, in such embodiments, can be formed by providing a hole through the region having an increased wall thickness.

Figure 4:
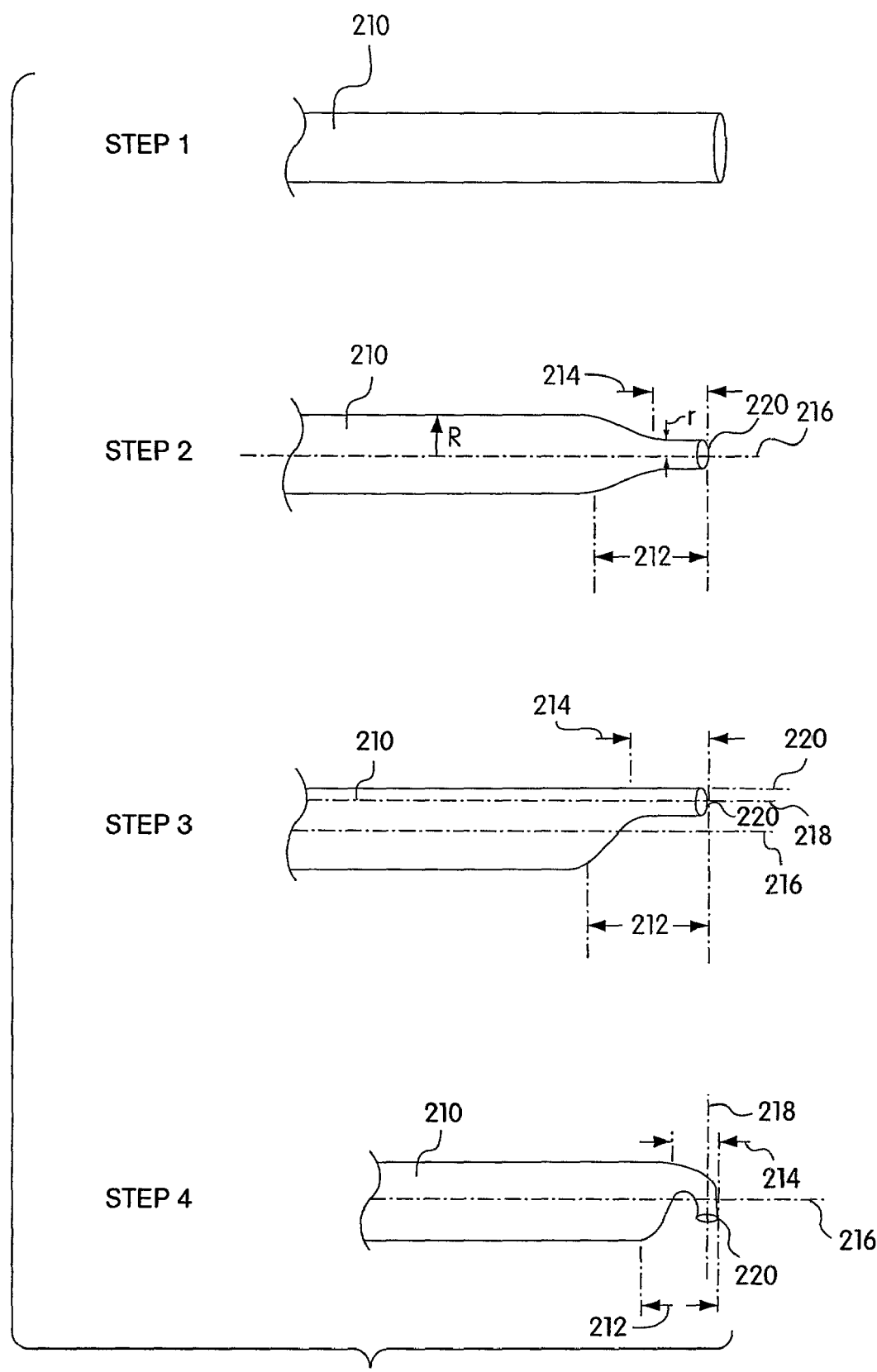
FIG. 4 is a series of schematic illustrations illustrating a method for forming a liquid jet nozzle region.

FIG. 4 illustrates a preferred method, according to the invention, for forming the nozzles described above in FIGS. 3a and 3b. Step 1 of FIG. 4 entails providing a tubular conduit 210 for use in forming a pressure lumen. As described above, the tubular conduit is typically formed of a biocompatible metal such as surgical stainless steel and is selected to have a burst strength sufficient to withstand the contemplated liquid pressures (e.g., a burst strength of at least 50,000 psig).

Step 2 of the method comprises necking down an end of conduit 210 to form a necked region 212 having a reduced cross-sectional area, which necked region tapers into a jet nozzle region 214 having an essentially constant internal cross-sectional area. Jet nozzle region 214 terminates at its distal end in jet opening 220. Necked region 212 can be formed in conduit 210 by a variety of means known in the art, for example by swaging, crimping, or hot-drawing the distal end of conduit 210 to form necked region 212 and jet nozzle region 214. At the end of Step 2, pressure lumen conduit 210 has an internal radius R, jet nozzle region 214 has a minimum internal radius r, and jet nozzle region 214 is essentially co-linear with the axial center line 216 of the tube comprising the pressure lumen 210 outside of necked region 212.

Step 3 of the method involves offsetting jet nozzle region 214 with respect to tube 210 so that the axial center line 218 of nozzle region 214 is offset from the axial center line 216 of tube 210 outside of necked region 212, by a distance $D=R-r$, so that the jet nozzle region 214 and the tubular conduit 210 abut each other along at least one line 220 co-linear to an external surface of tubular conduit 210.

For embodiments where it is desired that at least a central region of the liquid jet emitted from jet opening 220 be directed in an orientation that is not parallel with axis 216, jet nozzle region 214 may be bent with respect to axis 216 as shown in optional Step 4. In typical embodiments, nozzle region 214 is bent so that the axial center line 218 of jet nozzle region 214 forms an angle with respect to axis 216 that is between 45 and 115 degrees, more typically between about 80 and 100 degrees, and most typically about 90 degrees. Also preferably nozzle region 214 is bent with respect to tube 210 so that essentially no portion of jet nozzle region 214 projects radially beyond a perimeter that is defined by an outer surface of tube 210 outside of necked region 212. In addition to providing a method for forming liquid jet nozzles that have a relatively large length to minimum diameter ratio and that are relatively easy and inexpensive to manufacture, the inventive method also provides a pressure lumen having a maximum cross-sectional profile that does not exceed the diameter of the tubing comprising the pressure lumen. In addition, the nozzles formed by the method outlined in FIG. 4 also advantageously provide improved efficiency for forming a liquid jet as a high pressure liquid streams through the nozzle. The efficiency of forming the liquid jet is improved over nozzle designs comprising, for example, a hole bored in the side of a lumen, due to the fact that necked region 212 provides a smooth tapering flow path for the liquid flowing into nozzle region 214, thus reducing turbulence, recirculating flow patterns, and friction at the jet nozzle inlet. This effect is known in the fluid mechanical arts as the "vena contracta" effect and can improve fluid flow efficiencies through nozzles by as much as 30%.

The present invention provides surgical liquid jet instruments which are specifically designed and constructed for use in a particular surgical environment. Specifically, in some embodiments, the present invention provides surgical liquid jet instrument designs that are tailored to provide highly desirable performance characteristics in surgical operating environments where the liquid jet is submerged in a liquid environment when the instrument is in operation, and, in other embodiments, the present invention provides surgical liquid jet instrument designs that are tailored to provide highly desirable performance characteristics in surgical operating environments where the liquid jet is surrounded by a gaseous environment when the instrument is in operation. More specifically, the invention provides surgical liquid jet instruments including pressure lumen and evacuation lumen that are shaped, and positioned relative to each other, to establish certain predetermined geometric relationships between the jet forming components and jet-receiving components that are specifically selected to provide the desired performance characteristics of the instrument in a liquid or gaseous surgical environment. Importantly, the above mentioned geometric relationships and design characteristics are substantially different for instruments that are designed for use in a liquid environment when compared to instruments that are designed for use in a gaseous environment.

Reference is made in FIG. 5a for describing the operation and design characteristics of preferred devices for use in forming a liquid jet that is submerged in a surrounding liquid-containing surgical environment. FIG. 5a shows a partially cutaway view of the distal ends of pressure lumen 230 and evacuation lumen 240, which can form part of a surgical instrument, for example such as that shown previously in FIG. 2a. Prior to operation, the distal ends of pressure lumen 230 and evacuation lumen 240 would be inserted into the operating field and at least partially submersed in a liquid 244 therein so that at least nozzle 232 and jet-receiving opening 234 are completely surrounded by liquid 244. When the instrument is in operation, liquid under high pressure is delivered via pressure lumen 230 to nozzle 232, causing jet opening 236 to create a liquid jet 238 as the high pressure liquid streams therethrough. As mentioned previously, for embodiments where the liquid jet 238 is formed in a surrounding liquid environment 244, it is preferred that the jet 238 is substantially collimated as it exits jet opening 236. The more collimated a liquid jet, the less the liquid jet will diverge or disperse as it traverses the gap between jet opening 236 and jet-receiving opening 234. Thus, a highly collimated jet will have a cross-sectional shape and area at the jet-receiving opening 234 that is substantially similar to the cross-sectional shape and area of the liquid jet at jet opening 236.

As discussed previously, the pressure of the high pressure liquid supplied to nozzle 232 for forming the liquid jet 238 depends on the particular design of nozzle 232 and the hardness/toughness of tissue or material to be cut or ablated.

Typically, the liquid at high pressure is supplied to jet opening 236 at a pressure of at least 500 psig, in other embodiments at a pressure of at least about 5,000 psig, and still other embodiments at a pressure of at least about 15,000 psig, and still other embodiments at a pressure of at least 30,000 psig, and in yet still other embodiments at a pressure of at least about 50,000 psig. Also as discussed previously, for embodiments where a collimated jet is desired, nozzle 232 preferably has a length to minimum internal diameter ratio of at least about four, more preferably at least about six, and in other embodiments at least about ten. Jet opening 236 typically has a circular cross-sectional area, but may, in other embodiments, have other cross-sectional shapes, such as rectangular, oval, slit-like, etc., for forming jets having different shapes for specific desired purposes. In preferred embodiments, jet opening 236 has an internal diameter of between about 0.001 and about 0.02' inches, more preferably between about 0.003 and about 0.01' inches, and most preferably about 0.005 inches.

Liquid jet 238, which is collimated as it exits jet opening 236, tends to create a visible, opaque entrainment region 242 surrounding liquid jet 238. Entrainment region 242 is comprised of rapidly moving liquid, which is entrained and driven by the kinetic energy of liquid jet 238. Liquid jet 238, as it rapidly moves through liquid environment 244, also tends to create a zone of low pressure, which is essentially coextensive with entrainment region 242. In typical embodiments involving high pressure liquids and rapidly moving liquid jets, the pressure in entrainment region/low pressure zone 242 will be lower than the vapor pressure of the surrounding liquid in liquid environment 244, thus causing cavitation of the liquid in entrainment region 242 and a resulting formation of an abundance of extremely small gas bubbles 246 within the liquid in the entrainment region 242, making the region visually opaque.

As discussed previously, it is desired, in preferred embodiments, for safety and performance that the instrument be designed to reduce, and preferably eliminate, undesirable effects, such as blow-by of the liquid jet, plugging of the jet-receiving opening and the evacuation lumen, and inefficient tissue/debris entrainment and removal. Also, as previously mentioned, in preferred embodiments, it is desirable that ablated tissue and debris be evacuated from the surgical site through the evacuation lumen, without the need for a source of external suction to be applied to the proximal end of the evacuation lumen. In order to provide the above-mentioned characteristics, the inventive surgical instruments for use in a liquid environment can include an evacuation lumen having specifically selected predetermined shapes and configurations, which is positionable relative to the jet opening at a specific predetermined distance. Specifically, in preferred embodiments, jet-receiving opening 234 is positioned, when the instrument is in operation, opposite jet opening 236, at a predetermined distance l therefrom, and provided in a nozzle 232 having a length to minimum diameter ratio so that essentially all of the fluid in liquid jet 238 enters jet-receiving opening 234. As discussed above, liquid jet 238 will tend to create entrainment region 242 surrounding the liquid jet 238 when the instrument is in operation. Entrainment region 242 will typically be symmetrically deposed around liquid jet 238 and will tend to diverge in a direction from jet opening 236 to jet-receiving opening 234. In typical embodiments where jet opening 236 is circular in shape, entrainment region 242 will have a truncated cone shape, having a truncated apex at jet opening 236 and a base defined as a cross section of the cone at the plane of jet-receiving opening 234. In preferred embodiments, the base of entrainment region 242 occupies between about 50% and about 100% of the cross-sectional area of jet-receiving opening 234 when the instrument is in operation, more preferably the entrainment region occupies at least about 75%, more preferably still at least about 90%, and most preferably at least about 95% of the cross-sectional area of jet-receiving opening 234 when the instrument is in operation.

As shown in FIG. 5c, the cross-sectional area of the jet-receiving opening 234 required to ensure that the entrainment region 242 occupies the desired relative fraction of the cross-sectional area of the jet-receiving opening 234, as discussed above, is functionally related to the chosen predetermined distance l between the jet opening 232 and the jet-receiving opening 234 and the degree of divergence characterizing the entrainment zone (represented by angle $\phi$ in FIG. 5c). Specifically, the desired cross-sectional radius b of the base of the entrainment region 242 at the jet-receiving opening 234 is related to predetermined distance l and the degree of divergence of the entrainment region by $b = l \tan \phi$. Predetermined distance l is typically selected based on the desired use of the surgical instrument, dictating a required fluid path cutting/ablating length. Based upon this desired predetermined distance l, the required size of the jet-receiving opening 234 is typically determined experimentally by submersing the pressure lumen 230 and nozzle 232 in a liquid environment 244, forming a liquid jet 238 by supplying a liquid to the nozzle 232 at a desired predetermined pressure, and visually observing the size of the entrainment region 242 or cavitation cone created around the liquid jet 238, and estimating angle $\phi$ from the observations.

As mentioned above, the predetermined separation distance l between the jet opening 236 and the jet-receiving opening 234 depends upon the requirements of the particular surgical procedure for which the surgical instrument is used; however, for some typical embodiments, the predetermined distance will have a maximum value of about 1 cm, for other typical embodiments, about 5 mm, and for yet other typical embodiments, about 1 mm. The jet-receiving opening 234 typically will have a diameter of between about 0.01 and about 0.2 inches, in other embodiments between about 0.03 and about 0.1 inches, and in some preferred embodiments a diameter of about 0.06 inches.

Referring again to FIG. 5a, a preferred configuration for evacuation lumen 240 will now be described. Preferred embodiments of evacuation lumen 240 for use in surgical instruments intended to be operated in a liquid environment include a maceration region 246 within and/or downstream and in close proximity to the inlet to evacuation lumen 240 at jet-receiving opening 234. Maceration region 246 is defined as a region that contains a liquid undergoing intensely turbulent flow and impacting an internal surface of the evacuation lumen at an acute angle, thus creating significant impacting forces capable of macerating entrained material/tissue, when the instrument is in operation. The combination of the intensely turbulent flow of the liquid in maceration region 246 and the impacting forces of liquid jet 238 and the liquid in entrainment region 242 against the wall of evacuation lumen 240 enable the liquid within the maceration region to macerate at least a portion of any tissue or material entrained by the liquid in entrainment region 242 into a plurality of small particles. In preferred embodiments, the maceration region is able to macerate a substantial fraction (i.e., the majority of) the entrained tissue into a plurality of small particles. In most preferred embodiments, the plurality of particles at least partially comprises a plurality of microscopic particles too small to be seen unaided with the human eye. In all cases, the particles should be small enough to pass through evacuation lumen 240 without plugging the evacuation lumen, when the instrument is in operation.

In order to provide a maceration region, evacuation lumen 240 preferably includes a jet-deflecting portion 248 that is located adjacent to and downstream of jet-receiving opening 234. Jet-deflecting region 248 may be either a straight surface that is angled with respect to the direction of at least a central portion of liquid jet 238, or in preferred embodiments, jet-deflecting region 248 comprises a smoothly curved surface upon which at least a portion of liquid jet 238 impinges, where the curved surface is shaped to deflect at least a portion, and preferably all of the liquid jet 238 and liquid comprising entrainment region 242 in a direction that is essentially parallel to the longitudinal axis 250 of evacuation lumen 240 in the region proximal to the jet-deflecting region 248. In preferred embodiments, the radius of curvature of the curved surface defining jet-deflecting region 248 is essentially constant, having a value of between about 1 and 20 times the internal diameter of evacuation lumen 240. In the most preferred embodiments, as shown in FIG. 5a, the radius of curvature of the curved surface defining jet-deflecting region 248 is essentially equal to the internal diameter of evacuation lumen 240 at jet-deflecting region 248, so that essentially no portion of jet-receiving opening 234 projects radially beyond a perimeter defined by an outer surface 252 of a portion of the evacuation lumen located proximal and adjacent to jet-deflecting region 248. It is also generally preferable for the surgical instruments provided by the invention that the liquid jet be directed into the jet-receiving opening so that a direction of at least a central portion of the liquid jet forms an angle of no greater than 10 degrees with respect to a line normal (i.e., perpendicular) to a plane defining (i.e., co-planar to) the jet-receiving opening. In the most preferred embodiments, the central portion of the liquid jet is essentially parallel to a line that is normal to the plane defining the jet-receiving opening.

In order to provide effective eductor pump action of evacuation lumen 240, in some embodiments, evacuation lumen 240 will have an essentially constant internal cross-sectional area from jet-receiving opening 234 to a position that is proximal to the distal end of the surgical instrument where the proximal end of the evacuation lumen is located. In other embodiments, eductor pump action can be enhanced by providing an evacuation lumen having an essentially constant cross-sectional area and having a jet-receiving opening, which has a cross-sectional area that is less than the cross-sectional area of the evacuation lumen (i.e., the internal cross-sectional area of the evacuation lumen has a minimum value at the jet-receiving opening). In yet other embodiments, eductor pump action can be enhanced by providing an evacuation lumen having an internal cross-sectional area which increases continuously from a minimum value at the jet-receiving opening to a maximum value at a predetermined position located proximal to the jet-receiving opening. In such embodiments, this maximum value of the internal cross-sectional area should be essentially constant for positions within the evacuation lumen that are proximal to the above-mentioned predetermined position. In each of the above-mentioned embodiments, there are preferably essentially no reductions in the internal cross-sectional area of the evacuation lumen at any position proximal and/or downstream of the maceration region described above.

FIG. 5b shows an alternative design embodiment for the construction of the evacuation lumen for surgical instruments designed for use in a liquid surgical environment. Evacuation lumen 260 includes a constriction 262 in the internal cross-sectional area of the evacuation lumen. The constriction 262 is located proximal to jet-receiving opening 264, and is preferably positioned immediately proximal and adjacent to maceration region 266. In operation, the constriction 262 in the evacuation lumen 260 will act as a venturi as liquid within the evacuation lumen flows through the constriction, thus enhancing the eductor pump action of evacuation lumen 260. In the illustrated embodiment, constriction 262 comprises a pinch 268 in the sidewall of the tubing conduit comprising evacuation lumen 260. In preferred embodiments, the cross-sectional area of constriction 262 should be between about three and about eight times the cross-sectional area of jet-opening 270 in nozzle 272.

Referring again to FIG. 5a, evacuation lumen 240 is shaped and positioned relative to pressure lumen 230 so that at least a central portion of liquid jet 238 is directed into jet-receiving opening 234 in a direction forming a non-zero angle with respect to (i.e. non-parallel with) the longitudinal axis 250 of evacuation lumen 240 in a region proximal to jet-deflecting region 248. In some embodiments, this angle can be between about 45 and 115 degrees, in other embodiments between about 80 and 100 degrees, and in some preferred embodiments, as illustrated, the angle can be about 90 degrees. In other embodiments, involving surgical instruments designed for use in a liquid environment, the direction of at least the central portion of the liquid jet and longitudinal axis of the evacuation lumen in a region proximal to the jet-deflecting region may be essentially parallel, as shown for example by the embodiment illustrated in FIG. 7d.

FIGS. 6a and 6b illustrate preferred arrangements for liquid jet surgical instruments designed for use in a surrounding gaseous environment. Referring to FIG. 6a, a partially cutaway view of the distal ends of a pressure lumen 280 and evacuation lumen 282 of a surgical liquid jet instrument for use in gaseous environment 284 is shown. For instruments designed for use in a gaseous environment, nozzle 286 preferably has a lower length to minimum internal diameter ratio than preferred nozzles employed for instruments designed for use in a liquid environment. As discussed previously, preferably nozzle 286, constructed in the illustrated embodiment as a hole bored in a sidewall of pressure lumen 280, has a length to minimum internal diameter ratio not greater than about four, and more preferably not greater than about two Unlike the relatively collimated liquid jets preferred for instruments for use in a liquid environment, instruments for use in a gaseous environment preferably create a diverging liquid jet as a high pressure liquid flows through the nozzle. Preferably, liquid jet 288 emitted from jet opening 290, when the instrument is in operation, is a diverging jet creating an entrainment region comprised of a diverging zone of liquid droplets 292 moving through gaseous environment 284. The zone of liquid droplets comprising liquid jet 288 will tend to create a region of relatively low gas pressure, when compared to the pressure in the gas surrounding the liquid jet region 288, that will have a tendency to entrain and draw tissue and material into an entrainment region that is essentially co-extensive with jet region 288.

Of critical concern for most applications employing liquid jet surgical instruments in a gaseous environment is minimizing, and preferably eliminating, misting and back spray of the liquid jet from the jet-receiving opening. Such misting or back spray can cause poor visualization of the surgical field, in addition to potentially creating infectious and/or undesirable aerosolization of material into the surrounding gaseous environment. In order to avoid back spray or misting from the evacuation lumen, evacuation lumen 282 is preferably essentially straight at its distal end so that an axis 294 defining the direction of at least a central region of liquid jet 288 is essentially co-linear with the longitudinal axis of the distal end of evacuation lumen 282. With such configurations, essentially complete tissue maceration is not as critical as for instruments creating liquid jets having central regions directed at steep angles (e.g. between 45 and 135 degrees) to the longitudinal axis of the distal end of evacuation lumen (e.g. as shown above in FIG. 5a) because material and debris typically have a lower tendency to accumulate in, and potentially clog, an essentially straight distal end of an evacuation lumen.

As mentioned above, liquid jet 288 is preferably a diverging jet, which diverges as it travels from jet opening 290 to jet-receiving opening 296. Diverging jet 288 will have an apex at jet opening 290 and, for essentially circular jet opening shapes, will typically have a truncated cone shape, where the truncated apex of the cone is located at jet opening 290 and the base of the cone is defined as the planar cross section of the cone at jet-receiving opening 296. As was previously the case for surgical instruments designed for use in a liquid environment, preferred embodiments of surgical instruments designed for use in a gaseous environment provide an evacuation lumen shaped and positioned relative to the jet opening, when the instrument is in operation, so that the base of the liquid jet entrainment region occupies between about 50% and about 100% of the cross-sectional area of the jet-receiving opening, more preferably the entrainment region occupies at least about 75%, even more preferably at least about 90%, and most preferably at least about 95% of the cross-sectional area of the jet-receiving opening. As was previously described in the context of instruments for use in a liquid environment, the size of jet-receiving opening 296 can be selected based upon the desired separation distance between jet opening 290 and jet-receiving opening 296 and the length to minimum internal diameter ratio of nozzle 286, which dictates the degree of divergence of liquid jet 288. Analogous to the geometrical relationships discussed previously in the context of FIG. 5c, the relationship between the radius of liquid jet entrainment region 288 at jet-receiving opening 296 is related to separation distance l between jet opening 290 and jet-receiving opening 296 as b=l tan φ where φ defines the divergence angle of liquid jet 288, which is related to the length to minimum diameter ratio of nozzle 286, and b is defined as the radius of the base of the liquid jet entrainment region 288. As described before, the desired size of jet-receiving opening 296 is typically determined experimentally, for example by creating a liquid jet in a gaseous environment using a desired liquid supply pressure and a given nozzle configuration, visually observing the diverging liquid jet formed, and estimating angle φ from the observation. The appropriate jet-receiving opening size can then be selected based on φ and the desired separation distance l.

In preferred embodiments, it is also desirable to shape and position evacuation lumen 282 with respect to jet opening 290 so that the cross-sectional shape and area of liquid jet 288 at a given location 298 within evacuation lumen 282 is essentially the same as the internal cross-sectional shape and area of evacuation lumen 282 at given location 298. Given location 298 may coincide with jet-receiving opening 296 or may be located proximal to jet-receiving opening 296. For embodiments where given location 298 is located proximal to jet-receiving opening 296, preferably the given location 298 is no greater than about 5 mm proximal to jet-receiving opening 296. By shaping and positioning evacuation lumen 282 in this fashion, it is assured that liquid jet 288 completely fills the cross-sectional area of the evacuation lumen 282 at a position at or near its distal entrance, thus essentially eliminating back spray and misting and improving evacuation via eductor pump action.

Evacuation lumen 282 may have an essentially constant internal cross-sectional area, may have an essentially cross-sectional area with a jet-receiving opening having a cross-sectional area that is less than the cross-sectional area of evacuation lumen 282, or may have an internal cross-sectional area which increases continuously from a minimum value at jet-receiving opening 296 to a maximum value at a predetermined position proximal to jet-receiving opening 296, which then remains essentially constant for positions proximal to the predetermined position. Alternatively, as shown in FIG. 6b, the instrument may include an evacuation lumen 300 having a constriction 302 located proximal to a jet-receiving opening 304, which constriction acts as a venturi to enhance the eductor pump action of evacuation lumen 300. For embodiments including a constriction in the evacuation lumen, it is preferred that the liquid jet 306 contact the inner surface of evacuation lumen 300 at a given location 308 that is located distal to constriction 302. The cross-sectional area of constriction 302 is preferably between about three and fifteen times greater than the cross-sectional area of jet opening 303 in nozzle 305.

It should be understood that while certain preferred embodiments of the inventive liquid-jet surgical instruments for use in a liquid environment have been described as including an evacuation lumen constructed and positioned to provide a jet-deflecting surface upon which a liquid jet impinges, and while certain preferred embodiments of the inventive liquid-jet surgical instruments for use in a gaseous environment have been described as providing an evacuation lumen that is essentially straight and does not include a jet-deflecting surface, the liquid jet surgical instruments within the scope of the present invention are not so limited. Specifically, configurations such as those shown in FIGS. 5a and 5b could be employed for a surgical instrument intended for use in a gaseous environment in an application where the potential creation of misting and/or back spray is not critical. Similarly, the configurations illustrated in FIGS. 6a and 6b could alternatively be employed for use in a surgical instrument intended to be used in a liquid environment in applications where the essentially co-axial orientation of the liquid jet is acceptable for allowing access to the desired surgical site and where essentially complete tissue maceration is not critical.

FIG. 7 illustrates a variety of contemplated embodiments for the distal end of a liquid jet surgical instrument, according to the invention. FIG. 7a shows a partially cutaway view of the distal end of the surgical instrument having a sheath 310 from which a pressure lumen 312 extends distally. Evacuation lumen 314 is completely contained within and surrounded by sheath 310. During operation, a liquid jet is emitted from jet opening 316 and directed into jet-receiving opening 318 such that at least a central portion of the liquid jet is directed proximally and parallel to a longitudinal axis of sheath 310. The configuration shown in FIG. 7a is well suited for surgical instruments intended for use in gaseous environments and may also be useful for surgical instruments intended for use in liquid environments, where extensive maceration of tissue is not critical.

Figure 7A:
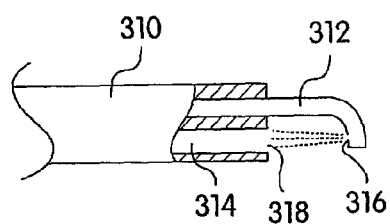
FIG. 7a is a partially-cutaway schematic illustration of a portion of a surgical liquid jet instrument, the portion including the distal end of the surgical liquid jet instrument.
Figure 7B:
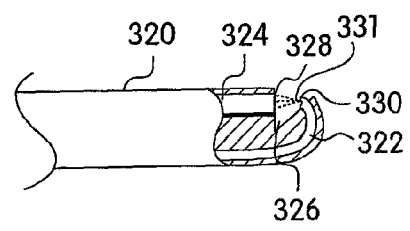
FIG. 7b is a partially-cutaway schematic illustration of a portion of a surgical liquid jet instrument, the portion including the distal end of the surgical liquid jet instrument.
Figure 7C:
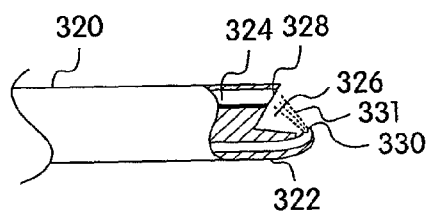
FIG. 7c is a partially-cutaway schematic illustration of a portion of a surgical liquid jet instrument, the portion including the distal end of the surgical liquid jet instrument.

FIGS. 7b and 7c show two embodiments of the distal end of a surgical liquid jet instrument according to the invention where the distal end of sheath 320 essentially completely surrounds both pressure lumen 322 and evacuation lumen 324. The liquid jet path length is created in the instruments by providing a notch 326 at the distal end of sheath 320 where the proximal surface of notch 326 includes a jet-receiving opening 328, and the distal end of notch 326 includes a jet opening 330. In some embodiments, sheath 320 may be constructed from a flexible material, such as a polymeric material, and the configurations shown in FIGS. 7b and 7c may comprise part of a liquid jet surgical instrument configured as an elongated catheter. The configuration shown in FIGS. 7b and 7c are substantially similar except that in FIG. 7b, the liquid jet 331 emitted from jet opening 330 has a central region directed proximally and parallel to the longitudinal axis of sheath 320, and in contrast, the central region of the liquid jet 331 for the configuration shown in FIG. 7c, is directed towards jet-receiving opening 328 at an angle of about 45 degrees with respect to the longitudinal axis of sheath 320.

Figure 7D:
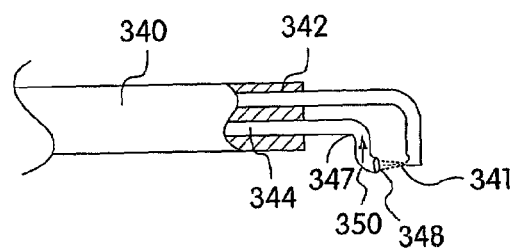
FIG. 7d is a partially-cutaway schematic illustration of a portion of a surgical liquid jet instrument, the portion including the distal end of the surgical liquid jet instrument.

FIG. 7d illustrates an embodiment of a distal end of a surgical liquid jet instrument according to the invention that is capable of providing a maceration zone for a liquid jet 341 whose central region is directed proximally and essentially parallel to the longitudinal axis of sheath 340 and the proximal end of the instrument to which it would be connected. The sheath 340 has a distal end from which projects pressure lumen 342 and evacuation lumen 344. Evacuation lumen 344 has two curved regions 347, 350 near its distal end, the second curved region 350 being adjacent to jet-receiving opening 348 and providing a jet-deflecting region.

Figure 7E:
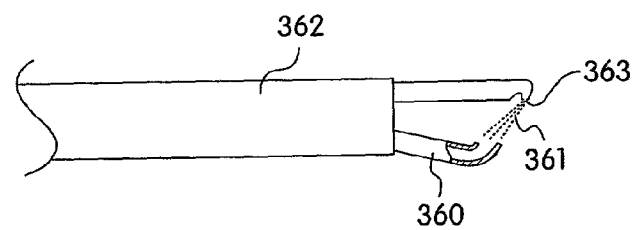
FIG. 7e is a partially-cutaway schematic illustration of a portion of a surgical liquid jet instrument, the portion including the distal end of the surgical liquid jet instrument.

FIG. 7e illustrates an embodiment for a distal end of a surgical instrument according to the invention that is similar to that described previously in FIG. 5a, except that the central region of the liquid jet 361 formed by the nozzle 363 in the configuration of FIG. 7e has a direction forming an angle with respect to the longitudinal axis of evacuation lumen 360 and sheath 362 that is approximately 45 degrees, as opposed to about 90 degrees for the configuration shown in FIG. 5a.

The invention also provides various embodiments of surgical liquid jet instruments having distal ends for insertion into a surgical operating space that have a predetermined contour and size that are selected to facilitate inserting the distal end into the confined surgical operating space. Preferred embodiments of such surgical instruments provided by the invention include mechanisms for creating relative motion between the pressure lumen and evacuation lumen in order to change the orientation, positioning, and/or configuration of the lumen with respect to each other, for example to increase a separation distance between the jet opening and the jet-receiving opening. Embodiments of surgical liquid jet instruments having actuating mechanisms, as provided by the invention, typically enable the distal end of the instruments to be inserted into a surgical operating space in an undeployed configuration, and subsequently deployed by an operator to provide a desired separation distance between the jet opening and the jet-receiving opening in order to yield a desired liquid jet path length. Typically, embodiments involving deployable liquid jet surgical instruments are directed to surgical applications involving confined regions within the body of a patient, such as joint capsules. In many such embodiments, the surgical environment surrounding the distal end of the instrument, when it is in operation, is a liquid environment.

FIGS. 8a–8c illustrate one embodiment of a deployable liquid jet surgical instrument according to the invention. FIG. 8a shows an instrument 380 with distal end 382 in an undeployed configuration. Distal end 382 of instrument 380 includes pressure lumen 384 and evacuation lumen 386, which protrude from the distal end of sheath 388. In the undeployed configuration shown, pressure lumen 384 and evacuation lumen 386 are essentially co-directional along their length, within the distal end 382 of instrument 380, and, therefore, provide a minimum cross-sectional dimension for distal end 382 of instrument 380. Sheath 388 also includes a region of reduced cross-section 390 near its distal end in order to provide a reduced cross-sectional dimension of instrument 380 near distal end 382. The contour and size of distal end 382 can be selected to facilitate inserting the distal end 382 of instrument 380 into a confined surgical operating space for a particular surgical procedure. For example, in embodiments where instrument 380 is used to perform a surgical procedure in the human knee, preferably the distal end 382 of surgical instrument 380 has at least one cross-sectional dimension that does not exceed about 2.8 mm when surgical instrument 380 is in the undeployed configuration. When utilizing such an instrument for a surgical procedure on the knee, the cross-sectional dimension of the undeployed distal end not exceeding 2.8 mm is oriented essentially normal to the plane of the tibial plateau in order to facilitate insertion of the distal end into the knee. Distal end 382 may also include a region 392 near the extreme distal end of instrument 380 that is angularly displaced from the longitudinal axis of sheath 388 by a desired angle α. This angle may be selected to improve the ease of insertion of the device into a particular confined surgical operating space within the body of a patient. For example, for embodiments where surgical instrument 380 is used to perform a surgical procedure within a joint capsule comprising a human knee, the maximum angle α of angled or curved region 392 of distal end 382 with respect to the longitudinal axis of sheath 388 or body 394 of surgical instrument 380 is preferably about 15 degrees.

Body 394 of surgical instrument 380 includes a grasping region 396 configured to fit within the hand of an operator. Body 394 may be constructed of a variety of materials, and is preferably constructed of a resilient, inexpensive, easily moldable polymeric material, which may, in certain embodiments, be injection molded or cast to form the body. Various polymeric materials may be used to form body 394, as would be apparent to those of ordinary skill in the art, including but not limited to, polyethylene, polypropylene, polystyrene, polycarbonate, polyacrylate, polyvinyl chloride, phenolic polymer, nylon, and others, as well as mixtures, copolymers, and combinations thereof, etc. As previously discussed, instrument 380 is preferably constructed from relatively inexpensive and easy to assemble materials, so that the entire instrument may be disposable after a single use. Body 394 of surgical instrument of 380 also includes an actuating element 398, which comprises a rotatable knob, that is controllable by the hand of an operator and useful for deploying distal end 382 of instrument 380, as described in more detail below.

FIG. 8b shows surgical instrument 380 in the deployed configuration. Surgical instrument 380 can be deployed by rotating actuating element 398 in a clockwise direction causing a corresponding rotation of the distal end of pressure lumen 384 with respect to evacuation lumen 386. The direction of rotation of the distal end of pressure lumen 384 is indicated in the figure by arrow 400. Upon rotation of pressure lumen 384 with respect to body 394 of instrument 380, the separation distance 402 defining a liquid jet path length between jet opening 404 and jet-receiving opening 406 increases from a value of essentially zero, when instrument 380 is in the undeployed position, to a desired predetermined distance defined by the limits of travel of actuating element 398. In some embodiments, the actuating element may include one or more detents constructed to hold the actuating element at one or more intermediate positions within the limits of travel to allow the predetermined distance to be adjusted to a variety of predetermined values. The structure of such detents is well understood by those of ordinary skill in the art and will not be described in detail herein. Such detents may also be provided as part of the actuating mechanisms of the embodiments of deployable surgical instruments described below. In preferred embodiments of the deployable surgical liquid-jet instruments according to the invention, the actuating element is constructed to have a continuous range of motion over its limits of travel so that the predetermined distance defining the jet path length is continuously and infinitely adjustable by the operator. This desired predetermined distance can be selected to provide a desired liquid jet cutting/ablating path length for a particular surgical procedure. For example, for surgical procedures performed within a human joint capsule, such as a human knee, the maximum separation distance between jet opening 404 and jet-receiving opening 406 should preferably not exceed about 4 mm.

FIG. 8c more clearly shows the internal features of surgical instrument 380. Evacuation lumen 386 is fixably mounted within body 394 of surgical instrument 380 so that it is essentially immobile with respect to body 394. Proximal end 408 of evacuation lumen 386 comprises a barbed fitting to which is coupled low pressure evacuation conduit 410. Pressure lumen 384 is rotatably mounted within sheath 388 and body 394 of instrument 380 and is fixably mounted to actuating element 398. The proximal end 412 of pressure lumen 384 is coupled to high pressure liquid supply conduit 416 via high pressure tubing coupler 414, as described previously. Body 394 of surgical instrument 380 includes a rotatable coupling 418 through which high pressure liquid supply conduit 416 traverses. Rotatable coupling 418 is configured to allow conduit 416 and pressure lumen 384 to rotate with respect to body 394 upon actuation of rotatable knob 398.

Figure 8D:
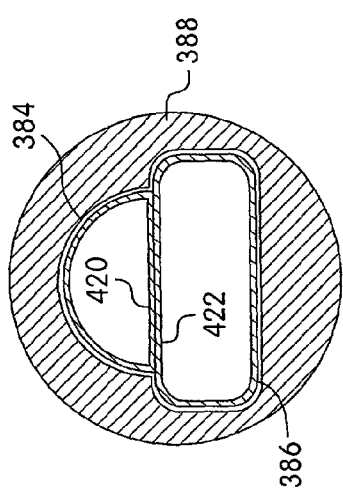
FIG. 8d is a cross-sectional illustration of the sheath, pressure lumen, and evacuation lumen of the surgical instrument as in FIG. 8c.

FIG. 8d shows a cross-sectional view of sheath 388 of surgical instrument 380. In the embodiment illustrated, pressure lumen 384 has a semi-hemispherical shape having a flat region 420 positioned near the center of sheath 388. Evacuation lumen 386 has an essentially rectangular cross-sectional shape with a flattened region 422 that is co-directional and in contact with flattened region 420 of pressure lumen 384. The illustrated, non-circular configuration of lumens 384 and 386 can serve a dual purpose. First, the non-circular shape can enable the reduction of the overall cross-sectional dimension of distal end 382 of instrument 380, when in the undeployed configuration. In addition, flat regions 420 and 422 impart desirable lateral stiffness to lumens 384 and 386 to prevent undesirable bending of the lumens upon contact with surfaces within an operating field, which bending can cause misdirection of the liquid jet and potential unintended tissue damage. In an alternative embodiment, pressure lumen 384 and/or evacuation lumen 386 may have an essentially circular cross-sectional shape and may each be deployed within separate channels within the sheath for additional support, such as shown in FIG. 2a previously.

Figure 9:
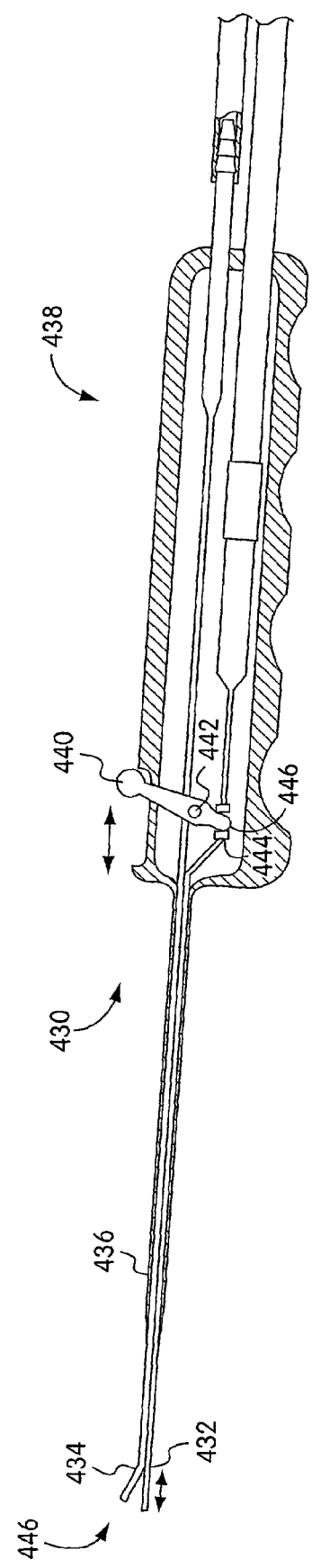
FIG. 9 is a cross-sectional illustration of a deployable surgical liquid jet instrument, where deployment of the instrument is accomplished by longitudinal movement of the pressure lumen.

FIG. 9 shows an alternative embodiment for a deployable surgical liquid jet instrument where deployment is effected via a longitudinal movement of at least one of the lumen with respect to the body of the instrument. Surgical instrument 430 is shown with the distal end 446 in the deployed configuration. Instrument 430 includes an evacuation lumen 434 that is fixably mounted within body 438 and/or sheath 436 so that the evacuation lumen 434 is essentially immovable with respect to body 438. Surgical instrument 430 also includes a pressure lumen 432 which is slidably mounted within sheath 436 and body 438 to allow the distal end of pressure lumen 432 to slide in and out of the distal end of sheath 436 upon actuation of slidable lever 440 by an operator of the instrument. Slidable lever 440 is pivotally mounted to body 438 via attachment to pin element 442. Pressure lumen 432 includes two camming elements 444 fixed thereto, which are mounted so that end 446 of slidable lever 440 is located between camming elements 444. Upon movement of slidable lever 440, pressure lumen 432 is moved longitudinally within sheath 436 and body 438 in order to deploy the distal end of pressure lumen 432.

Figure 10:
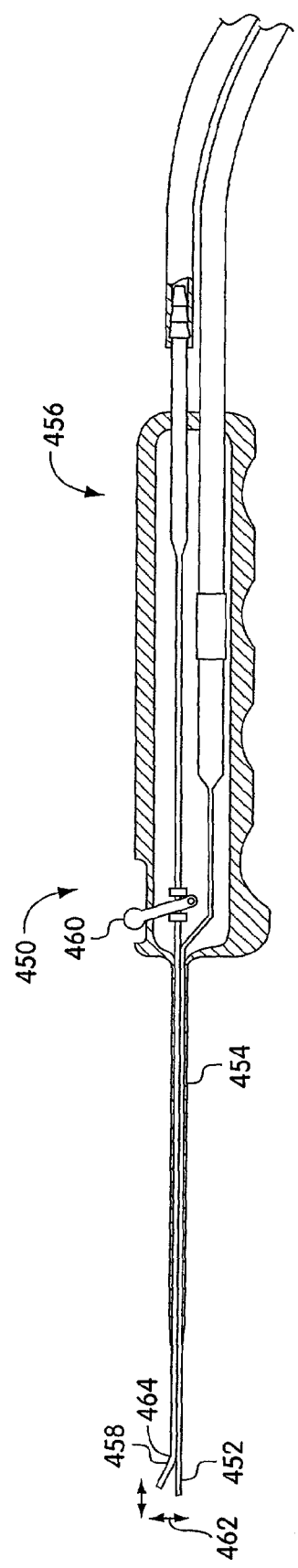
FIG. 10 is a cross-sectional illustration of a deployable surgical liquid jet instrument, where deployment of the instrument is accomplished by longitudinal movement of the evacuation lumen.

FIG. 10 shows an alternative embodiment of a deployable surgical instrument, where the instrument is deployed by longitudinal movement of at least one lumen with respect to the body of the instrument. Surgical instrument 450 is shown in the deployed configuration and includes pressure lumen 452 which is fixably mounted within body 456 and/or sheath 454, and which is essentially immobile with respect to body 456. Surgical instrument 450 further includes an evacuation lumen 458 which is longitudinally movable with respect to body 456 via slidable lever 460, which is mounted within body 456. Upon an operator moving slidable lever 460 distally with respect to body 456 from the indicated position in the figure, the distal end of evacuation lumen 458 is withdrawn into the distal end of sheath 454. Upon deployment, the distal end of evacuation lumen 458 emerges distally from the distal end of sheath 454 and also moves laterally, indicated by arrows 462, with respect to the distal end of pressure lumen 452, in order to create a separation distance between the jet opening and the jet-receiving opening. In order to provide the necessary lateral movement of the distal end of evacuation lumen 458 upon deployment of instrument 450, the distal end of evacuation lumen 458 can be constructed from a shape memory spring steel material, or may include a hinged joint, or flexible, bendable portion, or other means for pivoting evacuation lumen 458 at point 464 so as to create a lateral movement of the evacuation lumen when the evacuation lumen is longitudinally deployed from sheath 454. In other embodiments, the lateral motion of the distal end of evacuation lumen 458 upon deployment may be controllable by an operator of the instrument via manipulation of an element (not shown) provided on the body 456 of the instrument 450 that is connected to the distal end of the evacuation lumen 458. For example, one or more wires may be provided, which are attached to a controllable element provided on the body 456 of the instrument 450 and which pass through sheath 454, and that are attached at their distal ends to the longitudinally movable distal end of evacuation lumen 458. In such embodiments, creation of a tension on the wire or wires via actuation of an element on the body of the instrument could be used to create a force on the movable tip of evacuation lumen 458 in order to move it laterally with respect to the distal end of pressure lumen 452, upon deployment of the instrument. Those of ordinary skill in the art would readily appreciate that there are many mechanisms by which the distal end of evacuation lumen 458 may be longitudinally and laterally deployed that are within the scope and spirit of the present invention.

An alternative embodiment for a rotatably deployed surgical liquid jet instrument is shown in FIGS. 11a–11f.

Figure 11A:
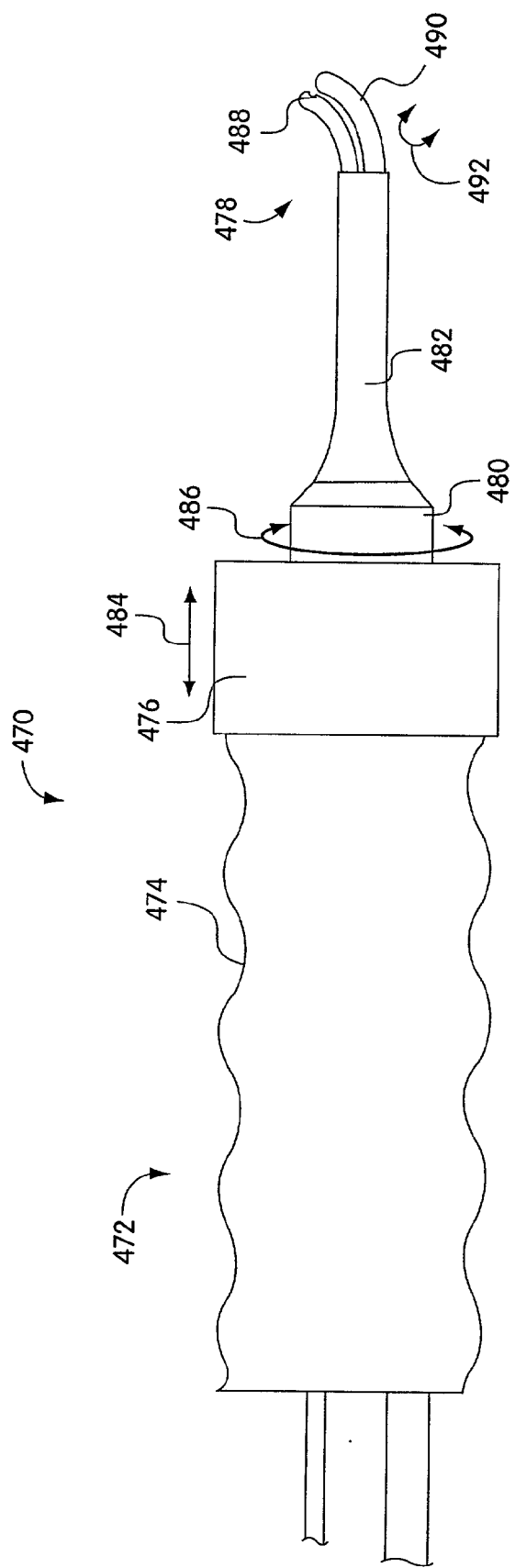
FIG. 11a is a schematic illustration of a rotatably deployable surgical liquid jet instrument having a single actuating element.

Referring to FIG. 11a, surgical instrument 470 includes a body 472 having a grasping region 474 configured to be held within the hand of an operator and an actuating element 476 that comprises a slidable sleeve or collar, which is used to deploy the distal end 478 of surgical instrument 470. Slidable sleeve 476 is positioned to be easily actuated by a single hand of an operator of instrument 470. Slidable sleeve 476 can enable the operator to hold body 472 in at least two different hand/grasping region 474 orientations, so that the operator can actuate slidable sleeve 476 while holding body 472 in either of the at least two hand/grasping region 474 orientations. For example, an operator can grip body 472 in a hand position where the thumb of the operator is located near the distal end of gripping region 474. In such position, the operator can actuate slidable sleeve 476 by moving the slidable sleeve with her thumb. In a second hand/grasping region orientation, the operator can grip body 472, for example, with her thumb positioned toward the proximal end of body 472, while actuating slidable sleeve 476 via one or more of the other four fingers of her hand.

Surgical instrument 470 also includes a component 480 that is rotatably mounted within body 472. Rotatably mounted component 480 is typically a cylindrically-shaped sleeve, which may be attached to, or form part of, sheath 482. Distal end 478 of surgical instrument 470 is shown in FIG. 11a in an undeployed configuration. Sliding sleeve 476 in the direction of arrows 484 causes a rotational motion of rotatably mounted component 480 in the direction shown by arrows 486, which, in turn, causes a rotation of evacuation lumen 490 about a longitudinal axis of sheath 482, which is essentially parallel to the longitudinal axis of body 472 and the longitudinal axis of the portion of evacuation lumen 490 within sheath 482. In other embodiments, upon deployment, evacuation lumen 490 may rotate about the longitudinal axis of sheath 482, which is essentially collinear to the longitudinal axis to of the portion of evacuation lumen 490 within sheath 482, both of which axes are essentially parallel to the longitudinal axis of body 472. In yet alternative embodiments, instead of evacuation lumen 490 rotating upon deployment of instrument 470, evacuation lumen 490 may instead be immobile with respect to body 472 and pressure lumen 488 may rotate upon actuation of slidable sleeve 476.

Figure 11B:
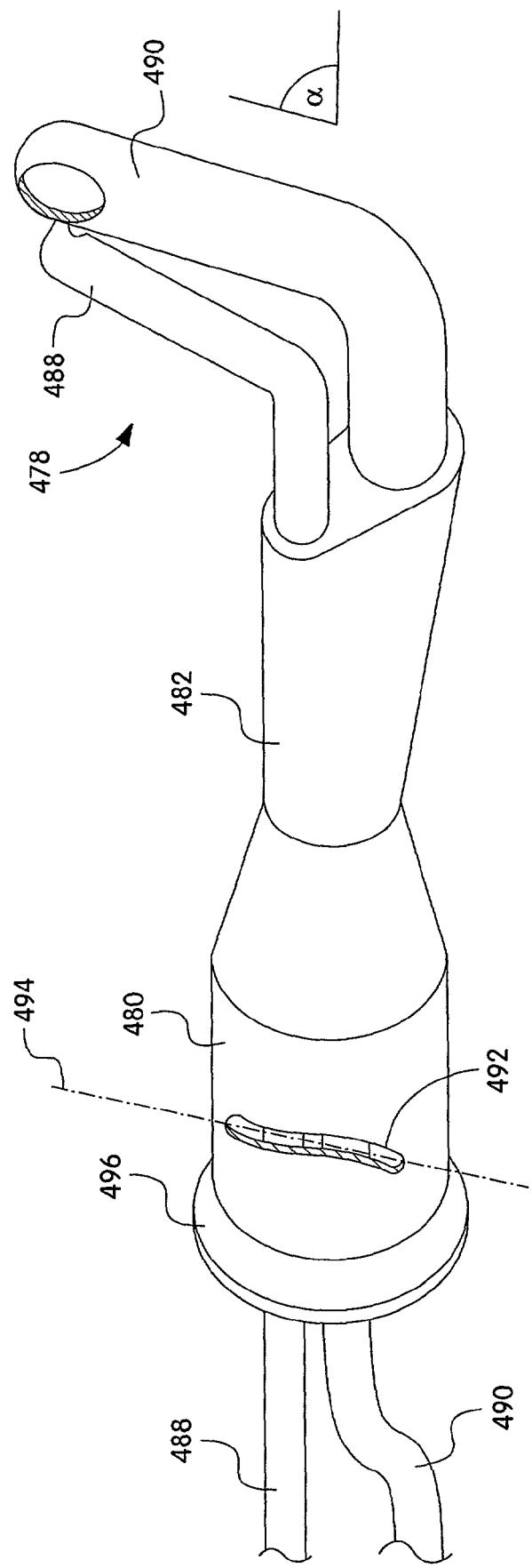
FIG. 11b is a schematic illustration of a portion of the surgical liquid jet instrument as in FIG. 11a showing more clearly the rotatably mounted component, sheath, and distal end of the instrument, when in the undeployed configuration.
Figure 11C:
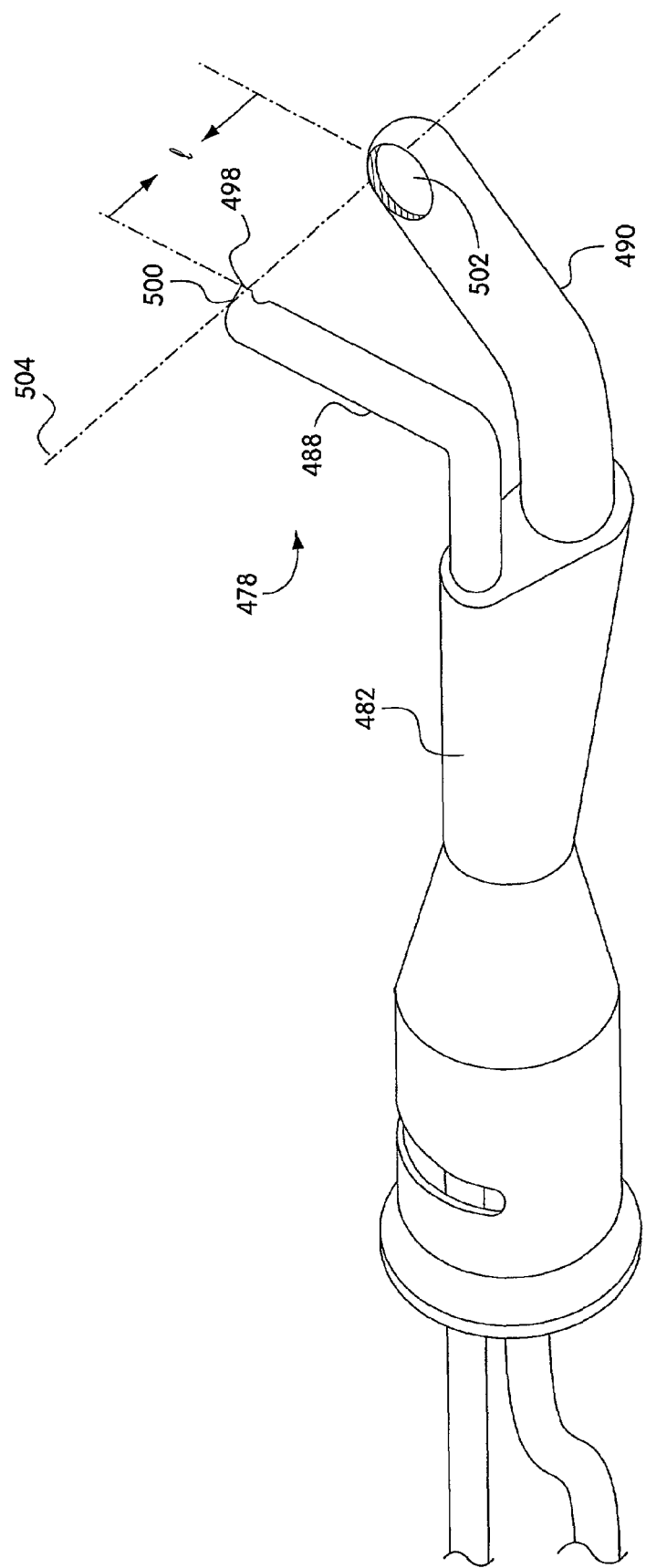
FIG. 11c is a schematic illustration of a portion of the surgical liquid jet instrument as in FIG. 11a showing more clearly the rotatably mounted component, sheath, and distal end of the instrument, when in the deployed configuration.

The distal end of surgical instrument 470 is shown in greater detail in FIGS. 11b and 11c. FIGS. 11b and 11c also show sheath 482 and rotatably mounted component 480 in greater detail. Distal end 478 of surgical instrument 470 is shown in FIG. 11b in the undeployed position and in FIG. 11c in the deployed position. In the undeployed position, distal end 478 has a cross-sectional dimension, length, and angular orientation α with respect to the longitudinal axis of the sheath 482 and the longitudinal axis of the body 472 of instrument 470, which are selected to facilitate insertion of distal end 478 into a confined surgical operating space for a particular surgical procedure, as discussed previously. For example, for arthroscopy, at least one cross-sectional dimension of distal end 478, when in the undeployed configuration, should be no greater than about 2.8 mm, the length of distal end 478 is preferably between 10 and 15 mm, and angle α is preferably about 15 degrees. Pressure lumen 488 is fixably mounted within body 472, so that it is essentially immobile with respect to body 472, and is rotatably mounted within sheath 482 and rotatably mounted component 480 so that the sheath can rotate around the outer surface of the pressure lumen upon deployment of distal end 478. By contrast, evacuation lumen 490 is fixably mounted to sheath 482 and/or rotatably mounted component 480, but is rotatably moveable within body 472 upon rotation of rotatably mounted component 480, so that rotation of rotatably mounted component 480 and sheath 482 causes a corresponding rotation of evacuation lumen 490 resulting in deployment of distal end 478. Rotatably mounted component 480 includes a slot or groove 492 having a longitudinal axis 494 that is non-parallel with respect to the longitudinal axis of rotatably mounted component 480 and the longitudinal axis of body 472 of instrument 470. Slot 492 is used to create rotation of rotatably mounted component 480 upon movement of slidable sleeve 476, as described in more detail below. Rotatably mounted component 480 also includes a bearing flange 496 which is mounted within body 472 of instrument 470 to allow for rotation of component 480, as described in more detail below. Deployment of distal end 478, as shown in FIG. 11c, establishes a separation distance l between jet opening 498 in nozzle 500 and jet-receiving opening 502 at the distal end of evacuation lumen 490. Separation distance l defines a liquid jet path length, when the instrument is in operation. In certain preferred embodiments, axis 504 which defines the direction of a central region of the liquid jet emitted from jet opening 498 when the instrument is in operation, is non-parallel with respect to the longitudinal axes of sheath 482 and body 472 of instrument 470. Typically, for such embodiments, axis 504 forms an angle with respect to the longitudinal axis of body 472 that is between about 45 and 115 degrees, more typically between about 80 and about 100 degrees, and most typically about 90 degrees.

Figure 11D:
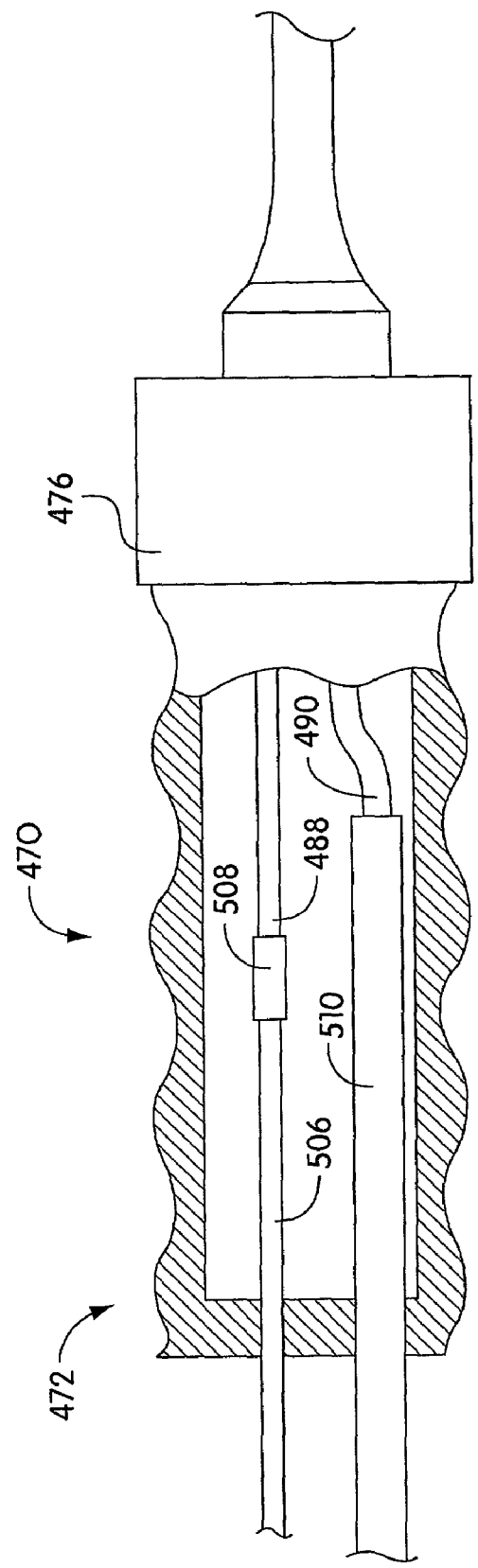

FIG. 11d shows a partially cutaway view of surgical instrument 470 showing more clearly the proximal end of body 472 and the connection of pressure lumen 488 to high pressure liquid supply conduit 506 and evacuation lumen 490 to evacuation conduit 510. Pressure lumen 488 can be connected to high pressure liquid supply conduit 506 via a high pressure tubing connector 508 as previously described. Pressure lumen 488 and/or high pressure liquid conduit 506 are fixably mounted within body 472 to prevent movement of pressure lumen 488 with respect to body 472 during deployment. Evacuation lumen 490 rotates within body 472 upon movement of actuating element 476. Evacuation lumen 490 is connected to evacuation conduit 510, which is flexible and/or twistable within body 472, to allow evacuation lumen 490 to rotate.

Figure 11E:
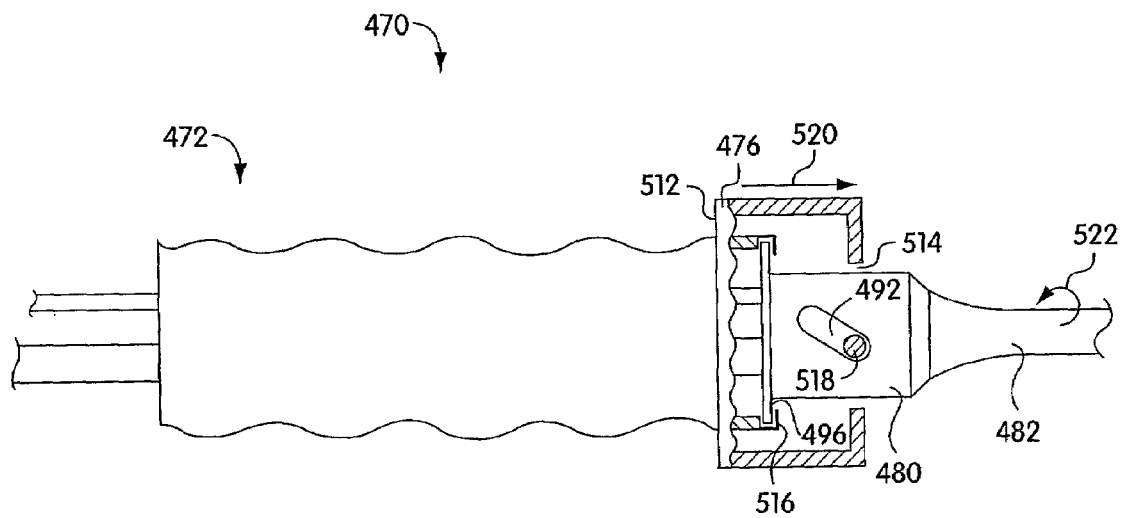
Figure 11F:
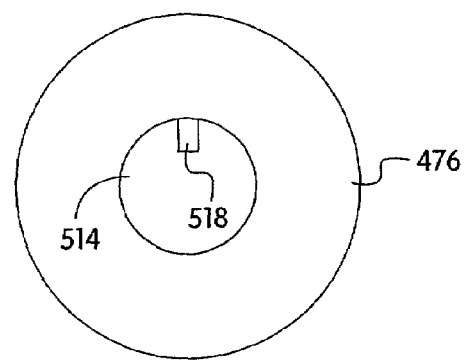

The actuating mechanism by which actuating element 476 causes rotation of rotatably mounted component 480 and sheath 482, in order to deploy distal end 478 of instrument 470, is shown more clearly in FIGS. 11e and 11f. Referring to FIG. 11e, a cut away view of actuating element 476 is shown. Actuating element 476 can be generally cylindrical in shape and includes two apertures 512 and 514. Aperture 512 is located on the proximal surface of actuating element 476 and allows actuating element 476 to accommodate body 472 of instrument 470. Aperture 514 is located on the distal surface of actuating element 476 and has a circumference that is nearly equal or slightly greater than the outer circumference of rotatably mounted component 480, thus allowing rotatably mounted component 480 to pass through, and rotate within, aperture 514. Bearing flange 496 of rotatably mounted component 480 is rotatably mounted within bearing slots 516 of body 472. Shown in FIG. 11f, actuating element 476 includes a pin 518 mounted within aperture 514. As shown more clearly in FIG. 11e, when assembled, pin 518 fits within slot 492 of rotatably mounted component 480 so that as an operator slides actuating element 476 in the direction of arrow 520, pin 518 slides forward in slot 492 causing rotation of rotatably mounted component 480 in the direction shown by arrow 522, thus causing deployment of the distal end of instrument 470.

Figure 12A:
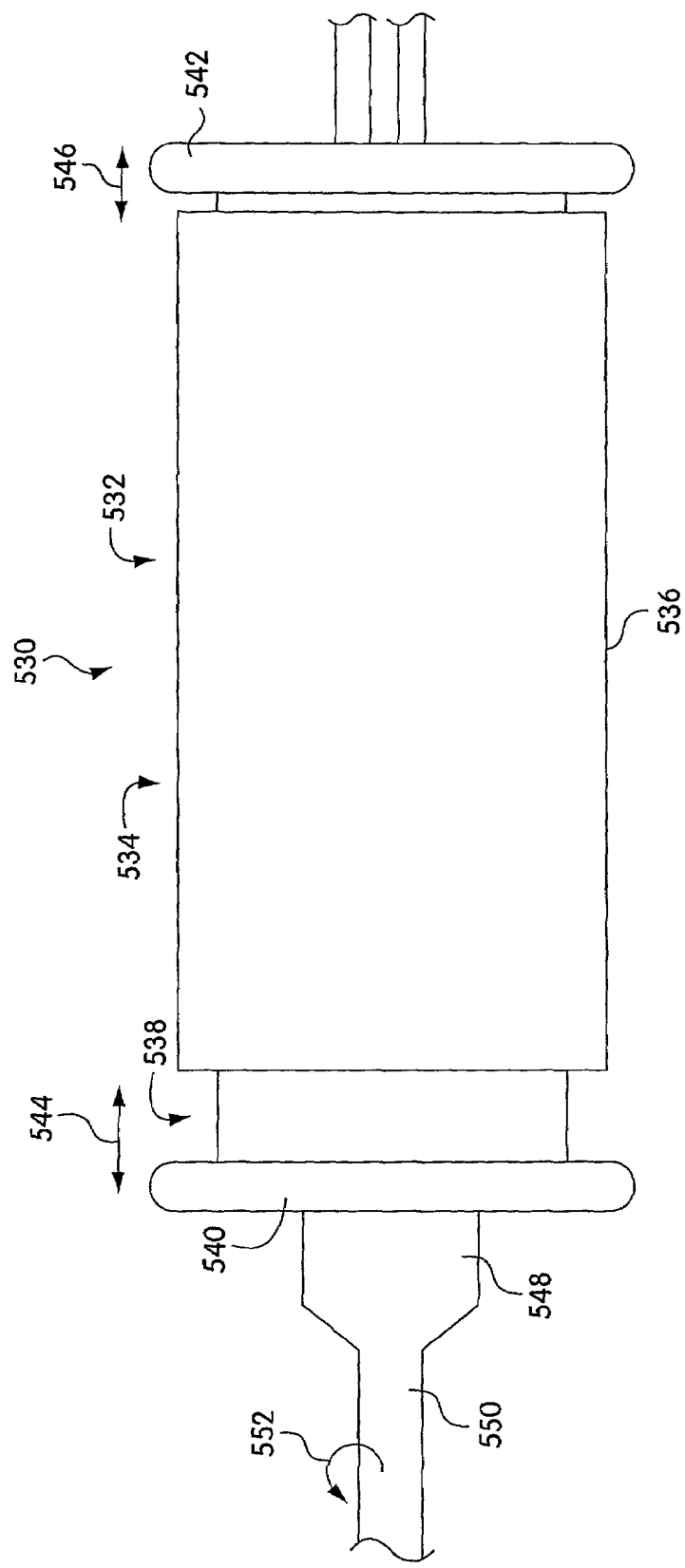
FIG. 12a is a schematic illustration of a portion of a rotatably deployable surgical liquid jet instrument having two actuating elements.

FIGS. 12a–12e show an alternative embodiment for a rotatably deployable surgical liquid jet instrument according to the invention. Referring to FIG. 12a, surgical instrument 530 is shown, which has a body 532 including an outer body component 534 with an external surface 536 that acts as a grasping region, and an internal body component 538, which is slidably mounted within outer body component 534. Inner body component 538 includes two actuating elements 540, 542, each of which may be actuated by the hand of an operator holding grasping region 536. By sliding either actuating element in the direction indicated by arrows 544 and 546, the operator can create a rotational movement of rotatably mounted component 548 and sheath 550 in the direction indicated by arrow 552. Actuating elements 540 and 542 are positioned with respect to grasping region 536 so that the operator is able to hold body 532 of the instrument in at least two different hand/grasping region orientations, while being able to access at least one of actuating elements 540 or 542 in either hand/grasping region orientations. This configuration is particularly advantageous when the instrument is designed for arthroscopic use in the knee or the shoulder.

Figure 12B:
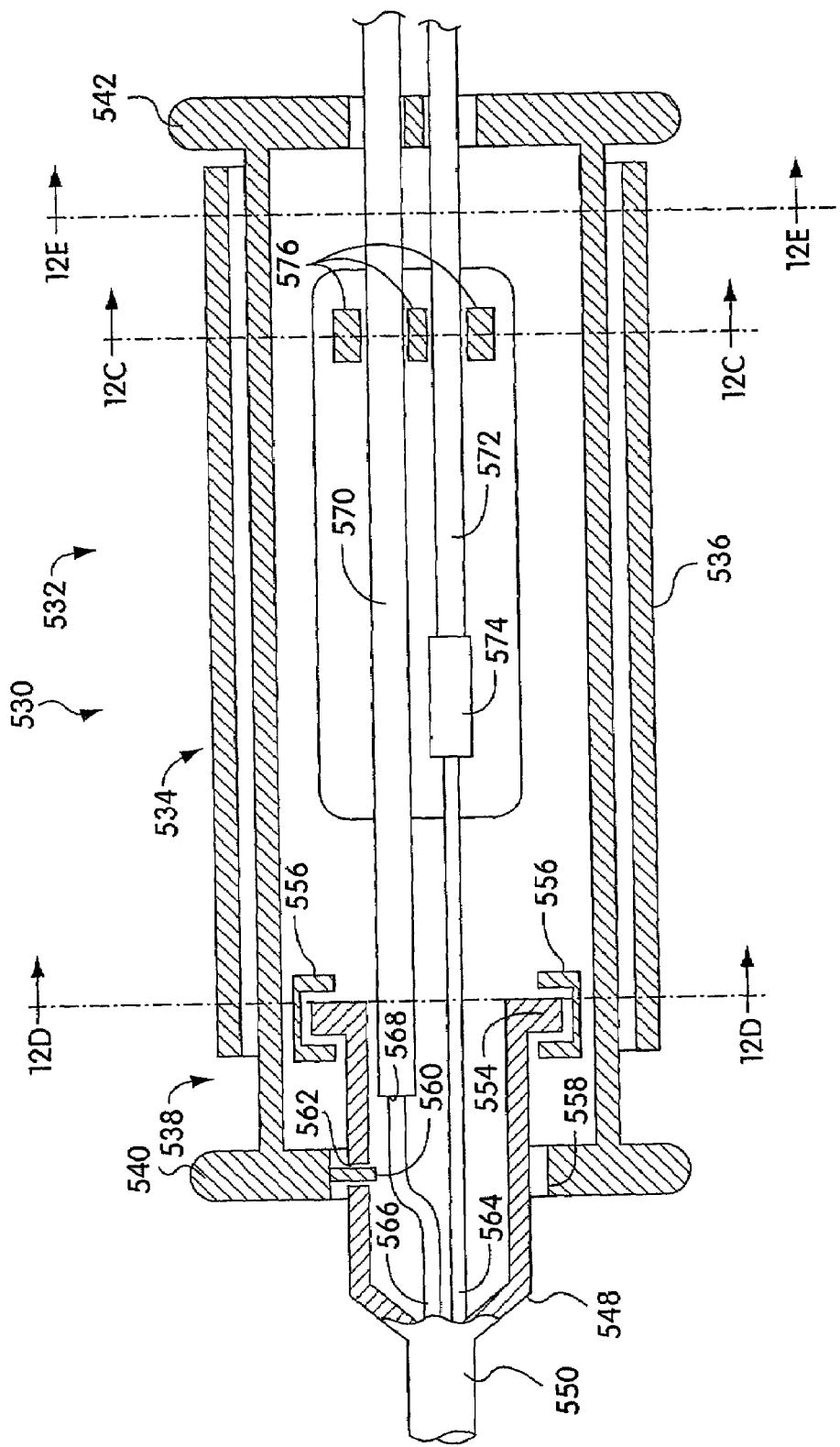
Figure 12C:
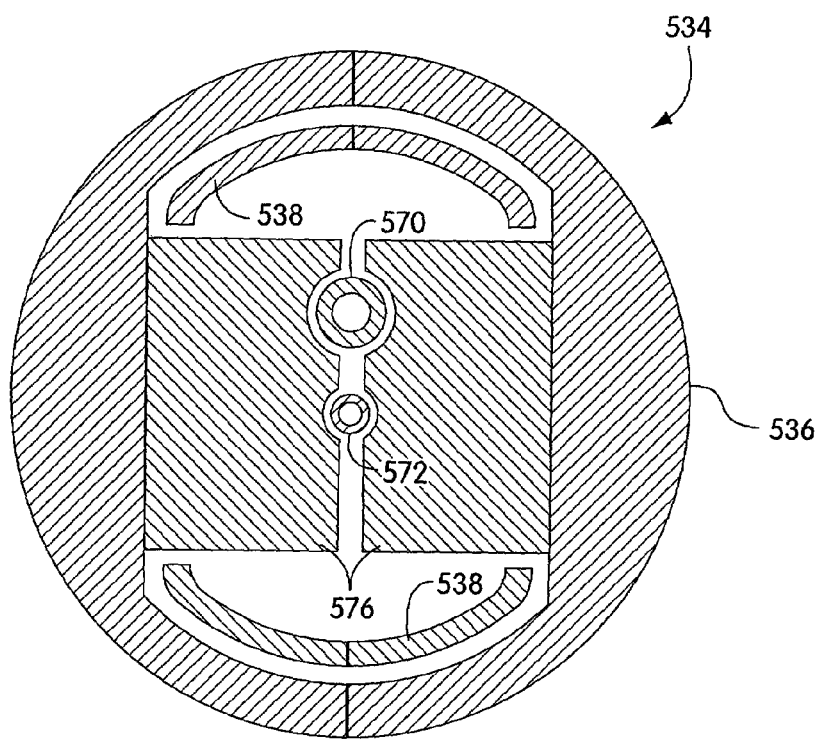
Figure 12D:
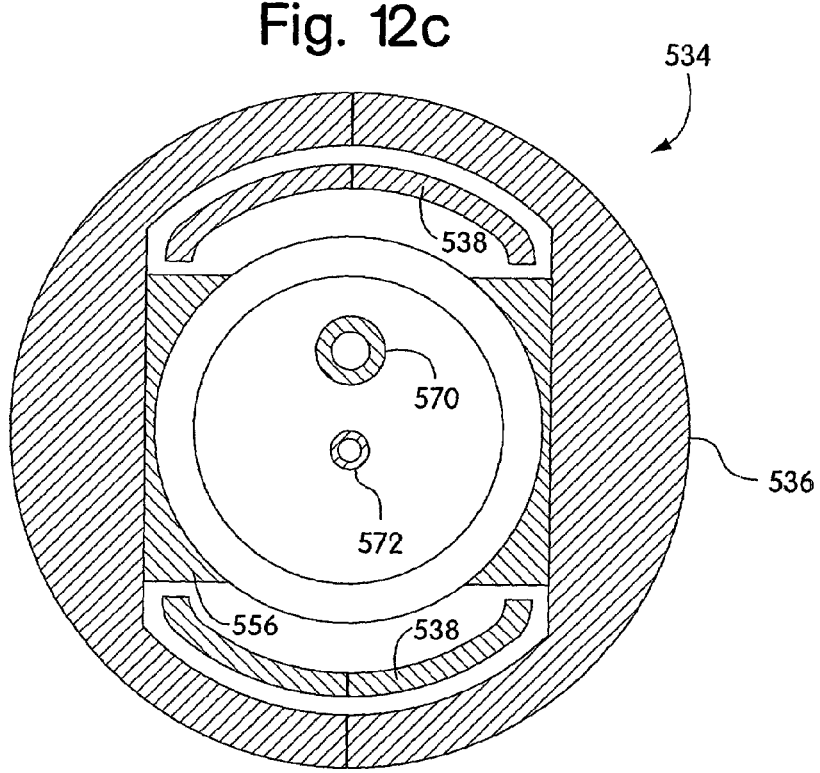
Figure 12E:
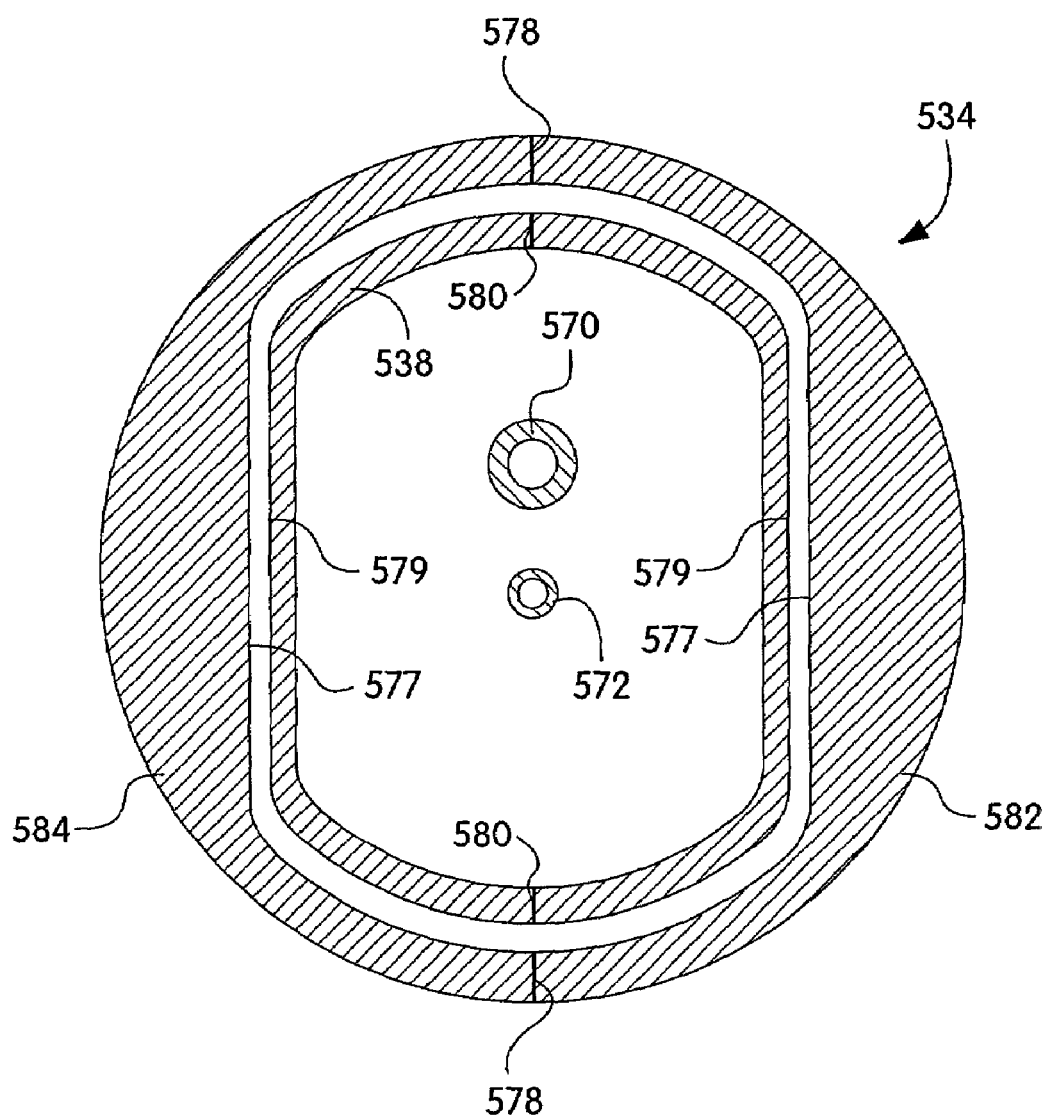

The internal components of surgical instrument 530 are shown more clearly in the cross-sectional views of FIGS. 12b–12e. As shown in FIG. 12b, rotatably mounted component 548 includes bearing flange 554 at its proximal end. Bearing flange 554 is rotatably mounted within bearing slots 556, which are connected to outer body component 534 as shown more clearly in FIG. 12d. Rotatably mounted component 548 extends distally from bearing slots 556 through aperture 558 in actuating element 540. Actuating element 540 includes a pin 560 which traverses slot 562 in rotatably mounted component 548 when instrument 530 is assembled (similar to the configuration shown previously in FIG. 11e). Thus, by sliding inner body component 538 with respect to outer body component 534 via actuating elements 540 or 542, the operator can slide pin 560 within slot 562 causing rotation of rotatably mounted component 548 and sheath 550. In the embodiment shown, pressure lumen 564 is fixably mounted within body 532, but is free to rotate within rotatably mounted component 548 and sheath 550. Evacuation lumen 566, by contrast, is fixably attached to sheath 550 and/or rotatably mounted component 548, so that evacuation lumen 566 rotates with respect to body 532 upon rotation of rotatably mounted component 548 and sheath 550, in order to deploy the distal end of instrument 530. In order to enable evacuation lumen 566 to rotate within body 532, evacuation lumen 566 is coupled at its proximal end 568 to a flexible/twistable evacuation conduit 570. Pressure lumen 564 is coupled to high pressure conduit 572 via high pressure connector 574, as previously discussed. High pressure conduit 572 and evacuation conduit 570 are immobilized within body 532 via tubing holder elements 576, which are connected to outer body component 534 as shown most clearly in FIG. 12c. As shown most clearly in FIG. 12e, outer body component 534 and inner body component 538 are hollow and concentric, and have complementary shapes to allow the components to slide easily relative to one another. Preferably, outer body component 534 and inner body component 538 have complementary shapes that allow for relative longitudinal motion (sliding) of the components, but which prevent relative rotational movement. In the illustrated embodiment, relative rotation is prevented by planar inner surfaces 577 of outer body component 534 and planar outer surfaces 579 of inner body component 538. As would be apparent to those of ordinary skill in the art, many alternative shapes for the outer body component and the inner body component are possible that allow the components to slide relative to each other while preventing relative rotation of the components, all of which are within the scope and spirit of the invention.

In preferred embodiments, outer body component 534 and inner body component 538 comprise components that are injection molded from a lightweight, inexpensive, and durable polymeric material. The components may be manufactured as two symmetrical halves (e.g., halves 582 and 584 of outer body component 534), which may be connected together upon assembly of instrument 530. Connection points between the halves of the components, shown as 578 and 580, can be snap-fit joints, or may be connected together via screws, clips, clamps, tape, adhesives, solvent fusing, or any other suitable means of attachment as apparent to those of ordinary skill in the art.

Figure 13:
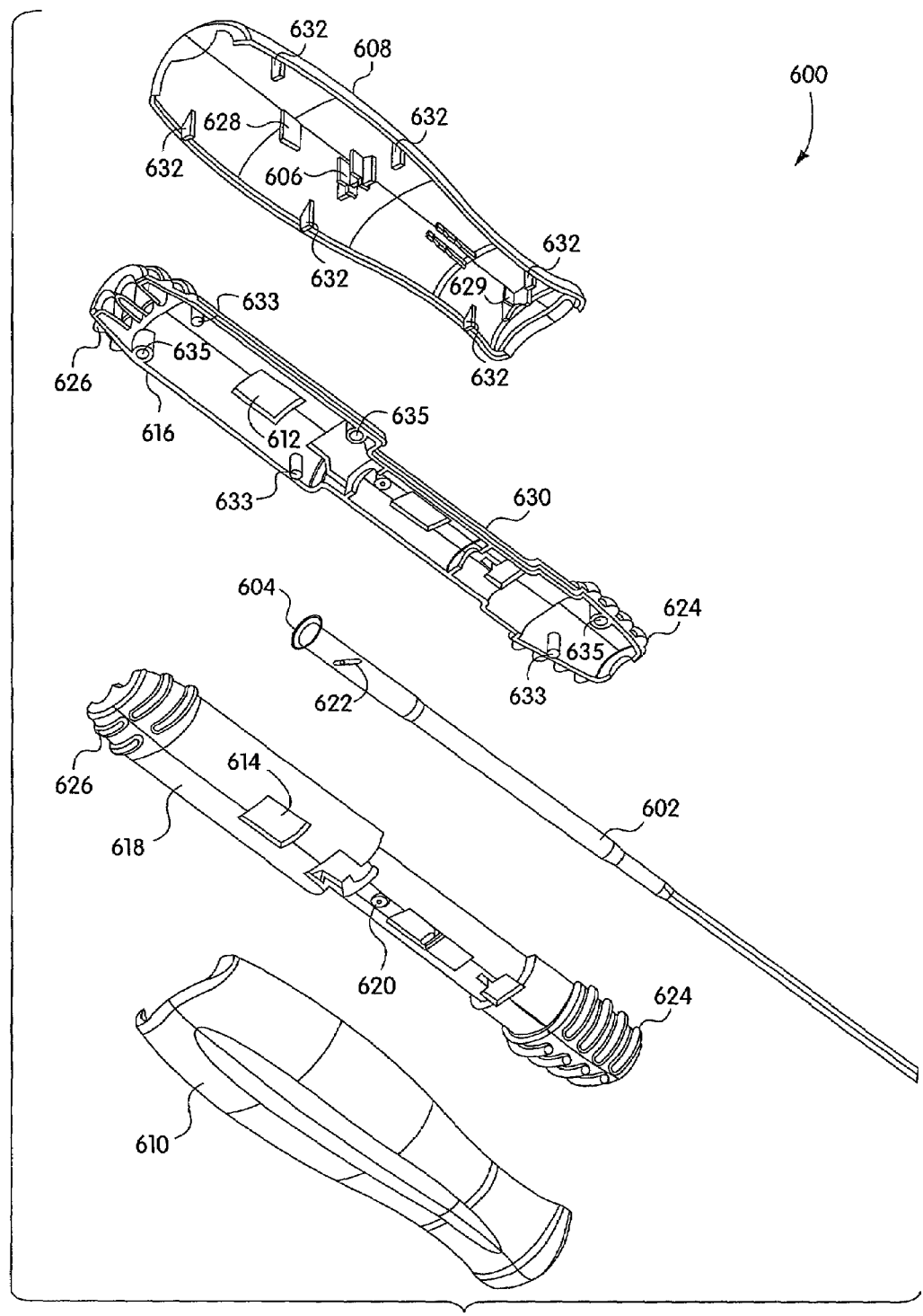
FIG. 13 is an exploded, perspective illustration of a portion of a rotatably deployable surgical liquid jet instrument having two actuating elements.

FIG. 13 shows an exploded view of a surgical instrument 600 that is similar in construction and operation to surgical instrument 530 shown in FIG. 12a. Surgical instrument 600 includes a rotatably mounted component 602 having a bearing sheath 604 which is rotatably mounted within a bearing slot formed by component 606 on outer body component half 608 and a similar component on outer body component half 610 (not visible). When instrument 600 is assembled, bearing flange 604 will pass through windows 612 and 614 within inner body component halves 616 and 618 to allow it to engage with the bearing slot components 606 on the outer body halves 608, 610. Inner body component half 618 also includes pin 620 mounted therein which traverses slot 622 on rotatably mounted component 602 when instrument 600 is assembled. When instrument 600 is assembled, the inner body component is able to slide within the outer body component over a range of motion defined by the length of slot 622 on rotatably mounted component 602. Movement of the inner body component and rotation of rotatably mounted component 602 can be effected by an operator holding instrument 600, via actuating elements 624, located at the distal end of the inner body component, and/or actuating elements 626, located at the proximal end of the inner body component.

Various components can be included as part of the outer body component and/or inner body component that are useful for supporting the pressure lumen, evacuation lumen, and rotatably mounted component 602 within the body. For example, tubing support component 628 on outer body component half 608 can interact with a complementary component on outer body component half 610 to support and immobilize the pressure and evacuation lumen/conduits, when instrument 600 is assembled. Similarly, sheath support components 630 on inner body component halves 616 and 618, and sheath support components 632 on outer body component halves 608 and 610 act to support and properly position rotatably mounted component 602 when instrument 600 is assembled. Inner body component half 616 also includes dowel elements 633 and dowel receptacle elements 635, which are sized and shaped to securely fit together, that mate with complementary elements (not shown) on inner body component half 618 upon assembly of the instrument. Similarly, outer body component half 608 includes flanges 632, which are sized and positioned to mate with complementary slots (not shown) on outer body component half 610, upon assembly, to improve the security of the connection of the component halves and durability of the body after assembly. Preferably, the component halves of the inner and outer body components are further secured together by gluing, solvent bonding, ultrasonic welding, or press fitting, but may, in other embodiments, be secured by a variety of means apparent to those of ordinary skill in the art including, but not limited to, screws, clips, clamps, straps, etc.

It should be understood that the above mentioned mechanical actuation mechanisms for the inventive surgical instruments are purely exemplary, and that modifications to the above-mentioned mechanisms, or alternative ways of deploying the distal ends of the inventive surgical instruments to provide a separation distance defining a liquid jet path length may be envisioned by those of ordinary skill in the art, and that such modifications, or alternative mechanisms are within the scope and spirit of the present invention, as described and defined by the appended claims. For example, for the embodiments shown in FIGS. 11a–11f, instead of employing an actuating element having a pin, and a rotatably mounted component having a groove in which the pin slides upon sliding the actuating element, in other embodiments, the actuating element may instead be rigidly attached to the rotatably mounted component, so that rotation of the rotatably mounted component is effected by rotation of the actuating element by the operator. In yet other embodiments, instead of employing actuating components comprising slidable sleeves, or body components that are slidable relative to one another as shown in FIGS. 11a–11f and FIGS. 12a–12e, alternatively, the actuating element may comprise one or more slidable levers, or rotatable knobs, having a pin attached thereto, within the body of the device.

The deployable surgical instruments described above are especially useful for performing surgical procedures in confined regions internally of a body defining a confined surgical operating space. As discussed previously, the distal ends of the instruments are provided with a contour in size that is specifically selected to facilitate inserting the distal end of the surgical instruments into the confined regions, when the instrument is in an undeployed configuration. Accordingly, the inventive instruments enable the performance of novel surgical methods utilizing the inventive instruments. For example, the deployable surgical liquid jet instruments described above may be advantageously employed for use in a surgical method involving the cutting or ablating of a selected tissue within the joint capsule of a patient. The method comprises inserting a surgical-liquid jet instrument, provided by the invention, and having a distal end specifically designed for the surgical procedure, into the joint capsule of the patient. Upon insertion of the instrument into the joint capsule, the operator of the instrument can then deploy the distal end of the instrument to create a separation distance between the jet opening and the jet-receiving opening, defining a liquid jet path length. The operator can then turn on a pump or dispenser supplying high pressure liquid to the device, as discussed previously, in order to create a liquid jet with the surgical instrument. The liquid jet can then be directed towards the jet receiving opening in the evacuation lumen of the instrument, and will tend to create an entrainment region surrounding the liquid jet, which can be effective for cutting or ablating a selected tissue within the joint capsule.

In some procedures, the cutting or ablating of tissue can comprise positioning the liquid jet nozzle in close proximity to a solid surface within the joint capsule, for example the surface of a bone, and directing the liquid jet essentially parallel to the solid surface to remove selected tissue from the surface. Depending on the hardness and toughness of the material to be removed from the surface, the liquid jet, in some instances, may need to be brought essentially adjacent to the solid surface. For soft material, such as fatty tissue, the liquid jet need not be brought into direct contact with the material, or with the solid surface containing the material, but rather, the entrainment region created by the liquid jet can draw the material from the surface towards the jet in order to cut and/or ablating the material and evacuate the material through the evacuation lumen. For very hard tissue, such as bone or cartilage, the liquid jet entrainment region may need to be brought into essentially direct contact with the material to be cut and/or ablated. Advantageously, preferred surgical instruments according to the invention are capable of performing the above mentioned surgical procedures and evacuating ablated material, blood, and debris from the surgical operating space without requiring an external source of suction. The above mentioned instruments, because of their effectiveness in removing material from the operating space, can provide a surgical operating field providing excellent visibility for the operator performing the surgical procedure.

A representative procedure, meniscectomy of a human knee, employing the inventive fluid jet cutting system is described immediately below. First, the patient to be operated on is anesthetized and a tourniquet is applied the thigh of the leg and set to a pressure of about 280 mm Hg. The patient is then prepped and draped in the conventional manner. Saline is introduced into the knee either through a superior medial portal, using an inflow canula, or through a scope canula placed in the lateral portal at the joint line. Saline can exit the knee cavity out of the medial portal at the joint line. The pathology of the knee can be visualized through use of an endoscopic camera. After bending the knee, valgus or varus stress is applied to facilitate the approach to tight compartments within the joint capsule. The inventive surgical liquid jet instrument is then inserted, in the undeployed configuration, through one of the portal. As discussed above, the profile and contour of the distal end of the instrument is designed specifically for facilitating access into the confined regions of the knee anatomy, and to provide a proper cutting orientation during use. Specifically, upon insertion into the joint cavity of the knee, while in the undeployed position, the surgical instrument is configured to pass through the tight gap between the condyle and the tibial plateau, so that the instrument may be deployed after it is properly positioned at the posterior meniscus site. While in operation, the instrument breaks up ablated or cut tissue into small, and preferably microscopic fragments and evacuates it from the knee, without the need for external suction, through the evacuation lumen. After completing the surgery, the fluid jet instrument and visualization endoscope can be removed from the portals and the knee can be drained and wrapped.

Surgical liquid jet instruments according to the invention can also be used for operative procedures in other joint capsules of a patient, for example, the human shoulder. For certain procedures, for example, acromioplasty within the shoulder, which can involve a significant amount of bleeding, it is contemplated that the surgical instruments provided according to the invention can be utilized in conjunction with electrocautery in order to reduce bleeding caused by the surgical procedure.

Figure 14A:
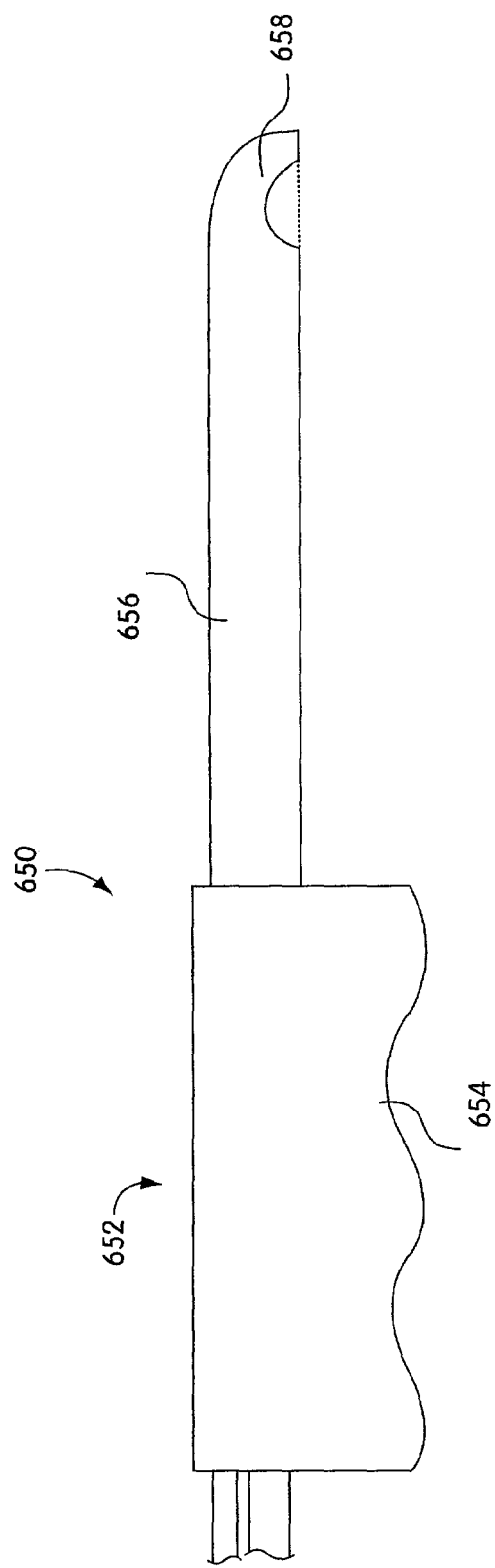
FIG. 14a is a schematic illustration of the surgical liquid jet instrument having a pressure lumen that includes two nozzles, each providing a jet opening.
Figure 14B:
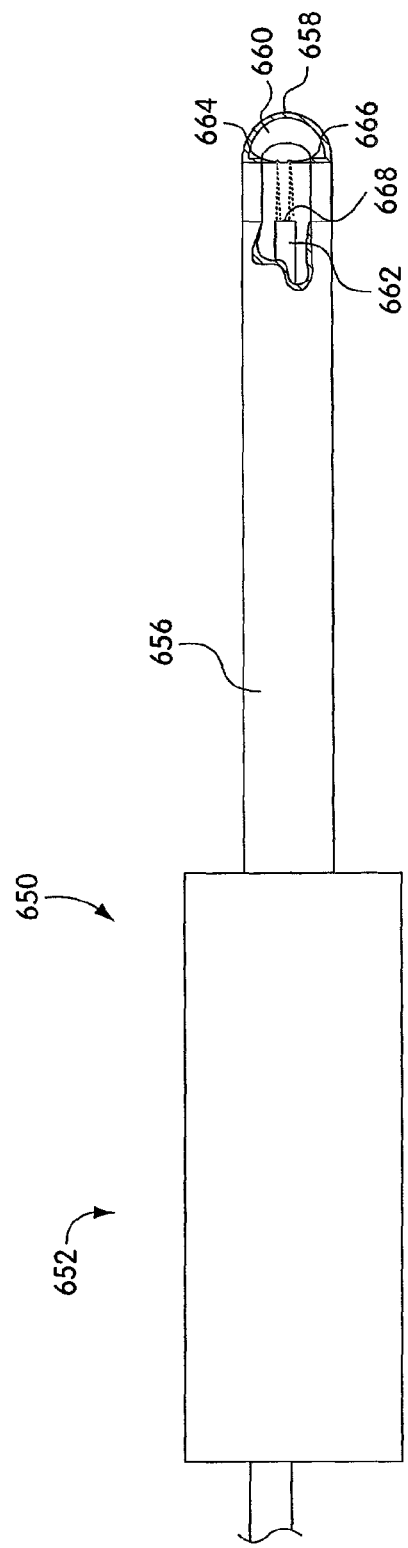

FIGS. 14a and 14b show an alternative embodiment for a surgical liquid jet instrument according to the invention. The embodiment shown in FIGS. 14a and 14b is particularly advantageous for use in procedures in a surrounding air environment involving debriding or ablating a material from an external surface of the body of a patient. Instrument 650 includes body 652 having a grasping portion 654 configured to be held in the hand of an operator. Extending distally from body 652 is a sheath 656, which extends distally to the extreme distal point 658 of instrument 652, and essentially completely surrounds pressure lumen 660 and evacuation lumen 662, (shown most clearly in FIG. 14*b*). As shown in FIG. 14*b*, pressure lumen 660 includes two jet nozzles 664 and 666 comprising holes bored in the sidewall of the pressure lumen 660. Each of nozzles 664 and 666 creates a diverging liquid jet, which is directed into jet receiving opening 668 at the distal end of evacuation lumen 662, as described previously. In alternative embodiments, evacuation lumen 662 may include only a single nozzle. The liquid jets emitted from nozzle 664 and 666 have central regions that are directed essentially parallel to the longitudinal axes of evacuation lumen 662, sheath 656, and body 652. In alternative embodiments, sheath 656, instead of being straight as illustrated, can be curved or angled near the distal end in order to provide a more advantageous ergonomic shape for certain surgical procedures (for example, see FIG. 2*b*).

In use, the surgical instrument according to the invention as illustrated in FIGS. 14*a* and 14*b*, can be utilized in a surgical procedure for debriding material from the skin, or external body surface of a patient. Such a surgical method involves positioning the inventive surgical liquid jet instrument in close proximity to an external surface on the body of a patient, and then creating a liquid jet by supplying a high pressure fluid to the instrument, so that at least a portion of the jet is directed essentially parallel to the surface of the body and so that essentially the entire jet is directed towards the jet-receiving opening in the evacuation lumen. The entrainment region created by the liquid jet, as discussed above, can be used to debride or ablate a material from the surface of the patient and evacuate the material, along with the liquid comprising the liquid jet, from the jet-receiving opening and through the evacuation lumen, preferably without utilizing an external source of suction. The method may be advantageously employed for cleaning wounds, surgical incisions, sites of infection, etc. The debrided material may comprise one or more of living tissue, dead tissue, or organic/inorganic foreign matter that may be embedded in the surface prior to debriding the surface with the instrument.

Those skilled in the art would readily appreciate that all parameters and configurations described herein are meant to be exemplary and that actual parameters and configurations will depend upon the specific application for which the instruments and methods of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described.

What is claimed is:

1. A device comprising:
   a surgical instrument having a distal end adapted to perform a surgical procedure on a patient and a proximal end adapted to be controllable by an operator, the instrument including a pressure lumen having sufficient burst strength to conduct a high pressure liquid towards the distal end of the instrument, the pressure lumen including at least one nozzle providing a jet opening; and
   an evacuation lumen, including a jet-receiving opening having a cross-sectional area and locatable opposite the jet opening at a predetermined distance therefrom to receive a liquid jet when the instrument is in operation;
   the nozzle being shaped to form a liquid jet as a liquid at high pressure flows therethrough, the liquid jet creating an entrainment region of moving liquid such that essentially all of the moving liquid in the entrainment region is directed into the jet-receiving opening when the instrument is in operation;
   the cross-sectional area of the jet-receiving opening and the predetermined distance being selected so that the entrainment region occupies between 50% and 100% of the cross-sectional area of the jet-receiving opening when the instrument is in operation; and
   wherein an axis defining a direction of at least a central region of the liquid jet and a longitudinal axis of the proximal end of the surgical instrument are non-parallel to each other when the instrument is in operation.

2. The device as in claim 1, wherein an angle between the axis defining a direction of at least a central region of the liquid jet and the longitudinal axis of the proximal end of the surgical instrument is between about 45 and about 115 degrees when the instrument is in operation.

3. The device as in claim 2, wherein an angle between the axis defining a direction of at least a central region of the liquid jet and the longitudinal axis of the proximal end of the surgical instrument is between about 80 and about 100 degrees when the instrument is in operation.

4. The device as in claim 3, wherein an angle between the axis defining a direction of at least a central region of the liquid jet and the longitudinal axis of the proximal end of the surgical instrument is about 90 degrees when the instrument is in operation.

5. A device comprising:
   a surgical instrument having a distal end adapted to perform a surgical procedure on a patient and a proximal end adapted to be controllable by an operator, the instrument including a pressure lumen having sufficient burst strength to conduct a high pressure liquid towards the distal end of the instrument, the pressure lumen including at least one nozzle providing a jet opening; and
   an evacuation lumen, including a jet-receiving opening having a cross-sectional area and locatable opposite the jet opening at a predetermined distance therefrom to receive a liquid jet when the instrument is in operation;
   the nozzle being shaped to form a liquid jet as a liquid at high pressure flows therethrough, the liquid jet creating an entrainment region of moving liquid such that essentially all of the moving liquid in the entrainment region is directed into the jet-receiving opening when the instrument is in operation;
   the cross-sectional area of the jet-receiving opening and the predetermined distance being selected so that the entrainment region occupies between 50% and 100% of the cross-sectional area of the jet-receiving opening when the instrument is in operation; and
   wherein at least one of a length to minimum internal diameter ratio of the nozzle and a cross-sectional area of the jet-receiving opening has a predetermined value selected based at least in part on the predetermined distance.

6. The device as in claim 5, wherein the distal end of the surgical instrument has a predetermined contour and size selected to facilitate insertion of the distal end into a confined region of a body defining a surgical operating space for a specific surgical procedure.

7. The device as in claim 6, wherein the distal end of the surgical instrument has a predetermined contour and size selected to facilitate insertion of the distal end into a joint capsule.

8. The device as in claim 5, wherein the predetermined distance is adjustable.

9. The device as in claim 5, wherein the surgical instrument includes a sheath surrounding at least a portion of the pressure lumen and the evacuation lumen.

10. The device as in claim 9, wherein the sheath has a proximal and a distal end, and wherein the distal end of the sheath is positionable proximal to an extreme distal point on the distal end of the instrument, and wherein at least one of the pressure lumen and the evacuation lumen extend distally from the distal end of the sheath.

11. The device as in claim 9, wherein at least one of the pressure lumen and the evacuation lumen is movable relative to the other.

12. The device as in claim 9, wherein at least one of the pressure lumen and the evacuation lumen is movable within the sheath.

13. The device as in claim 11, wherein movement of at least one of the pressure lumen and the evacuation lumen causes a change in the predetermined distance, the change in the predetermined distance causing a corresponding change in a cutting/ablating length of the liquid jet when the instrument is in operation.

14. The device as in claim 13, wherein the movement is controllable by manipulating at least a part of the proximal end of the surgical instrument.

15. A device as in claim 11, wherein the pressure lumen is essentially immovable and the evacuation lumen is movable relative to the pressure lumen.

16. The device as in claim 9, wherein the sheath is essentially straight with a longitudinal axis that is essentially parallel to a longitudinal axis of the proximal end of the surgical instrument.

17. The device as in claim 5, wherein the predetermined distance has a maximum value of about 1 cm.

18. The device as in claim 17, wherein the predetermined distance has a maximum value of about 5 mm.

19. The device as in claim 18, wherein the predetermined distance has a maximum value of about 1 mm.

20. The device as in claim 5, wherein the liquid at high pressure is supplied to the jet opening when the instrument is in operation at a pressure of at least 500 psig.

21. The device as in claim 20, wherein the liquid at high pressure is supplied to the jet opening when the instrument is in operation at a pressure of at least about 5,000 psig.

22. The device as in claim 21, wherein the liquid at high pressure is supplied to the jet opening when the instrument is in operation at a pressure of at least about 3,000 psig.

23. The device as in claim 22, wherein the liquid at high pressure is supplied to the jet opening when the instrument is in operation at a pressure of at least about 30,000 psig.

24. The device as in claim 23, wherein the liquid at high pressure is supplied to the jet opening when the instrument is in operation at a pressure of at least about 50,000 psig.

25. The device as in claim 5, wherein the jet opening has a diameter of between about 0.001 and about 0.02 inches.

26. The device as in claim 25, wherein the jet opening has a diameter of between about 0.003 and about 0.01 inches.

27. The device as in claim 26, wherein the jet opening has a diameter of about 0.005 inches.

28. The device as in claim 5, wherein the jet-receiving opening has a diameter of between about 0.01 and about 0.2 inches.

29. The device as in claim 28, wherein the jet-receiving opening has a diameter of between about 0.03 and about 0.1 inches.

30. The device as in claim 28, wherein the jet-receiving opening has a diameter of about 0.06 inches.

31. The device as in claim 5, wherein the proximal end of the surgical instrument includes a body, the body having a grasping region shaped and positionable to be held by a hand of the operator.

32. The device as in claim 5, wherein the surgical instrument is constructed and arranged to be entirely disposable after a single use.

33. The device as in claim 5, wherein the surgical instrument is constructed and arranged for operation in a liquid environment where at least the jet opening and the jet-receiving opening are submerged in a liquid when the instrument is in operation.

34. The device as in claim 33, wherein the liquid jet is an essentially collimated jet and wherein the entrainment region of moving liquid comprises a zone of liquid surrounding the collimated jet, the zone of liquid having a lower pressure than a liquid surrounding the zone.

35. The device as in claim 34, wherein the zone of liquid surrounding the collimated jet comprises a cavitation zone, the pressure of a least a portion of a liquid therein being below a vapor pressure the liquid.

36. The device as in claim 34, wherein the zone of liquid surrounding the collimated jet diverges in a direction from the jet opening to the jet-receiving opening so that the zone has an apex located at the jet opening.

37. The device as in claim 34, wherein the zone of liquid surrounding the collimated jet has a truncated cone shape.

38. The device as in claim 34, wherein the entrainment region occupies at least 75% of the cross-sectional area of the jet-receiving opening.

39. The device as in claim 38, wherein the entrainment region occupies at least 90% of the cross-sectional area of the jet-receiving opening.

40. The device as in claim 39, wherein the entrainment region occupies at least 95% of the cross-sectional area of the jet-receiving opening.

41. The device as in claim 5, wherein the evacuation lumen is shaped and positionable to enable evacuation of essentially all of the liquid comprising the liquid jet from the jet-receiving opening to a proximal end of the evacuation lumen without the need for an external source of suction.

42. The device as in claim 5, wherein the evacuation lumen includes a region at least one of within and downstream of the jet-receiving opening that is shaped so that a liquid within the region is able to macerate at least a portion of a tissue entrained in the liquid into a plurality of particles when the instrument is in operation.

43. The device as in claim 5, wherein the entrainment region and evacuation lumen are shaped and positionable to reduce a substantial fraction of a tissue entrained by the entrainment region to a plurality of microscopic particles during operation of the instrument.

44. The device as in claim 5, wherein the evacuation lumen has an internal cross-sectional area which increases continuously from a minimum value at the jet-receiving opening to a maximum value at a predetermined position proximal of the jet-receiving opening, which maximum value is essentially constant at positions proximal to the predetermined position.

45. The device as in claim 5, wherein the pressure lumen includes a proximal and a distal end, the distal end including the at least one nozzle and being shaped to enable at least one jet opening to be positionable adjacent to a surface to be ablated or debrided such that a liquid jet emanating from the jet opening is separated from the surface by a distance essentially equal to a wall thickness, at the jet opening, of tubing comprising the pressure lumen.

46. The device as in claim 5, wherein the entrainment region has a cross-sectional area at a plane defining the jet-receiving opening that is greater than about 50% of and less than or equal to about 100% of the cross-sectional area of the jet receiving opening when the instrument is in operation.

47. The device as in claim 5, wherein:
the distal end of the surgical instrument has a predetermined contour and size selected to facilitate insertion of the distal end into a confined region of a body defining a surgical operating space for a specific surgical procedure;
at least one of the pressure lumen and the evacuation lumen is movable relative to the other, and wherein movement of at least one of the pressure lumen and the evacuation lumen causes a change in the predetermined distance, the change in the predetermined distance causing a corresponding change in a length of the liquid jet when the instrument is in operation;
the proximal end of the surgical instrument includes a body, the body having a grasping region shaped and positionable to be held by a hand of the operator;
the entrainment region occupies at least 95% of the cross-sectional area of the jet-receiving opening; and
the evacuation lumen is shaped and positionable to enable evacuation of essentially all of the liquid comprising the liquid jet from the jet-receiving opening to a proximal end of the evacuation lumen without the need for an external source of suction.

48. A device comprising:
a surgical instrument having a distal end adapted to perform a surgical procedure on a patient and a proximal end adapted to be controllable by an operator, the instrument including a pressure lumen having sufficient burst strength to conduct a high pressure liquid towards the distal end of the instrument, the pressure lumen including at least one nozzle providing a jet opening; and
an evacuation lumen, including a jet-receiving opening having a cross-sectional area and locatable opposite the jet opening at a predetermined distance therefrom to receive a liquid jet when the instrument is in operation;
the nozzle being shaped to form a liquid jet as a liquid at high pressure flows therethrough, the liquid jet creating an entrainment region of moving liquid such that essentially all of the moving liquid in the entrainment region is directed into the jet-receiving opening when the instrument is in operation;
the cross-sectional area of the jet-receiving opening and the predetermined distance being selected so that the entrainment region occupies between 50% and 100% of the cross-sectional area of the jet-receiving opening when the instrument is in operation;
wherein the surgical instrument is constructed and arranged for operation in a liquid environment where at least the jet opening and the jet-receiving opening are submerged in a liquid when the instrument is in operation;
wherein the liquid jet is an essentially collimated jet and wherein the entrainment region of moving liquid comprises a zone of liquid surrounding the collimated jet, the zone of liquid having a lower pressure than a liquid surrounding the zone; and
wherein the nozzle has a region of minimum cross-sectional diameter having a predetermined length, the ratio of the predetermined length to the minimum cross-sectional diameter being not less than about four.

49. The device as in claim 48, wherein the ratio of the predetermined length to the minimum cross-sectional diameter is not less than about six.

50. The device as in claim 49, wherein the ratio of the predetermined length to the minimum cross-sectional diameter is not less than about ten.

51. A device comprising:
a surgical instrument having a distal end adapted to perform a surgical procedure on a patient and a proximal end adapted to be controllable by an operator, the instrument including a pressure lumen having sufficient burst strength to conduct a high pressure liquid towards the distal end of the instrument, the pressure lumen including at least one nozzle providing a jet opening; and
an evacuation lumen, including a jet-receiving opening having a cross-sectional area and locatable opposite the jet opening at a predetermined distance therefrom to receive a liquid jet when the instrument is in operation;
the nozzle being shaped to form a liquid jet as a liquid at high pressure flows therethrough, the liquid jet creating an entrainment region of moving liquid such that essentially all of the moving liquid in the entrainment region is directed into the jet-receiving opening when the instrument is in operation;
the cross-sectional area of the jet-receiving opening and the predetermined distance being selected so that the entrainment region occupies between 50% and 100% of the cross-sectional area of the jet-receiving opening when the instrument is in operation; and
wherein the pressure lumen comprises a tubular conduit having a distal end and a proximal end, the distal end of the tubular conduit having a necked region comprising the nozzle with a reduced cross-sectional dimension less than a cross-sectional dimension of the tubular conduit outside of and proximal to the necked region, the nozzle being oriented so that at least a central region of the liquid jet is directed essentially perpendicular to a longitudinal axis of the conduit outside the necked region, and the nozzle being shaped so that essentially no portion of the jet opening projects radially beyond a perimeter defined by an outer surface of the tubular conduit in a region adjacent to the nozzle but outside the necked region.

* * * * *